(12) United States Patent
Crooke et al.

(10) Patent No.: US 7,863,252 B2
(45) Date of Patent: Jan. 4, 2011

(54) MODULATION OF C-REACTIVE PROTEIN EXPRESSION

(75) Inventors: Rosanne M. Crooke, Carlsbad, CA (US); Mark J. Graham, San Clemente, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 183 days.

(21) Appl. No.: 11/969,208

(22) Filed: Jan. 3, 2008

(65) Prior Publication Data
US 2009/0170799 A1     Jul. 2, 2009

Related U.S. Application Data

(63) Continuation of application No. 10/858,500, filed on Jun. 1, 2004, now Pat. No. 7,425,545.

(60) Provisional application No. 60/475,272, filed on Jun. 2, 2003, provisional application No. 60/540,042, filed on Jan. 28, 2004.

(51) Int. Cl.
*A61K 31/70* (2006.01)
*C07H 21/02* (2006.01)
*C07H 21/04* (2006.01)
*C12Q 1/68* (2006.01)
*C12N 5/00* (2006.01)

(52) U.S. Cl. .................. 514/44 A; 435/6; 435/375; 536/23.1; 536/24.1; 536/24.5

(58) Field of Classification Search .................. None
See application file for complete search history.

(56) References Cited

U.S. PATENT DOCUMENTS

| | | |
|---|---|---|
| 5,582,979 A | 12/1996 | Weber |
| 5,783,179 A | 7/1998 | Nestor, Jr. et al. |
| 5,801,154 A | 9/1998 | Baracchini et al. |
| 5,998,148 A | 12/1999 | Bennett et al. |
| 6,582,908 B2 | 6/2003 | Fodor et al. |
| 6,764,826 B2 | 7/2004 | Yeh et al. |
| 6,770,461 B1 | 8/2004 | Carulli et al. |
| 6,964,950 B2 | 11/2005 | Crooke et al. |
| 7,250,496 B2 * | 7/2007 | Bentwich .............. 536/23.1 |
| 7,326,693 B2 | 2/2008 | Crooke et al. |
| 7,425,545 B2 | 9/2008 | Crooke et al. |
| 7,491,815 B2 | 2/2009 | Crooke et al. |
| 2002/0142283 A1 | 10/2002 | Yeh et al. |
| 2003/0083280 A1 | 5/2003 | Crooke et al. |
| 2003/0207834 A1 | 11/2003 | Dale et al. |
| 2004/0241651 A1 | 12/2004 | Olek et al. |
| 2005/0014257 A1 | 1/2005 | Crooke et al. |
| 2006/0024727 A1 | 2/2006 | Crooke et al. |

FOREIGN PATENT DOCUMENTS

| | | |
|---|---|---|
| WO | WO-96/06624 | 3/1996 |
| WO | WO-99/00418 | 1/1999 |
| WO | WO-00/11207 | 3/2000 |
| WO | WO 03/010284 | 2/2003 |

OTHER PUBLICATIONS

Verma et al., Annu. Rev. Biochem. vol. 67:99-134, 1998.*
Bennett et al., "Antisense oligonucleotides as a tool for gene functionalization and target validation", *Biochim. Biophys. Acta* Dec. 10, 1999 1489 (1):19-30.
Woo et al., "Characterization of genomic and complementary DNA sequence of human C-reactive protein, and comparison with the complementary DNA sequence of serum amyloid P component", *J. Biol. Chem.* Oct. 25, 1985 260 (24):13384-13388.
Agrawal, Sudhir, "Antisense oligonucleotides: towards clinical trials." *Tibtech* Oct. 1996 14:376-387.
Arici et al., "End-stage renal disease, atherosclerosis and cardiovascular mortality: Is C-reactive protein in the missing link?", *Kidney Intl.* Feb. 2001 59:407-414.
Bárány P., "Inflammation, serum C-reactive protein, and erythropoietin resistance", *Nephrol. Dial Transplant* Feb. 2001 16:224-227.
Branch, Andrea D., "A good antisense molecule is hard to find", *TIBS* Feb. 1998 45-50.
Gabay et al., "Acute-Phase Proteins and Other Systemic Responses to Inflammation", *New England J. of Medicine* Feb. 1999 340:448-454.
Highton et al., "The Presence and Possible Significance of C-Reactive Protein in Rheumatoid Inflammation", *J. Rheumatology* Oct. 1985 12:871-875.
Hulthe et al., "Relationship between C-reactive protein and intima-media thickness in the carotid and femoral arteries and to antibodies against oxidized low-density lipoprotein in healthy men: the Atherosclerosis and Insulin Resistance (AIR) study", *Clinical Science* Apr. 2001 100:371-378.

(Continued)

*Primary Examiner*—Sean R McGarry
(74) *Attorney, Agent, or Firm*—Isis Pharmaceuticals, Inc. Patent Dept.; Jones Day

(57) ABSTRACT

Compounds, compositions and methods are provided for modulating the expression of C-reactive protein. The compositions comprise oligonucleotides, targeted to nucleic acid encoding C-reactive protein. Methods of using these compounds for modulation of C-reactive protein expression and for diagnosis and treatment of disease associated with expression of C-reactive protein are provided.

45 Claims, No Drawings

OTHER PUBLICATIONS

Jen et al., "Suppression of Gene Expression by Targeted Disruption of Messenger RNA: Available Options and Current Strategies", *Stem Cells* Sep. 2000 18:307-319.

Lagrand et al., "C-Reactive Protein as a Cardiovascular Risk Factor More Than an Epiphenomenon?", *CRP and Cardiovascular Disease* Jul. 1999 100:96-102.

Lei et al., "Genomic DNA Sequence for Human C-reactive Protein", *J. Biol. Chem.* Oct. 1985 260(24): 13377-13383.

Morrow et al., "C-Reactive Protein, Inflammation, and Coronary Risk", *Med. Clinics of North America* Jan. 2000 84(1):149-161.

Ridker et al., "Measurement of C-Reactive Protein for the Targeting of Statin Therapy in the Primary Prevention of Acute Coronary Events", *N. Engl. J. Med.* Jun. 2001 344(6):1959-1965.

Ridker et al., "Rapid Reduction in C-Reactive Protein with Cerivastatin Among 785 Patients with Primary Hypercholesterolemia", *Circulation* Mar. 2001 103:1191-1193.

Ruuskanen et al., "C-reactive protein in respiratory virus infections", *J. Pediatrics* Jul. 1985 107:97-100.

Szalai et al., "C-Reactive Protein Structural Biology, Gene Expression, and Host Defense Function", *Immunologic Research* 1997 16/2:127-136.

Weintraub, Harold M., "Antisense RNA and DNA", *Scientific American* Jan. 1990 40-46.

Westhuyzen et al., "Review: Biology and Relevance of C-Reactive Protein in Cardiovascular and Renal Disease", *Annals of Clinical & Laboratory Science* Apr. 2000 30(2):133-143.

Yudkin et al., "Inflammation, obesity, stress and coronary heart disease: is interleukin-6 the link?", *Atherosclerosis* Feb. 2000 148:209-214.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

New England Biolabs, 1998/1999 Catalog, pp. 121 and 284.

Skerra et al., "Phosphorothioate primers improve the amplification of DNA sequences by DNA polymerases with proofreading activity", *Nucleic Acids Research* (1992) 20(14):3551-3554.

USPTO Office Action for U.S. Appl. No. 09/912,724 dated Sep. 20, 2002.

USPTO Final Rejection Office Action for U.S. Appl. No. 09/912,724 dated Mar. 13, 2003.

USPTO Office Action for U.S. Appl. No. 09/912,724 dated Dec. 15, 2003.

USPTO Final Rejection Office Action for U.S. Appl. No. 09/912,724 dated Jun. 9, 2004.

USPTO Final Rejection Office Action for U.S. Appl. No. 09/912,724 dated Dec. 9, 2004.

USPTO Notice of Allowance for U.S. Appl. No. 09/912,724 dated May 31, 2005 (6,964,950).

USPTO Office Action for U.S. Appl. No. 11/211,803 dated Nov. 1, 2007.

USPTO Notice of Allowance for U.S. Appl. No. 11/211,803 dated Oct. 10, 2008.

USPTO Office Action for U.S. Appl. No. 12/352,572 dated Jan. 21, 2010.

USPTO Notice of Allowance for U.S. Appl. No. 12/352,572 dated Jul. 23, 2010.

USPTO Restriction Requirement for U.S. Appl. No. 10/483,424 dated Jul. 24, 2006.

USPTO Office Action for U.S. Appl. No. 10/483,424 dated Nov. 22, 2006.

USPTO Notice of Allowance for U.S. Appl. No. 10/483,424 dated Sep. 14, 2007.

USPTO Restriction Requirement for U.S. Appl. No. 10/858,500 dated Jan. 11, 2007.

USPTO Notice of Allowance for U.S. Appl. No. 10/858,500 dated Mar. 13, 2008.

EP Supplementary Search Report for Euro Application No. 04752571.2 - 2405 dated Dec. 19, 2007.

EP Supplementary Search Report for Euro Application No. 02753388.4 dated Mar. 17, 2005.

PCT International Search Report for PCT Application No. PCT/US02/22656 dated Apr. 7, 2003 (WO 03/010284).

PCT International Written Opinion for PCT/US02/22656 dated Oct. 7, 2003 (WO 03/010284).

PCT International Search Report for PCT Application No. PCT/US2004/015576 dated Mar. 14, 2006 (WO 2005/005599).

\* cited by examiner

SEQUENCE LISTING

<160> NUMBER OF SEQ ID NOS: 627

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                               20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
gtgcgcgcga gcccgaaatc                                               20

<210> SEQ ID NO 3
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
atgcattctg cccccaagga                                               20

<210> SEQ ID NO 4
<211> LENGTH: 2480
<212> TYPE: DNA
<213> ORGANISM: H. sapiens
<220> FEATURE:
<221> NAME/KEY: CDS
<222> LOCATION: (571)...(1182)
<223> OTHER INFORMATION: Antisense Oligonucleotide

<400> SEQUENCE: 4
tttgcttccc ctcttcccga agctctgaca cctgccccaa caagcaatgt tggaaaatta      60
tttacatagt ggcgcaaact cccttactgc tttggatata aatccaggca ggaggaggta     120
gctctaaggc aagagatctg ggacttctag cccctgaact ttcagccgaa tacatctttt     180
ccaaaggagt gaattcaggc ccttgtatca ctggcagcag gacgtgacca tggagaagct     240
gttgtgtttc ttggtcttga ccagcctctc tcatgctttt ggccagacag gtaagggcca     300
ccccaggcta tgggagagtt ttgatctgag gtatggggt ggggtctaag actgcatgaa      360
cagtctcaaa aaaaaaaaa aaagactgta tgaacagaac agtggagcat ccttcatggt     420
gtgtgtgtgt gtgtgtgtgt gtgtgtgtgg tgtgtaactg gagaaggggt cagtctgttt     480
ctcaatctta aattctatac gtaagtgagg ggatagatct gtgtgatctg agaaacctct     540
cacatttgct tgttttctg gctcacagac atg tcg agg aag gct ttt gtg ttt      594
                                  Met Ser Arg Lys Ala Phe Val Phe
                                   1               5 ccc aaa gag tcg gat act tcc tat gta tcc ctc aaa gca ccg tta acg      642
Pro Lys Glu Ser Asp Thr Ser Tyr Val Ser Leu Lys Ala Pro Leu Thr
         10                  15                  20 aag cct ctc aaa gcc ttc act gtg tgc ctc cac ttc tac acg gaa ctg      690

```
              Lys Pro Leu Lys Ala Phe Thr Val Cys Leu His Phe Tyr Thr Glu Leu
               25              30                  35                  40 tcc tcg acc cgt ggg tac agt att ttc tcg tat gcc acc aag aga caa        738
Ser Ser Thr Arg Gly Tyr Ser Ile Phe Ser Tyr Ala Thr Lys Arg Gln
                45                  50                  55 gac aat gag att ctc ata ttt tgg tct aag gat ata gga tac agt ttt        786
Asp Asn Glu Ile Leu Ile Phe Trp Ser Lys Asp Ile Gly Tyr Ser Phe
                    60                  65                  70 aca gtg ggt ggg tct gaa ata tta ttc gag gtt cct gaa gtc aca gta        834
Thr Val Gly Gly Ser Glu Ile Leu Phe Glu Val Pro Glu Val Thr Val
            75                  80                  85 gct cca gta cac att tgt aca agc tgg gag tcc gcc tca ggg atc gtg        882
Ala Pro Val His Ile Cys Thr Ser Trp Glu Ser Ala Ser Gly Ile Val
        90                  95                  100 gag ttc tgg gta gat ggg aag ccc agg gtg agg aag agt ctg aag aag        930
Glu Phe Trp Val Asp Gly Lys Pro Arg Val Arg Lys Ser Leu Lys Lys
105                 110                 115                 120 gga tac act gtg ggg gca gaa gca agc atc atc ttg ggg cag gag cag        978
Gly Tyr Thr Val Gly Ala Glu Ala Ser Ile Ile Leu Gly Gln Glu Gln
                125                 130                 135 gat tcc ttc ggt ggg aac ttt gaa gga agc cag tcc ctg gtg gga gac       1026
Asp Ser Phe Gly Gly Asn Phe Glu Gly Ser Gln Ser Leu Val Gly Asp
            140                 145                 150 att gga aat gtg aac atg tgg gac ttt gtg ctc tca cca gat gag att       1074
Ile Gly Asn Val Asn Met Trp Asp Phe Val Leu Ser Pro Asp Glu Ile
        155                 160                 165 aac acc atc tat ctt ggc ggg ccc ttc agt cct aat gtc ctg aac tgg       1122
Asn Thr Ile Tyr Leu Gly Gly Pro Phe Ser Pro Asn Val Leu Asn Trp
170                 175                 180 cgg gca ctg aag tat gaa gtg caa ggc gaa gtg ttc acc aaa ccc cag       1170
Arg Ala Leu Lys Tyr Glu Val Gln Gly Glu Val Phe Thr Lys Pro Gln
                185                 190                 195                 200 ctg tgg ccc tga ggccagctgt gggtcctgaa ggtacctccc ggttttttac           1222
Leu Trp Pro * accgcatggg ccccacgtct ctgtctctgg tacctcccgc ttttttacac tgcatggttc     1282
ccacgtctct gtctctgggc ctttgttccc ctatatgcat tgaggcctgc tccaccctcc     1342
tcagcgcctg agaatggagg taaagtgtct ggtctgggag ctcgttaact atgctgggaa     1402
atggtccaaa agaatcagaa tttgaggtgt tttgttttca ttttatttc aagttggaca      1462 gatcttggag ataatttctt acctcacata gatgagaaaa ctaacaccca gaaaggagaa     1522
atgatgttat aaaaaactca taaggcaaga gctgagaagg aagcgctgat cttctattta     1582 attcccacc catgacccccc agaaagcagg agcattgccc acattcacag ggctcttcag     1642
tctcagaatc aggacactgg ccaggtgtct ggtttgggtc cagagtgctc atcatcatgt     1702
catagaactg ctgggcccag gtctcctgaa atgggaagcc cagcaatacc acgcagtccc     1762
tccactttct caaagcacac tggaaaggcc attagaattg ccccagcaga gcagatctgc     1822 ttttttttcca gagcaaaatg aagcactagg tataaatatg ttgttactgc caagaactta    1882
aatgactggt ttttgtttgc ttgcagtgct ttcttaattt tatggctctt ctgggaaact     1942
cctccccttt tccacacgaa ccttgtgggg ctgtgaattc tttcttcatc cccgcattcc     2002
caatataccc aggccacaag agtggacgtg aaccacaggg tgtcctgtca gaggagccca     2062
tctcccatct ccccagctcc ctatctggag gatagttgga tagttacgtg ttcctagcag     2122
gaccaactac agtcttccca aggattgagt tatggacttt gggagtgaga catcttcttg     2182
ctgctggatt tccaagctga gaggacgtga acctgggacc accagtagcc atcttgtttg     2242
```

```
ccacatggag agagactgtg aggacagaag ccaaactgga agtggaggag ccaagggatt    2302
gacaaacaac agagccttga ccacgtggag tctctgaatc agccttgtct ggaaccagat    2362
ctacacctgg actgcccagg tctataagcc aataaagccc ctgtttactt gagtgagtcc    2422 aagctgttttt ctgatagttg ctttagaagt tgtgactaac ttctctatga cctttgaa    2480
```

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5

```
tgaccagcct ctctcatgct t                                              21
```

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6

```
tccgactctt tgggaaacac a                                              21
```

<210> SEQ ID NO 7
<211> LENGTH: 15
<212> TYPE: DNA
<213> ORGANISM: Artificial Sequence
<220> FEATURE:
<223> OTHER INFORMATION: PCR Probe

<400> SEQUENCE: 7

```
tgtcgaggaa ggctt                                                     15
```

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8

```
gaaggtgaag gtcggagtc                                                 19
```

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9

```
gaagatggtg atgggatttc                                                20
```

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                          20

<210> SEQ ID NO 11
<211> LENGTH: 693
<212> TYPE: DNA
<213> ORGANISM: R. norvegicus
<220> FEATURE:
<221> NAME/KEY: CDS
<222> LOCATION: (1)...(693)
<223> OTHER INFORMATION: Antisense Oligonucleotide

<400> SEQUENCE: 11

| | | | | | | | | | | | | | | | | |
|---|---|---|---|---|---|---|---|---|---|---|---|---|---|---|---|---|
| atg | gag | aag | cta | cta | tgg | tgt | ctt | ctg | atc | acg | ata | agc | ttc | tct | cag | 48 |
| Met | Glu | Lys | Leu | Leu | Trp | Cys | Leu | Leu | Ile | Thr | Ile | Ser | Phe | Ser | Gln | |
| 1 | | | | 5 | | | | | 10 | | | | | 15 | | |

| gct | ttt | ggt | cat | gaa | gac | atg | tct | aaa | cag | gcc | ttc | gta | ttt | ccc | gga | 96 |
|---|---|---|---|---|---|---|---|---|---|---|---|---|---|---|---|---|
| Ala | Phe | Gly | His | Glu | Asp | Met | Ser | Lys | Gln | Ala | Phe | Val | Phe | Pro | Gly | |
| | | | 20 | | | | | 25 | | | | | 30 | | | |

| gtg | tca | gct | act | gcc | tat | gtg | tcc | ctg | gaa | gca | gag | tca | aag | aag | cca | 144 |
|---|---|---|---|---|---|---|---|---|---|---|---|---|---|---|---|---|
| Val | Ser | Ala | Thr | Ala | Tyr | Val | Ser | Leu | Glu | Ala | Glu | Ser | Lys | Lys | Pro | |
| | | 35 | | | | | 40 | | | | | 45 | | | | |

| ctg | gaa | gcc | ttc | act | gtg | tgt | ctc | tat | gcc | cac | gct | gat | gtg | agc | cga | 192 |
|---|---|---|---|---|---|---|---|---|---|---|---|---|---|---|---|---|
| Leu | Glu | Ala | Phe | Thr | Val | Cys | Leu | Tyr | Ala | His | Ala | Asp | Val | Ser | Arg | |
| 50 | | | | | 55 | | | | | 60 | | | | | | |

| agc | ttc | agc | atc | ttc | tct | tac | gct | acc | aag | acg | agc | ttt | aac | gag | att | 240 |
|---|---|---|---|---|---|---|---|---|---|---|---|---|---|---|---|---|
| Ser | Phe | Ser | Ile | Phe | Ser | Tyr | Ala | Thr | Lys | Thr | Ser | Phe | Asn | Glu | Ile | |
| 65 | | | | | 70 | | | | | 75 | | | | | 80 | |

| ctt | ctg | ttt | tgg | act | agg | ggt | caa | ggg | ttt | agt | att | gca | gta | ggt | ggg | 288 |
|---|---|---|---|---|---|---|---|---|---|---|---|---|---|---|---|---|
| Leu | Leu | Phe | Trp | Thr | Arg | Gly | Gln | Gly | Phe | Ser | Ile | Ala | Val | Gly | Gly | |
| | | | | 85 | | | | | 90 | | | | | 95 | | |

| cct | gaa | ata | ctg | ttc | agt | gct | tca | gaa | att | cct | gag | gta | cca | aca | cac | 336 |
|---|---|---|---|---|---|---|---|---|---|---|---|---|---|---|---|---|
| Pro | Glu | Ile | Leu | Phe | Ser | Ala | Ser | Glu | Ile | Pro | Glu | Val | Pro | Thr | His | |
| | | | 100 | | | | | 105 | | | | | 110 | | | |

| atc | tgt | gcc | acc | tgg | gag | tct | gct | aca | gga | att | gta | gag | ctt | tgg | ctt | 384 |
|---|---|---|---|---|---|---|---|---|---|---|---|---|---|---|---|---|
| Ile | Cys | Ala | Thr | Trp | Glu | Ser | Ala | Thr | Gly | Ile | Val | Glu | Leu | Trp | Leu | |
| | | 115 | | | | | 120 | | | | | 125 | | | | |

| gac | ggg | aaa | ccc | agg | gtg | cgg | aaa | agt | ctg | cag | aag | ggc | tac | att | gtg | 432 |
|---|---|---|---|---|---|---|---|---|---|---|---|---|---|---|---|---|
| Asp | Gly | Lys | Pro | Arg | Val | Arg | Lys | Ser | Leu | Gln | Lys | Gly | Tyr | Ile | Val | |
| 130 | | | | | 135 | | | | | 140 | | | | | | |

| ggg | aca | aat | gca | agc | atc | atc | ttg | ggg | cag | gag | cag | gac | tcg | tat | ggc | 480 |
|---|---|---|---|---|---|---|---|---|---|---|---|---|---|---|---|---|
| Gly | Thr | Asn | Ala | Ser | Ile | Ile | Leu | Gly | Gln | Glu | Gln | Asp | Ser | Tyr | Gly | |
| 145 | | | | | 150 | | | | | 155 | | | | | 160 | |

| ggt | ggc | ttt | gac | gcg | aat | cag | tct | ttg | gtg | gga | gac | att | gga | gat | gtg | 528 |
|---|---|---|---|---|---|---|---|---|---|---|---|---|---|---|---|---|
| Gly | Gly | Phe | Asp | Ala | Asn | Gln | Ser | Leu | Val | Gly | Asp | Ile | Gly | Asp | Val | |
| | | | | 165 | | | | | 170 | | | | | 175 | | |

| aac | atg | tgg | gac | ttt | gtg | cta | tct | cca | gaa | cag | atc | aat | gca | gtc | tat | 576 |
|---|---|---|---|---|---|---|---|---|---|---|---|---|---|---|---|---|
| Asn | Met | Trp | Asp | Phe | Val | Leu | Ser | Pro | Glu | Gln | Ile | Asn | Ala | Val | Tyr | |
| | | | 180 | | | | | 185 | | | | | 190 | | | |

| gtt | ggt | agg | gta | ttc | agc | ccc | aat | gtt | ttg | aac | tgg | cgg | gca | ctg | aag | 624 |
|---|---|---|---|---|---|---|---|---|---|---|---|---|---|---|---|---|
| Val | Gly | Arg | Val | Phe | Ser | Pro | Asn | Val | Leu | Asn | Trp | Arg | Ala | Leu | Lys | |
| | | 195 | | | | | 200 | | | | | 205 | | | | |

| tat | gaa | aca | cac | ggt | gat | gtg | ttt | atc | aag | ccg | cag | ctg | tgg | ccc | ttg | 672 |
|---|---|---|---|---|---|---|---|---|---|---|---|---|---|---|---|---|
| Tyr | Glu | Thr | His | Gly | Asp | Val | Phe | Ile | Lys | Pro | Gln | Leu | Trp | Pro | Leu | |
| | 210 | | | | | 215 | | | | | 220 | | | | | |

| act | gac | tgt | tgt | gag | tcc | tga | | | | | | | | | | 693 |
|---|---|---|---|---|---|---|---|---|---|---|---|---|---|---|---|---|
| Thr | Asp | Cys | Cys | Glu | Ser | * | | | | | | | | | | |
| 225 | | | | 230 | | | | | | | | | | | | |

<210> SEQ ID NO 12
<211> LENGTH: 19
<212> TYPE: DNA
<213> ORGANISM: Artificial Sequence

```
<220> FEATURE:
<223> OTHER INFORMATION: PCR Primer

<400> SEQUENCE: 12
aagcaccccc aatgtcacc                                                19

<210> SEQ ID NO 13
<211> LENGTH: 23
<212> TYPE: DNA
<213> ORGANISM: Artificial Sequence
<220> FEATURE:
<223> OTHER INFORMATION: PCR Primer

<400> SEQUENCE: 13
tgttctagag acagccgcat ctt                                           23

<210> SEQ ID NO 14
<211> LENGTH: 29
<212> TYPE: DNA
<213> ORGANISM: Artificial Sequence
<220> FEATURE:
<223> OTHER INFORMATION: PCR Probe

<400> SEQUENCE: 14 tcctggattcaagcttctatgtgccttca                                       29

<210> SEQ ID NO 15
<211> LENGTH: 23
<212> TYPE: DNA
<213> ORGANISM: Artificial Sequence
<220> FEATURE:
<223> OTHER INFORMATION: PCR Primer

<400> SEQUENCE: 15
tgttctagag acagccgcat ctt                                           23

<210> SEQ ID NO 16
<211> LENGTH: 21
<212> TYPE: DNA
<213> ORGANISM: Artificial Sequence
<220> FEATURE:
<223> OTHER INFORMATION: PCR Primer

<400> SEQUENCE: 16
caccgacctt caccatcttg t                                             21

<210> SEQ ID NO 17
<211> LENGTH: 24
<212> TYPE: DNA
<213> ORGANISM: Artificial Sequence
<220> FEATURE:
<223> OTHER INFORMATION: PCR Probe

<400> SEQUENCE: 17
ttgtgcagtg ccagcctcgt ctca                                          24

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
cctgccccaa gatgatgctt                                               20
```

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
gcaggtgtca gagcttcggg					20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gcagtaaggg agtttgcgcc					20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
gcctgaattc actcctttgg					20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
agcttctcca tggtcacgtc					20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
tggcccttac ctgtctggcc					20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ctcagatcaa aactctccca					20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 25
ttcatgcagt cttagacccc                                               20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
gtctgtgagc cagaaaaaca                                               20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
cgagaaaata ctgtacccac                                               20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
gacccaccca ctgtaaaact                                               20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
cagaactcca cgatccctga                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
attaggactg aagggcccgc                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
agctggcctc agggccacag                                               20

<210> SEQ ID NO 32
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gaggtacctt caggacccac                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
cccagaccag acactttacc                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
tggaccattt cccagcatag                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
ttctgagact gaagagccct                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
gcactctgga cccaaaccag                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
caggagacct gggcccagca                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
```

```
cccagaagag ccataaaatt                                           20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
attcacagcc ccacaaggtt                                           20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
agaagatgtc tcactcccaa                                           20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
tgtttgtcaa tcccttggct                                           20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ttctaaagca actatcagaa                                           20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
gccttagagc tacctcctcc                                           20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
ctgctgccag tgatacaagg                                           20

<210> SEQ ID NO 45
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 45
ccatacctca gatcaaaact                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
accccttctc cagttacaca                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
cagttccgtg tagaagtgga                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
gtatcctata tccttagacc                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
tggagctact gtgacttcag                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
cgatccctga ggcggactcc                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
ctcttcctca ccctgggctt                                              20
```

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
cagtgtatcc cttcttcaga                                       20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
gccccaagat gatgcttgct                                       20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
gtcccacatg ttcacatttc                                       20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
agtgcccgcc agttcaggac                                       20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
gtgaacactt cgccttgcac                                       20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
tccattctca ggcgctgagg                                       20

<210> SEQ ID NO 58
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 58
gaaattatct ccaagatctg                                              20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
cagcgcttcc ttctcagctc                                              20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
gtgaatgtgg gcaatgctcc                                              20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
acacctggcc agtgtcctga                                              20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
cctttccagt gtgctttgag                                              20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
tagtgcttca ttttgctctg                                              20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
tgaagaaaga attcacagcc                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
ggctcctctg acaggacacc                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
gctaggaaca cgtaactatc                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ggaagactgt agttggtcct                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
ctactggtgg tcccaggttc                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
cctccacttc cagtttggct                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
ctggttccag acaaggctga                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 71
gactcactca agtaaacagg                                            20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ttcaaaggtc atagagaagt                                            20

<210> SEQ ID NO 73
<211> LENGTH: 18
<212> TYPE: DNA
<213> ORGANISM: Artificial Sequence
<220> FEATURE:
<223> OTHER INFORMATION: PCR Primer

<400> SEQUENCE: 73 gcttccctc ttcccgaa                                               18

<210> SEQ ID NO 74
<211> LENGTH: 25
<212> TYPE: DNA
<213> ORGANISM: Artificial Sequence
<220> FEATURE:
<223> OTHER INFORMATION: PCR Primer

<400> SEQUENCE: 74
tgcgccacta tgtaaataat tttcc                                      25

<210> SEQ ID NO 75
<211> LENGTH: 26
<212> TYPE: DNA
<213> ORGANISM: Artificial Sequence
<220> FEATURE:
<223> OTHER INFORMATION: PCR Probe

<400> SEQUENCE: 75
tctgacacct gccccaacaa gcaatg                                     26

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
gtcagagctt cgggaagagg                                            20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
tttccaacat tgcttgttgg                                            20

<210> SEQ ID NO 78
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 78
tgtaaataat tttccaacat                                           20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
tgcgccacta tgtaaataat                                           20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
taagggagtt tgcgccacta                                           20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tccaaagcag taagggagtt                                           20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
tggatttata tccaaagcag                                           20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
tcctgcctgg atttatatcc                                           20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
```

| | |
|---|---|
| tagagctacc tcctcctgcc | 20 |

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85

| | |
|---|---|
| ccagatctct tgccttagag | 20 |

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86

| | |
|---|---|
| gctagaagtc ccagatctct | 20 |

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87

| | |
|---|---|
| gatgtattcg gctgaaagtt | 20 |

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88

| | |
|---|---|
| ctttggaaaa gatgtattcg | 20 |

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89

| | |
|---|---|
| tgatacaagg gcctgaattc | 20 |

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90

| | |
|---|---|
| acgtcctgct gccagtgata | 20 |

<210> SEQ ID NO 91
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 91
acaacagctt ctccatggtc                                                 20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gaaacacaac agcttctcca                                                 20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
tcaagaccaa gaaacacaac                                                 20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
gagaggctgg tcaagaccaa                                                 20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
agcatgagag aggctggtca                                                 20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
tctggccaaa agcatgagag                                                 20

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
cccttacctg tctggccaaa                                                 20
```

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ggtggccctt acctgtctgg                                        20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
cccatacctc agatcaaaac                                        20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gttcatgcag tcttagaccc                                        20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
agactgttca tgcagtctta                                        20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
tttgagactg ttcatgcagt                                        20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gttctgttca tacagtcttt                                        20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 104
ccactgttct gttcatacag                                               20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
atgctccact gttctgttca                                               20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gaaggatgct ccactgttct                                               20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
accatgaagg atgctccact                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
cacacaccat gaaggatgct                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
acacacacac accatgaagg                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
cccttctcca gttacacacc                                               20

<210> SEQ ID NO 111
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
acagactgac cccttctcca                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
agattgagaa acagactgac                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
atagaattta agattgagaa                                               20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
tcacttacgt atagaattta                                               20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
ccctcactta cgtatagaat                                               20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
atctatcccc tcacttacgt                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
```

```
agatcacaca gatctatccc                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
gaggtttctc agatcacaca                                               20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
gcaaatgtga gaggtttctc                                               20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
cgacatgtct gtgagccaga                                               20

<210> SEQ ID NO 121
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 121
ttcctcgaca tgtctgtgag                                               20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
aagccttcct cgacatgtct                                               20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
ggaagtatcc gactctttgg                                               20

<210> SEQ ID NO 124
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 124
ggatacatag gaagtatccg                                              20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
gtgctttgag ggatacatag                                              20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
ttcgttaacg gtgctttgag                                              20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
tttgagaggc ttcgttaacg                                              20

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
cagtgaaggc tttgagaggc                                              20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
tggaggcaca cagtgaaggc                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
agaagtggag gcacacagtg                                              20
```

```
<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
cgtgtagaag tggaggcaca                                               20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
aggacagttc cgtgtagaag                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
ccacgggtcg aggacagttc                                               20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
aatactgtac ccacgggtcg                                               20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
tctcttggtg gcatacgaga                                               20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
cattgtcttg tctcttggtg                                               20

<210> SEQ ID NO 137
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 137
atgagaatct cattgtcttg                                               20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
agaccaaaat atgagaatct                                               20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
ctatatcctt agaccaaaat                                               20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
aactgtatcc tatatcctta                                               20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
cccactgtaa aactgtatcc                                               20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
ttcagaccca cccactgtaa                                               20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
tcgaataata tttcagaccc                                               20

```
<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
ttcaggaacc tcgaataata                                               20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
ctactgtgac ttcaggaacc                                               20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
tgtactggag ctactgtgac                                               20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
tgtacaaatg tgtactggag                                               20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
actcccagct tgtacaaatg                                               20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
cctgaggcgg actcccagct                                               20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 150
gatccctgag gcggactccc                                                 20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
agaactccac gatccctgag                                                 20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
ccatctaccc agaactccac                                                 20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
cctgggcttc ccatctaccc                                                 20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
tcttcctcac cctgggcttc                                                 20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
ttcttcagac tcttcctcac                                                 20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
agtgtatccc ttcttcagac                                                 20

<210> SEQ ID NO 157
<211> LENGTH: 20
```

<212> TYPE: DNA
<213> ORGANISM: Artificial Sequence
<220> FEATURE:
<223> OTHER INFORMATION: Antisense Oligonucleotide

<400> SEQUENCE: 157
gatgatgctt gcttctgccc                                              20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
gaatcctgct cctgccccaa                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
aaggaatcct gctcctgccc                                              20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
gttcccaccg aaggaatcct                                              20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
ttccttcaaa gttcccaccg                                              20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
accagggact ggcttccttc                                              20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163

-continued aatgtctccc accagggact                                          20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
tcacatttcc aatgtctccc                                          20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
tcccacatgt tcacatttcc                                          20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
cagcacaaag tcccacatgt                                          20

<210> SEQ ID NO 167
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 167
catctggtga cagcacaaag                                          20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
gtgttaatct catctggtga                                          20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
aagatagatg gtgttaatct                                          20

<210> SEQ ID NO 170
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 170
caggacatta ggactgaagg                                          20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
cccgccagtt caggacatta                                          20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
tacttcagtg cccgccagtt                                          20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
ttgcacttca tacttcagtg                                          20

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
acacttcgcc ttgcacttca                                          20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
ggtttggtga acacttcgcc                                          20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
gggaggtacc ttcaggaccc                                          20
```

```
<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
taccagagac agagacgtgg                                               20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
aagcgggagg taccagagac                                               20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
gcccagagac agagacgtgg                                               20

<210> SEQ ID NO 180
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 180
gggaacaaag gcccagagac                                               20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
tgaggagggt ggagcaggcc                                               20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
attctcaggc gctgaggagg                                               20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 183
ctttacctcc attctcaggc                                              20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
agaccagaca ctttacctcc                                              20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
acgagctccc agaccagaca                                              20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
agcatagtta acgagctccc                                              20

<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187
accatttccc agcatagtta                                              20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188
attcttttgg accatttccc                                              20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
tcaaattctg attcttttgg                                              20

<210> SEQ ID NO 190
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
ccaagatctg tccaacttga                                              20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
tgtgaggtaa gaaattatct                                              20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
ttctcatcta tgtgaggtaa                                              20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 193
ggtgttagtt ttctcatcta                                              20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
ctcctttctg ggtgttagtt                                              20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
aacatcattt ctcctttctg                                              20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
```
agctcttgcc ttatgagttt                                              20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
cttccttctc agctcttgcc                                              20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
aagatcagcg cttccttctc                                              20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
aattaaatag aagatcagcg                                              20

<210> SEQ ID NO 200
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 200
gaagagccct gtgaatgtgg                                              20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
agtgtcctga ttctgagact                                              20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202
cccaaaccag acacctggcc                                              20

<210> SEQ ID NO 203
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 203
atgatgatga gcactctgga                                               20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
gttctatgac atgatgatga                                               20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
tcccatttca ggagacctgg                                               20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
ttgctgggct tcccatttca                                               20

<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
ctgcgtggta ttgctgggct                                               20

<210> SEQ ID NO 208
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 208
agtggaggga ctgcgtggta                                               20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
gtgctttgag aaagtggagg                                               20
```

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
attctaatgg cctttccagt                                            20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
aagcagatct gctctgctgg                                            20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
atttatacct agtgcttcat                                            20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 213
gtaacaacat atttatacct                                            20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
gttcttggca gtaacaacat                                            20

<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
agtcatttaa gttcttggca                                            20

<210> SEQ ID NO 216
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 216
agtttcccag aagagccata                                                20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
cccacaaggt tcgtgtggaa                                                20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
aattcacagc cccacaaggt                                                20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219
atgaagaaag aattcacagc                                                20

<210> SEQ ID NO 220
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 220
cttgtggcct gggtatattg                                                20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221
cacgtccact cttgtggcct                                                20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222
ccctgtggtt cacgtccact                                                20

```
<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
tgacaggaca ccctgtggtt                                              20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
tgggctcctc tgacaggaca                                              20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
tcctccagat agggagctgg                                              20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
tatccaacta tcctccagat                                              20

<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
aacacgtaac tatccaacta                                              20

<210> SEQ ID NO 228
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 228
tcctgctagg aacacgtaac                                              20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 229
ctgtagttgg tcctgctagg                                               20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
ccttgggaag actgtagttg                                               20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
ataactcaat ccttgggaag                                               20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232
cccaaagtcc ataactcaat                                               20

<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 233
atgtctcact cccaaagtcc                                               20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234
cagcaagaag atgtctcact                                               20

<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235
ggaaatccag cagcaagaag                                               20

<210> SEQ ID NO 236
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 236
ctctcagctt ggaaatccag                                              20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
ggttcacgtc ctctcagctt                                              20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
gtggtcccag gttcacgtcc                                              20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239
atggctactg gtggtcccag                                              20

<210> SEQ ID NO 240
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 240
ggcaaacaag atggctactg                                              20

<210> SEQ ID NO 241
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 241
ctctccatgt ggcaaacaag                                              20

<210> SEQ ID NO 242
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 242
```

```
ctcacagtct ctctccatgt                                         20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243
ggcttctgtc ctcacagtct                                         20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244
cttccagttt ggcttctgtc                                         20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245
ggctcctcca cttccagttt                                         20

<210> SEQ ID NO 246
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 246
tcaatccctt ggctcctcca                                         20

<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247
ctgttgtttg tcaatccctt                                         20

<210> SEQ ID NO 248
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 248
ggtcaaggct ctgttgtttg                                         20

<210> SEQ ID NO 249
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 249
gactccacgt ggtcaaggct                                              20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250
ctgattcaga gactccacgt                                              20

<210> SEQ ID NO 251
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 251
ccagacaagg ctgattcaga                                              20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252
agatctggtt ccagacaagg                                              20

<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 253
gtccaggtgt agatctggtt                                              20

<210> SEQ ID NO 254
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 254
gacctgggca gtccaggtgt                                              20

<210> SEQ ID NO 255
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 255
ttattggctt atagacctgg                                              20
```

```
<210> SEQ ID NO 256
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 256
acagcttgga ctcactcaag                                               20

<210> SEQ ID NO 257
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 257
cttctaaagc aactatcaga                                               20

<210> SEQ ID NO 258
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 258
ttagtcacaa cttctaaagc                                               20

<210> SEQ ID NO 259
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 259
catagagaag ttagtcacaa                                               20

<210> SEQ ID NO 260
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 260
caccatagta gcttctccat                                               20

<210> SEQ ID NO 261
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 261
agcttatcgt gatcagaaga                                               20

<210> SEQ ID NO 262
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 262
atgaccaaaa gcctgagaga                                               20

<210> SEQ ID NO 263
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 263
gcctgtttag acatgtcttc                                               20

<210> SEQ ID NO 264
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 264
acactccggg aaatacgaag                                               20

<210> SEQ ID NO 265
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 265
ggacacatag gcagtagctg                                               20

<210> SEQ ID NO 266
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 266
ttctttgact ctgcttccag                                               20

<210> SEQ ID NO 267
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 267
cagtgaaggc ttccagtggc                                               20

<210> SEQ ID NO 268
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 268
agcgtgggca tagagacaca                                               20

<210> SEQ ID NO 269
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 269
ctgaagcttc ggctcacatc                                                 20

<210> SEQ ID NO 270
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 270
tggtagcgta agagaagatg                                                 20

<210> SEQ ID NO 271
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 271
aatctcgtta aagctcgtct                                                 20

<210> SEQ ID NO 272
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 272
ctgcaatact aaacccttga                                                 20

<210> SEQ ID NO 273
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 273
cagtatttca ggcccaccta                                                 20

<210> SEQ ID NO 274
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 274
ggaatttctg aagcactgaa                                                 20

<210> SEQ ID NO 275
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 275
```

-continued

```
gatgtgtgtt ggtacctcag                                              20

<210> SEQ ID NO 276
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 276
caatgtagcc cttctgcaga                                              20

<210> SEQ ID NO 277
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 277
gatgcttgca tttgtcccca                                              20

<210> SEQ ID NO 278
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 278
tcctgctcct gccccaagat                                              20

<210> SEQ ID NO 279
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 279
caaagccacc gccatacgag                                              20

<210> SEQ ID NO 280
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 280
caccaaagac tgattcgcgt                                              20

<210> SEQ ID NO 281
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 281
ttcacatctc caatgtctcc                                              20

<210> SEQ ID NO 282
<211> LENGTH: 20
<212> TYPE: DNA
```

<213> ORGANISM: Artificial Sequence
<220> FEATURE:
<223> OTHER INFORMATION: Antisense Oligonucleotide

<400> SEQUENCE: 282
atagcacaaa gtcccacatg                                               20

<210> SEQ ID NO 283
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 283
tgcattgatc tgttctggag                                               20

<210> SEQ ID NO 284
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 284
aataccctac caacatagac                                               20

<210> SEQ ID NO 285
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 285
agtgcccgcc agttcaaaac                                               20

<210> SEQ ID NO 286
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 286
caccgtgtgt ttcatacttc                                               20

<210> SEQ ID NO 287
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 287
ctgcggcttg ataaacacat                                               20

<210> SEQ ID NO 288
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 288
cagtcagtca agggccacag                                               20

<210> SEQ ID NO 289
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 289
ggactcacaa cagtcagtca                                        20

<210> SEQ ID NO 290
<211> LENGTH: 20
<212> TYPE: DNA
<213> ORGANISM: H. sapiens
<220> FEATURE:
<223> OTHER INFORMATION: Antisense Oligonucleotide

<400> SEQUENCE: 290
cccgaagctc tgacacctgc                                        20

<210> SEQ ID NO 291
<211> LENGTH: 20
<212> TYPE: DNA
<213> ORGANISM: H. sapiens
<220> FEATURE:

<400> SEQUENCE: 291
ggcgcaaact cccttactgc                                        20

<210> SEQ ID NO 292
<211> LENGTH: 20
<212> TYPE: DNA
<213> ORGANISM: H. sapiens
<220> FEATURE:

<400> SEQUENCE: 292
ccaaaggagt gaattcaggc                                        20

<210> SEQ ID NO 293
<211> LENGTH: 20
<212> TYPE: DNA
<213> ORGANISM: H. sapiens
<220> FEATURE:

<400> SEQUENCE: 293
gacgtgacca tggagaagct                                        20

<210> SEQ ID NO 294
<211> LENGTH: 20
<212> TYPE: DNA
<213> ORGANISM: H. sapiens
<220> FEATURE:

<400> SEQUENCE: 294
ggccagacag gtaagggcca                                        20

<210> SEQ ID NO 295
<211> LENGTH: 20
<212> TYPE: DNA
<213> ORGANISM: H. sapiens
<220> FEATURE:

<400> SEQUENCE: 295
ggggtctaag actgcatgaa                                        20

```
<210> SEQ ID NO 296
<211> LENGTH: 20
<212> TYPE: DNA
<213> ORGANISM: H. sapiens
<220> FEATURE:

<400> SEQUENCE: 296
tgtttttctg gctcacagac                                                        20

<210> SEQ ID NO 297
<211> LENGTH: 20
<212> TYPE: DNA
<213> ORGANISM: H. sapiens
<220> FEATURE:

<400> SEQUENCE: 297
gtgggtacag tattttctcg                                                        20

<210> SEQ ID NO 298
<211> LENGTH: 20
<212> TYPE: DNA
<213> ORGANISM: H. sapiens
<220> FEATURE:

<400> SEQUENCE: 298
agttttacag tgggtgggtc                                                        20

<210> SEQ ID NO 299
<211> LENGTH: 20
<212> TYPE: DNA
<213> ORGANISM: H. sapiens
<220> FEATURE:

<400> SEQUENCE: 299
tcagggatcg tggagttctg                                                        20

<210> SEQ ID NO 300
<211> LENGTH: 20
<212> TYPE: DNA
<213> ORGANISM: H. sapiens
<220> FEATURE:

<400> SEQUENCE: 300
gcgggccctt cagtcctaat                                                        20

<210> SEQ ID NO 301
<211> LENGTH: 20
<212> TYPE: DNA
<213> ORGANISM: H. sapiens
<220> FEATURE:

<400> SEQUENCE: 301
ctgtggccct gaggccagct                                                        20

<210> SEQ ID NO 302
<211> LENGTH: 20
<212> TYPE: DNA
<213> ORGANISM: H. sapiens
<220> FEATURE:

<400> SEQUENCE: 302
gtgggtcctg aaggtacctc                                                        20
```

```
<210> SEQ ID NO 303
<211> LENGTH: 20
<212> TYPE: DNA
<213> ORGANISM: H. sapiens
<220> FEATURE:

<400> SEQUENCE: 303
ggtaaagtgt ctggtctggg                                                   20

<210> SEQ ID NO 304
<211> LENGTH: 20
<212> TYPE: DNA
<213> ORGANISM: H. sapiens
<220> FEATURE:

<400> SEQUENCE: 304
ctatgctggg aaatggtcca                                                   20

<210> SEQ ID NO 305
<211> LENGTH: 20
<212> TYPE: DNA
<213> ORGANISM: H. sapiens
<220> FEATURE:

<400> SEQUENCE: 305
ctggtttggg tccagagtgc                                                   20

<210> SEQ ID NO 306
<211> LENGTH: 20
<212> TYPE: DNA
<213> ORGANISM: H. sapiens
<220> FEATURE:

<400> SEQUENCE: 306
tgctgggccc aggtctcctg                                                   20

<210> SEQ ID NO 307
<211> LENGTH: 20
<212> TYPE: DNA
<213> ORGANISM: H. sapiens
<220> FEATURE:

<400> SEQUENCE: 307
aaccttgtgg ggctgtgaat                                                   20

<210> SEQ ID NO 308
<211> LENGTH: 20
<212> TYPE: DNA
<213> ORGANISM: H. sapiens
<220> FEATURE:

<400> SEQUENCE: 308
ttgggagtga gacatcttct                                                   20

<210> SEQ ID NO 309
<211> LENGTH: 20
<212> TYPE: DNA
<213> ORGANISM: H. sapiens
<220> FEATURE:

<400> SEQUENCE: 309
agccaaggga ttgacaaaca                                                   20

<210> SEQ ID NO 310
<211> LENGTH: 20
```

```
<212> TYPE: DNA
<213> ORGANISM: H. sapiens
<220> FEATURE:

<400> SEQUENCE: 310
ttctgatagt tgctttagaa                                              20

<210> SEQ ID NO 311
<211> LENGTH: 20
<212> TYPE: DNA
<213> ORGANISM: H. sapiens
<220> FEATURE:

<400> SEQUENCE: 311
ggaggaggta gctctaaggc                                              20

<210> SEQ ID NO 312
<211> LENGTH: 20
<212> TYPE: DNA
<213> ORGANISM: H. sapiens
<220> FEATURE:

<400> SEQUENCE: 312
ccttgtatca ctggcagcag                                              20

<210> SEQ ID NO 313
<211> LENGTH: 20
<212> TYPE: DNA
<213> ORGANISM: H. sapiens
<220> FEATURE:

<400> SEQUENCE: 313
tgtgtaactg gagaaggggt                                              20

<210> SEQ ID NO 314
<211> LENGTH: 20
<212> TYPE: DNA
<213> ORGANISM: H. sapiens
<220> FEATURE:

<400> SEQUENCE: 314
ggtctaagga tataggatac                                              20

<210> SEQ ID NO 315
<211> LENGTH: 20
<212> TYPE: DNA
<213> ORGANISM: H. sapiens
<220> FEATURE:

<400> SEQUENCE: 315
ctgaagtcac agtagctcca                                              20

<210> SEQ ID NO 316
<211> LENGTH: 20
<212> TYPE: DNA
<213> ORGANISM: H. sapiens
<220> FEATURE:

<400> SEQUENCE: 316
ggagtccgcc tcagggatcg                                              20

<210> SEQ ID NO 317
<211> LENGTH: 20
<212> TYPE: DNA
<213> ORGANISM: H. sapiens
```

```
<220> FEATURE:

<400> SEQUENCE: 317
aagcccaggg tgaggaagag                                                    20

<210> SEQ ID NO 318
<211> LENGTH: 20
<212> TYPE: DNA
<213> ORGANISM: H. sapiens
<220> FEATURE:

<400> SEQUENCE: 318
tctgaagaag ggatacactg                                                    20

<210> SEQ ID NO 319
<211> LENGTH: 20
<212> TYPE: DNA
<213> ORGANISM: H. sapiens
<220> FEATURE:

<400> SEQUENCE: 319
agcaagcatc atcttggggc                                                    20

<210> SEQ ID NO 320
<211> LENGTH: 20
<212> TYPE: DNA
<213> ORGANISM: H. sapiens
<220> FEATURE:

<400> SEQUENCE: 320
gaaatgtgaa catgtgggac                                                    20

<210> SEQ ID NO 321
<211> LENGTH: 20
<212> TYPE: DNA
<213> ORGANISM: H. sapiens
<220> FEATURE:

<400> SEQUENCE: 321
gtcctgaact ggcgggcact                                                    20

<210> SEQ ID NO 322
<211> LENGTH: 20
<212> TYPE: DNA
<213> ORGANISM: H. sapiens
<220> FEATURE:

<400> SEQUENCE: 322
gtgcaaggcg aagtgttcac                                                    20

<210> SEQ ID NO 323
<211> LENGTH: 20
<212> TYPE: DNA
<213> ORGANISM: H. sapiens
<220> FEATURE:

<400> SEQUENCE: 323
cctcagcgcc tgagaatgga                                                    20

<210> SEQ ID NO 324
<211> LENGTH: 20
<212> TYPE: DNA
<213> ORGANISM: H. sapiens
<220> FEATURE:
```

```
<400> SEQUENCE: 324
gagctgagaa ggaagcgctg                                          20

<210> SEQ ID NO 325
<211> LENGTH: 20
<212> TYPE: DNA
<213> ORGANISM: H. sapiens
<220> FEATURE:

<400> SEQUENCE: 325
ggagcattgc ccacattcac                                          20

<210> SEQ ID NO 326
<211> LENGTH: 20
<212> TYPE: DNA
<213> ORGANISM: H. sapiens
<220> FEATURE:

<400> SEQUENCE: 326
tcaggacact ggccaggtgt                                          20

<210> SEQ ID NO 327
<211> LENGTH: 20
<212> TYPE: DNA
<213> ORGANISM: H. sapiens
<220> FEATURE:

<400> SEQUENCE: 327
ctcaaagcac actggaaagg                                          20

<210> SEQ ID NO 328
<211> LENGTH: 20
<212> TYPE: DNA
<213> ORGANISM: H. sapiens
<220> FEATURE:

<400> SEQUENCE: 328
cagagcaaaa tgaagcacta                                          20

<210> SEQ ID NO 329
<211> LENGTH: 20
<212> TYPE: DNA
<213> ORGANISM: H. sapiens
<220> FEATURE:

<400> SEQUENCE: 329
ggctgtgaat tctttcttca                                          20

<210> SEQ ID NO 330
<211> LENGTH: 20
<212> TYPE: DNA
<213> ORGANISM: H. sapiens
<220> FEATURE:

<400> SEQUENCE: 330
ggtgtcctgt cagaggagcc                                          20

<210> SEQ ID NO 331
<211> LENGTH: 20
<212> TYPE: DNA
<213> ORGANISM: H. sapiens
<220> FEATURE:

<400> SEQUENCE: 331
```

-continued

```
gatagttacg tgttcctagc                                          20

<210> SEQ ID NO 332
<211> LENGTH: 20
<212> TYPE: DNA
<213> ORGANISM: H. sapiens
<220> FEATURE:

<400> SEQUENCE: 332
gaacctggga ccaccagtag                                          20

<210> SEQ ID NO 333
<211> LENGTH: 20
<212> TYPE: DNA
<213> ORGANISM: H. sapiens
<220> FEATURE:

<400> SEQUENCE: 333
agccaaactg gaagtggagg                                          20

<210> SEQ ID NO 334
<211> LENGTH: 20
<212> TYPE: DNA
<213> ORGANISM: H. sapiens
<220> FEATURE:

<400> SEQUENCE: 334
tcagccttgt ctggaaccag                                          20

<210> SEQ ID NO 335
<211> LENGTH: 20
<212> TYPE: DNA
<213> ORGANISM: H. sapiens
<220> FEATURE:

<400> SEQUENCE: 335
cctgtttact tgagtgagtc                                          20

<210> SEQ ID NO 336
<211> LENGTH: 20
<212> TYPE: DNA
<213> ORGANISM: H. sapiens
<220> FEATURE:

<400> SEQUENCE: 336
ctctaaggca agagatctgg                                          20

<210> SEQ ID NO 337
<211> LENGTH: 20
<212> TYPE: DNA
<213> ORGANISM: H. sapiens
<220> FEATURE:

<400> SEQUENCE: 337
tgaccagcct ctctcatgct                                          20

<210> SEQ ID NO 338
<211> LENGTH: 20
<212> TYPE: DNA
<213> ORGANISM: H. sapiens
<220> FEATURE:

<400> SEQUENCE: 338
gtcagtctgt ttctcaatct                                          20
```

```
<210> SEQ ID NO 339
<211> LENGTH: 20
<212> TYPE: DNA
<213> ORGANISM: H. sapiens
<220> FEATURE:

<400> SEQUENCE: 339
ctcacagaca tgtcgaggaa                                               20

<210> SEQ ID NO 340
<211> LENGTH: 20
<212> TYPE: DNA
<213> ORGANISM: H. sapiens
<220> FEATURE:

<400> SEQUENCE: 340
agacatgtcg aggaaggctt                                               20

<210> SEQ ID NO 341
<211> LENGTH: 20
<212> TYPE: DNA
<213> ORGANISM: H. sapiens
<220> FEATURE:

<400> SEQUENCE: 341
gccttcactg tgtgcctcca                                               20

<210> SEQ ID NO 342
<211> LENGTH: 20
<212> TYPE: DNA
<213> ORGANISM: H. sapiens
<220> FEATURE:

<400> SEQUENCE: 342
tctcgtatgc caccaagaga                                               20

<210> SEQ ID NO 343
<211> LENGTH: 20
<212> TYPE: DNA
<213> ORGANISM: H. sapiens
<220> FEATURE:

<400> SEQUENCE: 343
caccaagaga caagacaatg                                               20

<210> SEQ ID NO 344
<211> LENGTH: 20
<212> TYPE: DNA
<213> ORGANISM: H. sapiens
<220> FEATURE:

<400> SEQUENCE: 344
caagacaatg agattctcat                                               20

<210> SEQ ID NO 345
<211> LENGTH: 20
<212> TYPE: DNA
<213> ORGANISM: H. sapiens
<220> FEATURE:

<400> SEQUENCE: 345
ggttcctgaa gtcacagtag                                               20

<210> SEQ ID NO 346
```

```
<211> LENGTH: 20
<212> TYPE: DNA
<213> ORGANISM: H. sapiens
<220> FEATURE:

<400> SEQUENCE: 346
ctccagtaca catttgtaca                                                    20

<210> SEQ ID NO 347
<211> LENGTH: 20
<212> TYPE: DNA
<213> ORGANISM: H. sapiens
<220> FEATURE:

<400> SEQUENCE: 347
agctgggagt ccgcctcagg                                                    20

<210> SEQ ID NO 348
<211> LENGTH: 20
<212> TYPE: DNA
<213> ORGANISM: H. sapiens
<220> FEATURE:

<400> SEQUENCE: 348
gggagtccgc ctcagggatc                                                    20

<210> SEQ ID NO 349
<211> LENGTH: 20
<212> TYPE: DNA
<213> ORGANISM: H. sapiens
<220> FEATURE:

<400> SEQUENCE: 349
gaagcccagg gtgaggaaga                                                    20

<210> SEQ ID NO 350
<211> LENGTH: 20
<212> TYPE: DNA
<213> ORGANISM: H. sapiens
<220> FEATURE:

<400> SEQUENCE: 350
gggcagaagc aagcatcatc                                                    20

<210> SEQ ID NO 351
<211> LENGTH: 20
<212> TYPE: DNA
<213> ORGANISM: H. sapiens
<220> FEATURE:

<400> SEQUENCE: 351
gggcaggagc aggattcctt                                                    20

<210> SEQ ID NO 352
<211> LENGTH: 20
<212> TYPE: DNA
<213> ORGANISM: H. sapiens
<220> FEATURE:

<400> SEQUENCE: 352
cggtgggaac tttgaaggaa                                                    20

<210> SEQ ID NO 353
<211> LENGTH: 20
<212> TYPE: DNA
```

<213> ORGANISM: H. sapiens
<220> FEATURE:

<400> SEQUENCE: 353
gaaggaagcc agtccctggt                                               20

<210> SEQ ID NO 354
<211> LENGTH: 20
<212> TYPE: DNA
<213> ORGANISM: H. sapiens
<220> FEATURE:

<400> SEQUENCE: 354
gggagacatt ggaaatgtga                                               20

<210> SEQ ID NO 355
<211> LENGTH: 20
<212> TYPE: DNA
<213> ORGANISM: H. sapiens
<220> FEATURE:

<400> SEQUENCE: 355
acatgtggga ctttgtgctg                                               20

<210> SEQ ID NO 356
<211> LENGTH: 20
<212> TYPE: DNA
<213> ORGANISM: H. sapiens
<220> FEATURE:

<400> SEQUENCE: 356
ctttgtgctg tcaccagatg                                               20

<210> SEQ ID NO 357
<211> LENGTH: 20
<212> TYPE: DNA
<213> ORGANISM: H. sapiens
<220> FEATURE:

<400> SEQUENCE: 357
ccttcagtcc taatgtcctg                                               20

<210> SEQ ID NO 358
<211> LENGTH: 20
<212> TYPE: DNA
<213> ORGANISM: H. sapiens
<220> FEATURE:

<400> SEQUENCE: 358
taatgtcctg aactggcggg                                               20

<210> SEQ ID NO 359
<211> LENGTH: 20
<212> TYPE: DNA
<213> ORGANISM: H. sapiens
<220> FEATURE:

<400> SEQUENCE: 359
cactgaagta tgaagtgcaa                                               20

<210> SEQ ID NO 360
<211> LENGTH: 20
<212> TYPE: DNA
<213> ORGANISM: H. sapiens
<220> FEATURE:

-continued

```
<400> SEQUENCE: 360
tgaagtgcaa ggcgaagtgt                                              20

<210> SEQ ID NO 361
<211> LENGTH: 20
<212> TYPE: DNA
<213> ORGANISM: H. sapiens
<220> FEATURE:

<400> SEQUENCE: 361
ggcgaagtgt tcaccaaacc                                              20

<210> SEQ ID NO 362
<211> LENGTH: 20
<212> TYPE: DNA
<213> ORGANISM: H. sapiens
<220> FEATURE:

<400> SEQUENCE: 362
ccacgtctct gtctctggta                                              20

<210> SEQ ID NO 363
<211> LENGTH: 20
<212> TYPE: DNA
<213> ORGANISM: H. sapiens
<220> FEATURE:

<400> SEQUENCE: 363
gtctctggta cctcccgctt                                              20

<210> SEQ ID NO 364
<211> LENGTH: 20
<212> TYPE: DNA
<213> ORGANISM: H. sapiens
<220> FEATURE:

<400> SEQUENCE: 364
ccacgtctct gtctctgggc                                              20

<210> SEQ ID NO 365
<211> LENGTH: 20
<212> TYPE: DNA
<213> ORGANISM: H. sapiens
<220> FEATURE:

<400> SEQUENCE: 365
gtctctgggc ctttgttccc                                              20

<210> SEQ ID NO 366
<211> LENGTH: 20
<212> TYPE: DNA
<213> ORGANISM: H. sapiens
<220> FEATURE:

<400> SEQUENCE: 366
gcctgagaat ggaggtaaag                                              20

<210> SEQ ID NO 367
<211> LENGTH: 20
<212> TYPE: DNA
<213> ORGANISM: H. sapiens
<220> FEATURE:

<400> SEQUENCE: 367
```
tgtctggtct gggagctcgt                                               20

<210> SEQ ID NO 368
<211> LENGTH: 20
<212> TYPE: DNA
<213> ORGANISM: H. sapiens
<220> FEATURE:

<400> SEQUENCE: 368
gggagctcgt taactatgct                                               20

<210> SEQ ID NO 369
<211> LENGTH: 20
<212> TYPE: DNA
<213> ORGANISM: H. sapiens
<220> FEATURE:

<400> SEQUENCE: 369
tcaagttgga cagatcttgg                                               20

<210> SEQ ID NO 370
<211> LENGTH: 20
<212> TYPE: DNA
<213> ORGANISM: H. sapiens
<220> FEATURE:

<400> SEQUENCE: 370
ttacctcaca tagatgagaa                                               20

<210> SEQ ID NO 371
<211> LENGTH: 20
<212> TYPE: DNA
<213> ORGANISM: H. sapiens
<220> FEATURE:

<400> SEQUENCE: 371
tagatgagaa aactaacacc                                               20

<210> SEQ ID NO 372
<211> LENGTH: 20
<212> TYPE: DNA
<213> ORGANISM: H. sapiens
<220> FEATURE:

<400> SEQUENCE: 372
aactaacacc cagaaaggag                                               20

<210> SEQ ID NO 373
<211> LENGTH: 20
<212> TYPE: DNA
<213> ORGANISM: H. sapiens
<220> FEATURE:

<400> SEQUENCE: 373
aaactcataa ggcaagagct                                               20

<210> SEQ ID NO 374
<211> LENGTH: 20
<212> TYPE: DNA
<213> ORGANISM: H. sapiens
<220> FEATURE:

<400> SEQUENCE: 374
ggcaagagct gagaaggaag                                               20

```
<210> SEQ ID NO 375
<211> LENGTH: 20
<212> TYPE: DNA
<213> ORGANISM: H. sapiens
<220> FEATURE:

<400> SEQUENCE: 375
gagaaggaag cgctgatctt                                                   20

<210> SEQ ID NO 376
<211> LENGTH: 20
<212> TYPE: DNA
<213> ORGANISM: H. sapiens
<220> FEATURE:

<400> SEQUENCE: 376
cgctgatctt ctatttaatt                                                   20

<210> SEQ ID NO 377
<211> LENGTH: 20
<212> TYPE: DNA
<213> ORGANISM: H. sapiens
<220> FEATURE:

<400> SEQUENCE: 377
agtctcagaa tcaggacact                                                   20

<210> SEQ ID NO 378
<211> LENGTH: 20
<212> TYPE: DNA
<213> ORGANISM: H. sapiens
<220> FEATURE:

<400> SEQUENCE: 378
ggccaggtgt ctggtttggg                                                   20

<210> SEQ ID NO 379
<211> LENGTH: 20
<212> TYPE: DNA
<213> ORGANISM: H. sapiens
<220> FEATURE:

<400> SEQUENCE: 379
tccagagtgc tcatcatcat                                                   20

<210> SEQ ID NO 380
<211> LENGTH: 20
<212> TYPE: DNA
<213> ORGANISM: H. sapiens
<220> FEATURE:

<400> SEQUENCE: 380
tcatcatcat gtcatagaac                                                   20

<210> SEQ ID NO 381
<211> LENGTH: 20
<212> TYPE: DNA
<213> ORGANISM: H. sapiens
<220> FEATURE:

<400> SEQUENCE: 381
ccaggtctcc tgaaatggga                                                   20
```

```
<210> SEQ ID NO 382
<211> LENGTH: 20
<212> TYPE: DNA
<213> ORGANISM: H. sapiens
<220> FEATURE:

<400> SEQUENCE: 382
agcccagcaa taccacgcag                                                 20

<210> SEQ ID NO 383
<211> LENGTH: 20
<212> TYPE: DNA
<213> ORGANISM: H. sapiens
<220> FEATURE:

<400> SEQUENCE: 383
taccacgcag tccctccact                                                 20

<210> SEQ ID NO 384
<211> LENGTH: 20
<212> TYPE: DNA
<213> ORGANISM: H. sapiens
<220> FEATURE:

<400> SEQUENCE: 384
cctccacttt ctcaaagcac                                                 20

<210> SEQ ID NO 385
<211> LENGTH: 20
<212> TYPE: DNA
<213> ORGANISM: H. sapiens
<220> FEATURE:

<400> SEQUENCE: 385
actggaaagg ccattagaat                                                 20

<210> SEQ ID NO 386
<211> LENGTH: 20
<212> TYPE: DNA
<213> ORGANISM: H. sapiens
<220> FEATURE:

<400> SEQUENCE: 386
ccagcagagc agatctgctt                                                 20

<210> SEQ ID NO 387
<211> LENGTH: 20
<212> TYPE: DNA
<213> ORGANISM: H. sapiens
<220> FEATURE:

<400> SEQUENCE: 387
atgaagcact aggtataaat                                                 20

<210> SEQ ID NO 388
<211> LENGTH: 20
<212> TYPE: DNA
<213> ORGANISM: H. sapiens
<220> FEATURE:

<400> SEQUENCE: 388
atgttgttac tgccaagaac                                                 20

<210> SEQ ID NO 389
<211> LENGTH: 20
```

```
<212> TYPE: DNA
<213> ORGANISM: H. sapiens
<220> FEATURE:

<400> SEQUENCE: 389
tgccaagaac ttaaatgact                                          20

<210> SEQ ID NO 390
<211> LENGTH: 20
<212> TYPE: DNA
<213> ORGANISM: H. sapiens
<220> FEATURE:

<400> SEQUENCE: 390
ttccacacga accttgtggg                                          20

<210> SEQ ID NO 391
<211> LENGTH: 20
<212> TYPE: DNA
<213> ORGANISM: H. sapiens
<220> FEATURE:

<400> SEQUENCE: 391
caatataccc aggccacaag                                          20

<210> SEQ ID NO 392
<211> LENGTH: 20
<212> TYPE: DNA
<213> ORGANISM: H. sapiens
<220> FEATURE:

<400> SEQUENCE: 392
aggccacaag agtggacgtg                                          20

<210> SEQ ID NO 393
<211> LENGTH: 20
<212> TYPE: DNA
<213> ORGANISM: H. sapiens
<220> FEATURE:

<400> SEQUENCE: 393
agtggacgtg aaccacaggg                                          20

<210> SEQ ID NO 394
<211> LENGTH: 20
<212> TYPE: DNA
<213> ORGANISM: H. sapiens
<220> FEATURE:

<400> SEQUENCE: 394
tgtcctgtca gaggagccca                                          20

<210> SEQ ID NO 395
<211> LENGTH: 20
<212> TYPE: DNA
<213> ORGANISM: H. sapiens
<220> FEATURE:

<400> SEQUENCE: 395
gttacgtgtt cctagcagga                                          20

<210> SEQ ID NO 396
<211> LENGTH: 20
<212> TYPE: DNA
<213> ORGANISM: H. sapiens
```

```
<220> FEATURE:

<400> SEQUENCE: 396
cctagcagga ccaactacag                                                   20

<210> SEQ ID NO 397
<211> LENGTH: 20
<212> TYPE: DNA
<213> ORGANISM: H. sapiens
<220> FEATURE:

<400> SEQUENCE: 397
agtgagacat cttcttgctg                                                   20

<210> SEQ ID NO 398
<211> LENGTH: 20
<212> TYPE: DNA
<213> ORGANISM: H. sapiens
<220> FEATURE:

<400> SEQUENCE: 398
ctggatttcc aagctgagag                                                   20

<210> SEQ ID NO 399
<211> LENGTH: 20
<212> TYPE: DNA
<213> ORGANISM: H. sapiens
<220> FEATURE:

<400> SEQUENCE: 399
aagctgagag gacgtgaacc                                                   20

<210> SEQ ID NO 400
<211> LENGTH: 20
<212> TYPE: DNA
<213> ORGANISM: H. sapiens
<220> FEATURE:

<400> SEQUENCE: 400
ggacgtgaac ctgggaccac                                                   20

<210> SEQ ID NO 401
<211> LENGTH: 20
<212> TYPE: DNA
<213> ORGANISM: H. sapiens
<220> FEATURE:

<400> SEQUENCE: 401
cagtagccat cttgtttgcc                                                   20

<210> SEQ ID NO 402
<211> LENGTH: 20
<212> TYPE: DNA
<213> ORGANISM: H. sapiens
<220> FEATURE:

<400> SEQUENCE: 402
cttgtttgcc acatggagag                                                   20

<210> SEQ ID NO 403
<211> LENGTH: 20
<212> TYPE: DNA
<213> ORGANISM: H. sapiens
<220> FEATURE:
```

```
<400> SEQUENCE: 403
acatggagag agactgtgag                                              20

<210> SEQ ID NO 404
<211> LENGTH: 20
<212> TYPE: DNA
<213> ORGANISM: H. sapiens
<220> FEATURE:

<400> SEQUENCE: 404
agactgtgag gacagaagcc                                              20

<210> SEQ ID NO 405
<211> LENGTH: 20
<212> TYPE: DNA
<213> ORGANISM: H. sapiens
<220> FEATURE:

<400> SEQUENCE: 405
gacagaagcc aaactggaag                                              20

<210> SEQ ID NO 406
<211> LENGTH: 20
<212> TYPE: DNA
<213> ORGANISM: H. sapiens
<220> FEATURE:

<400> SEQUENCE: 406
aaactggaag tggaggagcc                                              20

<210> SEQ ID NO 407
<211> LENGTH: 20
<212> TYPE: DNA
<213> ORGANISM: H. sapiens
<220> FEATURE:

<400> SEQUENCE: 407
tggaggagcc aagggattga                                              20

<210> SEQ ID NO 408
<211> LENGTH: 20
<212> TYPE: DNA
<213> ORGANISM: H. sapiens
<220> FEATURE:

<400> SEQUENCE: 408
aagggattga caaacaacag                                              20

<210> SEQ ID NO 409
<211> LENGTH: 20
<212> TYPE: DNA
<213> ORGANISM: H. sapiens
<220> FEATURE:

<400> SEQUENCE: 409
agccttgacc acgtggagtc                                              20

<210> SEQ ID NO 410
<211> LENGTH: 20
<212> TYPE: DNA
<213> ORGANISM: H. sapiens
<220> FEATURE:

<400> SEQUENCE: 410
```
acgtggagtc tctgaatcag                                              20

<210> SEQ ID NO 411
<211> LENGTH: 20
<212> TYPE: DNA
<213> ORGANISM: H. sapiens
<220> FEATURE:

<400> SEQUENCE: 411
ccttgtctgg aaccagatct                                              20

<210> SEQ ID NO 412
<211> LENGTH: 20
<212> TYPE: DNA
<213> ORGANISM: H. sapiens
<220> FEATURE:

<400> SEQUENCE: 412
aaccagatct acacctggac                                              20

<210> SEQ ID NO 413
<211> LENGTH: 20
<212> TYPE: DNA
<213> ORGANISM: H. sapiens
<220> FEATURE:

<400> SEQUENCE: 413
ccaggtctat aagccaataa                                              20

<210> SEQ ID NO 414
<211> LENGTH: 20
<212> TYPE: DNA
<213> ORGANISM: R. norvegicus
<220> FEATURE:

<400> SEQUENCE: 414
atggagaagc tactatggtg                                              20

<210> SEQ ID NO 415
<211> LENGTH: 20
<212> TYPE: DNA
<213> ORGANISM: R. norvegicus
<220> FEATURE:

<400> SEQUENCE: 415
tcttctgatc acgataagct                                              20

<210> SEQ ID NO 416
<211> LENGTH: 20
<212> TYPE: DNA
<213> ORGANISM: R. norvegicus
<220> FEATURE:

<400> SEQUENCE: 416
tctctcaggc ttttggtcat                                              20

<210> SEQ ID NO 417
<211> LENGTH: 20
<212> TYPE: DNA
<213> ORGANISM: R. norvegicus
<220> FEATURE:

<400> SEQUENCE: 417
gaagacatgt ctaaacaggc                                              20

-continued

<210> SEQ ID NO 418
<211> LENGTH: 20
<212> TYPE: DNA
<213> ORGANISM: R. norvegicus
<220> FEATURE:

<400> SEQUENCE: 418
cttcgtattt cccggagtgt                                          20

<210> SEQ ID NO 419
<211> LENGTH: 20
<212> TYPE: DNA
<213> ORGANISM: R. norvegicus
<220> FEATURE:

<400> SEQUENCE: 419
cagctactgc ctatgtgtcc                                          20

<210> SEQ ID NO 420
<211> LENGTH: 20
<212> TYPE: DNA
<213> ORGANISM: R. norvegicus
<220> FEATURE:

<400> SEQUENCE: 420
ctggaagcag agtcaaagaa                                          20

<210> SEQ ID NO 421
<211> LENGTH: 20
<212> TYPE: DNA
<213> ORGANISM: R. norvegicus
<220> FEATURE:

<400> SEQUENCE: 421
gccactggaa gccttcactg                                          20

<210> SEQ ID NO 422
<211> LENGTH: 20
<212> TYPE: DNA
<213> ORGANISM: R. norvegicus
<220> FEATURE:

<400> SEQUENCE: 422
tgtgtctcta tgcccacgct                                          20

<210> SEQ ID NO 423
<211> LENGTH: 20
<212> TYPE: DNA
<213> ORGANISM: R. norvegicus
<220> FEATURE:

<400> SEQUENCE: 423
catcttctct tacgctacca                                          20

<210> SEQ ID NO 424
<211> LENGTH: 20
<212> TYPE: DNA
<213> ORGANISM: R. norvegicus
<220> FEATURE:

<400> SEQUENCE: 424
agacgagctt taacgagatt                                          20

<210> SEQ ID NO 425

-continued

```
<211> LENGTH: 20
<212> TYPE: DNA
<213> ORGANISM: R. norvegicus
<220> FEATURE:

<400> SEQUENCE: 425
tcaagggttt agtattgcag                                        20

<210> SEQ ID NO 426
<211> LENGTH: 20
<212> TYPE: DNA
<213> ORGANISM: R. norvegicus
<220> FEATURE:

<400> SEQUENCE: 426
taggtgggcc tgaaatactg                                        20

<210> SEQ ID NO 427
<211> LENGTH: 20
<212> TYPE: DNA
<213> ORGANISM: R. norvegicus
<220> FEATURE:

<400> SEQUENCE: 427
ttcagtgctt cagaaattcc                                        20

<210> SEQ ID NO 428
<211> LENGTH: 20
<212> TYPE: DNA
<213> ORGANISM: R. norvegicus
<220> FEATURE:

<400> SEQUENCE: 428
tctgcagaag ggctacattg                                        20

<210> SEQ ID NO 429
<211> LENGTH: 20
<212> TYPE: DNA
<213> ORGANISM: R. norvegicus
<220> FEATURE:

<400> SEQUENCE: 429
tggggacaaa tgcaagcatc                                        20

<210> SEQ ID NO 430
<211> LENGTH: 20
<212> TYPE: DNA
<213> ORGANISM: R. norvegicus
<220> FEATURE:

<400> SEQUENCE: 430
ctcgtatggc ggtggctttg                                        20

<210> SEQ ID NO 431
<211> LENGTH: 20
<212> TYPE: DNA
<213> ORGANISM: R. norvegicus
<220> FEATURE:

<400> SEQUENCE: 431
ggagacattg gagatgtgaa                                        20

<210> SEQ ID NO 432
<211> LENGTH: 20
<212> TYPE: DNA
```

```
<213> ORGANISM: R. norvegicus
<220> FEATURE:

<400> SEQUENCE: 432
catgtgggac tttgtgctat                                               20

<210> SEQ ID NO 433
<211> LENGTH: 20
<212> TYPE: DNA
<213> ORGANISM: R. norvegicus
<220> FEATURE:

<400> SEQUENCE: 433
ctccagaaca gatcaatgca                                               20

<210> SEQ ID NO 434
<211> LENGTH: 20
<212> TYPE: DNA
<213> ORGANISM: R. norvegicus
<220> FEATURE:

<400> SEQUENCE: 434
gtctatgttg gtagggtatt                                               20

<210> SEQ ID NO 435
<211> LENGTH: 20
<212> TYPE: DNA
<213> ORGANISM: R. norvegicus
<220> FEATURE:

<400> SEQUENCE: 435
gttttgaact ggcgggcact                                               20

<210> SEQ ID NO 436
<211> LENGTH: 20
<212> TYPE: DNA
<213> ORGANISM: R. norvegicus
<220> FEATURE:

<400> SEQUENCE: 436
gaagtatgaa acacacggtg                                               20

<210> SEQ ID NO 437
<211> LENGTH: 20
<212> TYPE: DNA
<213> ORGANISM: R. norvegicus
<220> FEATURE:

<400> SEQUENCE: 437
ctgtggccct tgactgactg                                               20

<210> SEQ ID NO 438
<211> LENGTH: 20
<212> TYPE: DNA
<213> ORGANISM: R. norvegicus
<220> FEATURE:

<400> SEQUENCE: 438
tgactgactg ttgtgagtcc                                               20

<210> SEQ ID NO 439
<211> LENGTH: 2305
<212> TYPE: DNA
<213> ORGANISM: O. cuniculus
<220> FEATURE:
```

```
<221> NAME/KEY: CDS
<222> LOCATION: (82)...(759)

<400> SEQUENCE: 439
cctgagcctt cagccagaga cgttttctcc aaaggagtgg attctgagcc tgctcggtag      60
cactggtggc agggagtgac c atg gag aag ctg ctg tgg tgt ttc ctg atc      111
                        Met Glu Lys Leu Leu Trp Cys Phe Leu Ile
                         1               5                  10 ttg gtc agc ttc tct aat atg tct gac cag gca ggc atg cac aag aag      159
Leu Val Ser Phe Ser Asn Met Ser Asp Gln Ala Gly Met His Lys Lys
             15                  20                  25 gcc ttt gtg ttc ccc aaa gag tca gat aat tcc tac gtg tcc ctc aac      207
Ala Phe Val Phe Pro Lys Glu Ser Asp Asn Ser Tyr Val Ser Leu Asn
         30                  35                  40 gca cag tta aag aag cca ctc aaa gcc ttc act gtg tgc ctc tac ttc      255
Ala Gln Leu Lys Lys Pro Leu Lys Ala Phe Thr Val Cys Leu Tyr Phe
     45                  50                  55 tac act gat ctg tcc atg act cgt ggg tac agt att ttc tcc tat gcc      303
Tyr Thr Asp Leu Ser Met Thr Arg Gly Tyr Ser Ile Phe Ser Tyr Ala
 60                  65                  70 acc agg aga caa ttt aac gag atc ctc ctg ttt tgg tcc aag gac ata      351
Thr Arg Arg Gln Phe Asn Glu Ile Leu Leu Phe Trp Ser Lys Asp Ile
 75                  80                  85                  90 gga tat agt ttt tca gtg ggt gga gat gaa ata ata ttc aag gtt tct      399
Gly Tyr Ser Phe Ser Val Gly Gly Asp Glu Ile Ile Phe Lys Val Ser
                 95                 100                 105 gac gtc cct gtg gat cca act cac ctc tgt gca agc tgg gag tcc agc      447
Asp Val Pro Val Asp Pro Thr His Leu Cys Ala Ser Trp Glu Ser Ser
             110                 115                 120 aca ggc att gca gag ctc tgg gta gat ggg aag ccc atg gtg agg aag      495
Thr Gly Ile Ala Glu Leu Trp Val Asp Gly Lys Pro Met Val Arg Lys
         125                 130                 135 agt ctg aag aag ggc tac att ttg ggg cca gag gca agc att att ctg      543
Ser Leu Lys Lys Gly Tyr Ile Leu Gly Pro Glu Ala Ser Ile Ile Leu
     140                 145                 150 ggg cag gat cag gat tcg ttt ggt gga agc ttt gag aaa caa cag tct      591
Gly Gln Asp Gln Asp Ser Phe Gly Gly Ser Phe Glu Lys Gln Gln Ser
155                 160                 165                 170 ttg gtt gga gac att gga aat gtg aac atg tgg gac tat gca ctt tca      639
Leu Val Gly Asp Ile Gly Asn Val Asn Met Trp Asp Tyr Ala Leu Ser
                 175                 180                 185 cca gaa gag att aat acc gtc tat gct ggt ggg acc ttt agt ccc aat      687
Pro Glu Glu Ile Asn Thr Val Tyr Ala Gly Gly Thr Phe Ser Pro Asn
             190                 195                 200 gtc cta gac tgg cgc gag ctg aca tat caa gta cgt ggt gaa gta cat      735
Val Leu Asp Trp Arg Glu Leu Thr Tyr Gln Val Arg Gly Glu Val His
         205                 210                 215 gtc aag ccc cag cta tgg ccc tga gctctgccaa ggatcctgaa ggtgcttctt      789
Val Lys Pro Gln Leu Trp Pro *
     220                 225 gggggttacaa ctcacaggcc ccatacttct ggctgtggac ctttacccccc acatatactg    849 aatgcctgct acataaacag cttcctagct tgccttctt caacaccaga gaatacaaat      909
taaatatctg aggatcttgt ggactacatt gagaagcttt gtccagaaga atcacaattg     969
cagatgtttt ggcttttatt tttatttttt aagctgaaaa gatcttaaag ataatccttt    1029
attttgctaa gatgagaaag ttgacgccta gaaaggagaa ggagaagtga cttttaagtc    1089
acaagacagg ttcaccactt aactgggaag aggacattgg tcttctgtct aactccctac    1149
```

-continued

```
ctaggatagc ccaccacccc cagagagtag aaggtagttg cccacattca cagggctatt    1209
cactctcaga attaggctat cagctaggac tgctggtttc agagttcaca gtgctcattc    1269
taccttggaa ccagtggtcc cagtcttctg aaatagaaga tccagcaata ctgtgccatt    1329
cttccacttt ctcaaagtcc cccagaaagg caaccagaat tgccttagag agaaggcttg    1389
ccttttttct cctgggcaaa agtggcatct gggtatagtc aagaaatcag gtaacagggg    1449
tgtttgcttg cttatattgc tttcttaaca ccatggtttt tctgggatac ccttccccca    1509
ctccctgtgt ggtactctga ccttttcctc cactcccaca tacccaacat attcaggcca    1569
caagagtcag ggtgagactc aggctgtcct aaccagagta gtccatctct ccatggatgg    1629
ctgtatgttg ctagcaggag caattacaga ctctccccag ggattcagtg tggactctgg    1689
ggataagacg tcatctttca gctggaattc taaccttaga aggcatgaac ctggggccac    1749
ctgcagctat cttgttgacc atgtggaggg agatggagaa gaaaaaagcc aagctggaag    1809
agctgagagc ttgacagagt ggtggaatct ggaccatagt gaggctttga gtcagccttg    1869
catggaacca aatctatacc tggacttcct gggtctgtga ctaatatagc tcttggttac    1929
ctgggtgaat ttgagctgtt ttctgatggt tgcattagag gtctgactat cttatttatg    1989
ggcactctga aaccaagtcc ctgtgagctc agactgacca ttgctgtcct tgcaagggag    2049
agtccgtggc actctaatct catctggagt ctcctgcaag gattcttgct gacaagtata    2109
gccctctttg ggaacaatta gtcattcgtg tggggccagt tgtgggggtc ttaatgctct    2169
tattctatca tgattccagt ttgagaaaaa aataaagatc cttgagaagc tcaaatctgc    2229
tgtcatggtc aatgactata aagcactcac ccagtttgtt tgttgtagaa acagactcct    2289
caaaggtaag ggcttt                                                   2305
```

```
<210> SEQ ID NO 440
<211> LENGTH: 19
<212> TYPE: DNA
<213> ORGANISM: Artificial Sequence
<220> FEATURE:
<223> OTHER INFORMATION: PCR Primer

<400> SEQUENCE: 440
ggcgcgagct gacatatca                                                   19

<210> SEQ ID NO 441
<211> LENGTH: 18
<212> TYPE: DNA
<213> ORGANISM: Artificial Sequence
<220> FEATURE:
<223> OTHER INFORMATION: PCR Primer

<400> SEQUENCE: 441
cttggcagag ctcagggc                                                    18

<210> SEQ ID NO 442
<211> LENGTH: 29
<212> TYPE: DNA
<213> ORGANISM: Artificial Sequence
<220> FEATURE:
<223> OTHER INFORMATION: PCR Probe

<400> SEQUENCE: 442
tacgtggtga agtacatgtc aagccccag                                        29

<210> SEQ ID NO 443
<211> LENGTH: 18
```

```
<212> TYPE: DNA
<213> ORGANISM: Artificial Sequence
<220> FEATURE:
<223> OTHER INFORMATION: PCR Primer

<400> SEQUENCE: 443
tccacatggc ctccaagg                                                 18

<210> SEQ ID NO 444
<211> LENGTH: 19
<212> TYPE: DNA
<213> ORGANISM: Artificial Sequence
<220> FEATURE:
<223> OTHER INFORMATION: PCR Primer

<400> SEQUENCE: 444
tcctctggtg ctctcgctg                                                19

<210> SEQ ID NO 445
<211> LENGTH: 22
<212> TYPE: DNA
<213> ORGANISM: Artificial Sequence
<220> FEATURE:
<223> OTHER INFORMATION: PCR Probe

<400> SEQUENCE: 445
aagagccctc aaaccaccgg cc                                            22

<210> SEQ ID NO 446
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 446
cgtctctggc tgaaggctca                                               20

<210> SEQ ID NO 447
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 447
ggctcagaat ccactccttt                                               20

<210> SEQ ID NO 448
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 448
gccaccagtg ctaccgagca                                               20

<210> SEQ ID NO 449
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 449
```

```
cttctccatg gtcactccct                                          20

<210> SEQ ID NO 450
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 450
catgcctgcc tggtcagaca                                          20

<210> SEQ ID NO 451
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 451
gacacgtagg aattatctga                                          20

<210> SEQ ID NO 452
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 452
tctttaactg tgcgttgagg                                          20

<210> SEQ ID NO 453
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 453
gtgtagaagt agaggcacac                                          20

<210> SEQ ID NO 454
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 454
cacgagtcat ggacagatca                                          20

<210> SEQ ID NO 455
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 455
actatatcct atgtccttgg                                          20

<210> SEQ ID NO 456
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 456
gaatattatt tcatctccac                                               20

<210> SEQ ID NO 457
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 457
tcccagcttg cacagaggtg                                               20

<210> SEQ ID NO 458
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 458
ctgcaatgcc tgtgctggac                                               20

<210> SEQ ID NO 459
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 459
cttcccatct acccagagct                                               20

<210> SEQ ID NO 460
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 460
gcccttcttc agactcttcc                                               20

<210> SEQ ID NO 461
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 461
cccagaataa tgcttgcctc                                               20

<210> SEQ ID NO 462
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 462
atgttcacat ttccaatgtc                                               20
```

<210> SEQ ID NO 463
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 463
gtgaaagtgc atagtcccac                                           20

<210> SEQ ID NO 464
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 464
ctaaaggtcc caccagcata                                           20

<210> SEQ ID NO 465
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 465
caagaagcac cttcaggatc                                           20

<210> SEQ ID NO 466
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 466
ggtccacagc cagaagtatg                                           20

<210> SEQ ID NO 467
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 467
tagcaggcat tcagtatatg                                           20

<210> SEQ ID NO 468
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 468
caatgtagtc cacaagatcc                                           20

<210> SEQ ID NO 469
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 469
accaatgtcc tcttcccagt                                               20

<210> SEQ ID NO 470
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 470
gtgaatgtgg gcaactacct                                               20

<210> SEQ ID NO 471
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 471
ttctgagagt gaatagccct                                               20

<210> SEQ ID NO 472
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 472
agtcctagct gatagcctaa                                               20

<210> SEQ ID NO 473
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 473
agaatgagca ctgtgaactc                                               20

<210> SEQ ID NO 474
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 474
gcaagccttc tctctaaggc                                               20

<210> SEQ ID NO 475
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 475
tgactatacc cagatgccac                                               20

<210> SEQ ID NO 476

-continued

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 476
cctgactctt gtggcctgaa                                                  20

<210> SEQ ID NO 477
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 477
taggacagcc tgagtctcac                                                  20

<210> SEQ ID NO 478
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 478
gagagatgga ctactctggt                                                  20

<210> SEQ ID NO 479
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 479
gcaacataca gccatccatg                                                  20

<210> SEQ ID NO 480
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 480
gtctgtaatt gctcctgcta                                                  20

<210> SEQ ID NO 481
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 481
acgtcttatc cccagagtcc                                                  20

<210> SEQ ID NO 482
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 482
```

```
tggtcaacaa gatagctgca                                              20

<210> SEQ ID NO 483
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 483
agctctcagc tcttccagct                                              20

<210> SEQ ID NO 484
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 484
cagattccac cactctgtca                                              20

<210> SEQ ID NO 485
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 485
caggaagtcc aggtatagat                                              20

<210> SEQ ID NO 486
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 486
agctatatta gtcacagacc                                              20

<210> SEQ ID NO 487
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 487
cctctaatgc aaccatcaga                                              20

<210> SEQ ID NO 488
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 488
atggtcagtc tgagctcaca                                              20

<210> SEQ ID NO 489
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 489
tgccacggac tctcccttgc                                               20

<210> SEQ ID NO 490
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 490
ccttgcagga gactccagat                                               20

<210> SEQ ID NO 491
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 491
tgaccatgac agcagatttg                                               20

<210> SEQ ID NO 492
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 492
gtctctggct gaaggctcag                                               20

<210> SEQ ID NO 493
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 493
ccagaataat gcttgcctct                                               20

<210> SEQ ID NO 494
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 494
cagaatccac tcctttggag                                               20

<210> SEQ ID NO 495
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 495
gtcactccct gccaccagtg                                               20
```

```
<210> SEQ ID NO 496
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 496
accacagcag cttctccatg                                               20

<210> SEQ ID NO 497
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 497
tattagagaa gctgaccaag                                               20

<210> SEQ ID NO 498
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 498
ccttcttgtg catgcctgcc                                               20

<210> SEQ ID NO 499
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 499
agtgaaggct ttgagtggct                                               20

<210> SEQ ID NO 500
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 500
gaggatctcg ttaaattgtc                                               20

<210> SEQ ID NO 501
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 501
atttcatctc cacccactga                                               20

<210> SEQ ID NO 502
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 502
cacagaggtg agttggatcc					20

<210> SEQ ID NO 503
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 503
tgtgctggac tcccagcttg					20

<210> SEQ ID NO 504
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 504
acccagagct ctgcaatgcc					20

<210> SEQ ID NO 505
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 505
tgtagccctt cttcagactc					20

<210> SEQ ID NO 506
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 506
aacgaatcct gatcctgccc					20

<210> SEQ ID NO 507
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 507
gacggtatta atctcttctg					20

<210> SEQ ID NO 508
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 508
cccaagaagc accttcagga					20

```
<210> SEQ ID NO 509
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 509
gctgtttatg tagcaggcat                                                    20

<210> SEQ ID NO 510
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 510
ctctggtgtt gaagaaggca                                                    20

<210> SEQ ID NO 511
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 511
ctaggcgtca actttctcat                                                    20

<210> SEQ ID NO 512
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 512
tgacttaaaa gtcacttctc                                                    20

<210> SEQ ID NO 513
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 513
taagtggtga acctgtcttg                                                    20

<210> SEQ ID NO 514
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 514
tagacagaag accaatgtcc                                                    20

<210> SEQ ID NO 515
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 515
gcaactacct tctactctct                                                   20

<210> SEQ ID NO 516
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 516
gatagcctaa ttctgagagt                                                   20

<210> SEQ ID NO 517
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 517
atcttctatt tcagaagact                                                   20

<210> SEQ ID NO 518
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 518
agaatggcac agtattgctg                                                   20

<210> SEQ ID NO 519
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 519
cagatgccac ttttgcccag                                                   20

<210> SEQ ID NO 520
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 520
atataagcaa gcaaacaccc                                                   20

<210> SEQ ID NO 521
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 521
tgagtctcac cctgactctt                                                   20

<210> SEQ ID NO 522
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 522
gccatccatg gagagatgga                                              20

<210> SEQ ID NO 523
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 523
gctcctgcta gcaacataca                                              20

<210> SEQ ID NO 524
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 524
cccagagtcc acactgaatc                                              20

<210> SEQ ID NO 525
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 525
cccaggttca tgccttctaa                                              20

<210> SEQ ID NO 526
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 526
cttctccatc tccctccaca                                              20

<210> SEQ ID NO 527
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 527
ttggttccat gcaaggctga                                              20

<210> SEQ ID NO 528
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 528
```

```
gtcacagacc caggaagtcc                                          20

<210> SEQ ID NO 529
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 529
ttcacccagg taaccaagag                                          20

<210> SEQ ID NO 530
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 530
gatagtcaga cctctaatgc                                          20

<210> SEQ ID NO 531
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 531
tctcccttgc aaggacagca                                          20

<210> SEQ ID NO 532
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 532
gagattagag tgccacggac                                          20

<210> SEQ ID NO 533
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 533
cagcaagaat ccttgcagga                                          20

<210> SEQ ID NO 534
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 534
cccacacgaa tgactaattg                                          20

<210> SEQ ID NO 535
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 535
gaataagagc attaagaccc                                               20

<210> SEQ ID NO 536
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 536
agcagatttg agcttctcaa                                               20

<210> SEQ ID NO 537
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 537
gaggagtctg tttctacaac                                               20

<210> SEQ ID NO 538
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 538
ccttaccttt gaggagtctg                                               20

<210> SEQ ID NO 539
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 539
aagcccttac ctttgaggag                                               20

<210> SEQ ID NO 540
<211> LENGTH: 1614
<212> TYPE: DNA
<213> ORGANISM: M. musculus
<220> FEATURE:
<221> NAME/KEY: CDS
<222> LOCATION: (82)...(759)

<400> SEQUENCE: 540
aggcgttcca ggactccttg tccttgatct ttcagacaaa acactgtcct cttagtccag    60
atcccagcag catccatagc c atg gag aag cta ctc tgg tgc ctt ctg atc    111
                        Met Glu Lys Leu Leu Trp Cys Leu Leu Ile
                         1               5                  10 atg atc agc ttc tct cgg act ttt ggt cat gaa gac atg ttt aaa aag    159
Met Ile Ser Phe Ser Arg Thr Phe Gly His Glu Asp Met Phe Lys Lys
             15                  20                  25 gcc ttt gta ttt ccc aag gag tca gat act tcc tat gtg tct ctg gaa    207
Ala Phe Val Phe Pro Lys Glu Ser Asp Thr Ser Tyr Val Ser Leu Glu
         30                  35                  40
```

```
gca gag tca aag aag cca ctg aac acc ttt act gtg tgt ctc cat ttc      255
Ala Glu Ser Lys Lys Pro Leu Asn Thr Phe Thr Val Cys Leu His Phe
             45                  50                  55 tac act gct ctg agc aca gtg cgc agc ttc agt gtc ttc tct tat gct      303
Tyr Thr Ala Leu Ser Thr Val Arg Ser Phe Ser Val Phe Ser Tyr Ala
         60                  65                  70 acc aag aag aac tct aac gac att ctc ata ttt tgg aat aag gat aaa      351
Thr Lys Lys Asn Ser Asn Asp Ile Leu Ile Phe Trp Asn Lys Asp Lys
 75                  80                  85                  90 cag tat act ttt gga gtg ggt ggt gct gaa gta cga ttc atg gtt tca      399
Gln Tyr Thr Phe Gly Val Gly Gly Ala Glu Val Arg Phe Met Val Ser
                 95                 100                 105 gag att cct gag gct cca aca cac atc tgt gcc agc tgg gag tct gct      447
Glu Ile Pro Glu Ala Pro Thr His Ile Cys Ala Ser Trp Glu Ser Ala
            110                 115                 120 acg ggg att gta gag ttc tgg att gat ggg aaa ccc aag gtg cgg aaa      495
Thr Gly Ile Val Glu Phe Trp Ile Asp Gly Lys Pro Lys Val Arg Lys
        125                 130                 135 agt ctg cac aag ggc tac act gtg ggg cca gat gca agc atc atc ttg      543
Ser Leu His Lys Gly Tyr Thr Val Gly Pro Asp Ala Ser Ile Ile Leu
    140                 145                 150 ggg cag gag cag gac tcg tat ggc ggt gac ttt gat gca aag cag tct      591
Gly Gln Glu Gln Asp Ser Tyr Gly Gly Asp Phe Asp Ala Lys Gln Ser
155                 160                 165                 170 ttg gtg gga gac atc gga gat gtg aac atg tgg gat ttt gtg cta tct      639
Leu Val Gly Asp Ile Gly Asp Val Asn Met Trp Asp Phe Val Leu Ser
                175                 180                 185 cca gaa cag atc aac aca gtc tat gtt ggt ggg aca ctc agc ccc aat      687
Pro Glu Gln Ile Asn Thr Val Tyr Val Gly Gly Thr Leu Ser Pro Asn
            190                 195                 200 gtt ttg aac tgg cgg gca ctg aac tat aaa gca cag ggt gat gtg ttt      735
Val Leu Asn Trp Arg Ala Leu Asn Tyr Lys Ala Gln Gly Asp Val Phe
        205                 210                 215 att aag ccg cag ctg tgg tcc tga cctactgttg tgaaccctga agcacctcct    789
Ile Lys Pro Gln Leu Trp Ser *
    220                 225 gggattacat tctctccctt gtctcgggtt atgaaccttt tagccccagc agatgttgta    849
ggtctgttct gtgaatatgg cctttcactt ctctgctttg tggtcctcag cactagagca    909
cggaatttaa atggaaggct tccagcataa gcatcccact aggactctac caaagagaat    969
ctgacttacc catggtttta tatatatatg taaatatcca tatatatata tatatgcata   1029
tatatatata tataattgaa aaaatttcag acataattct tctccctcac atagatgaga   1089
aaatagatgc acagaaagga gaataatttt ttattgtttt tgttttataa tgtcatcttg   1149
agtgctgtat ttacatactt tctatccctc cctcttcaga tcctttccta tccttccaaa   1209
ttctctctca aattcatgat gtcttattat tagtcttatg catatataca tatgcataat   1269
acctatcatc tatcaatcaa tctatctacc tatctatcat ctattcatca gtcatccatc   1329
ttactgatta catttagtgc ttcttgtatt ttgttgaaga ctggacactg gataatctat   1389
caggagggcc cctccctgaa gactgattgt ccttttctca gcagccactg attacctcta   1449
gctcttcata tagggttctg tctttgtgaa atttcttctg tccatgttgc atgtcaattg   1509
gtgtcattat gcaggtcttg tttgggcaac ctagagtgat ggagcactga ctacactgtg   1569
ctcagaatca gttctttct ggaataaaat ctgtacctga acttc                     1614

<210> SEQ ID NO 541
```

```
<211> LENGTH: 20
<212> TYPE: DNA
<213> ORGANISM: Artificial Sequence
<220> FEATURE:
<223> OTHER INFORMATION: PCR Primer

<400> SEQUENCE: 541
tggattgatg ggaaacccaa                                                20

<210> SEQ ID NO 542
<211> LENGTH: 18
<212> TYPE: DNA
<213> ORGANISM: Artificial Sequence
<220> FEATURE:
<223> OTHER INFORMATION: PCR Primer

<400> SEQUENCE: 542
gcatctggcc ccacagtg                                                  18

<210> SEQ ID NO 543
<211> LENGTH: 23
<212> TYPE: DNA
<213> ORGANISM: Artificial Sequence
<220> FEATURE:
<223> OTHER INFORMATION: PCR Probe

<400> SEQUENCE: 543
tgcggaaaag tctgcacaag ggc                                            23

<210> SEQ ID NO 544
<211> LENGTH: 20
<212> TYPE: DNA
<213> ORGANISM: Artificial Sequence
<220> FEATURE:
<223> OTHER INFORMATION: PCR Primer

<400> SEQUENCE: 544
ggcaaattca acggcacagt                                                20

<210> SEQ ID NO 545
<211> LENGTH: 20
<212> TYPE: DNA
<213> ORGANISM: Artificial Sequence
<220> FEATURE:
<223> OTHER INFORMATION: PCR Primer

<400> SEQUENCE: 545
gggtctcgct cctggaagat                                                20

<210> SEQ ID NO 546
<211> LENGTH: 27
<212> TYPE: DNA
<213> ORGANISM: Artificial Sequence
<220> FEATURE:
<223> OTHER INFORMATION: PCR Probe

<400> SEQUENCE: 546
aaggccgaga atgggaagct tgtcatc                                        27

<210> SEQ ID NO 547
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 547
```

```
tttgtctgaa agatcaagga                                              20

<210> SEQ ID NO 548
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 548
aggacagtgt tttgtctgaa                                              20

<210> SEQ ID NO 549
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 549
cttctccatg gctatggatg                                              20

<210> SEQ ID NO 550
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 550
accagagtag cttctccatg                                              20

<210> SEQ ID NO 551
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 551
agtaaaggtg ttcagtggct                                              20

<210> SEQ ID NO 552
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 552
ttagagttct tcttggtagc                                              20

<210> SEQ ID NO 553
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 553
gaatcgtact tcagcaccac                                              20

<210> SEQ ID NO 554
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 554
cacagatgtg tgttggagcc                                                    20

<210> SEQ ID NO 555
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 555
ctacaatccc cgtagcagac                                                    20

<210> SEQ ID NO 556
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 556
cctgccccaa gatgatgctt                                                    20

<210> SEQ ID NO 557
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 557
ctgagtgtcc caccaacata                                                    20

<210> SEQ ID NO 558
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 558
catcaccctg tgctttatag                                                    20

<210> SEQ ID NO 559
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 559
gtcaggacca cagctgcggc                                                    20

<210> SEQ ID NO 560
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 560
ttcagggttc acaacagtag                                                    20
```

-continued

<210> SEQ ID NO 561
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 561
aatgtaatcc caggaggtgc                                                 20

<210> SEQ ID NO 562
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 562
gtgctctagt gctgaggacc                                                 20

<210> SEQ ID NO 563
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 563
ctcctttctg tgcatctatt                                                 20

<210> SEQ ID NO 564
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 564
agatgatagg tattatgcat                                                 20

<210> SEQ ID NO 565
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 565
ccagtgtcca gtcttcaaca                                                 20

<210> SEQ ID NO 566
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 566
gggccctcct gatagattat                                                 20

<210> SEQ ID NO 567
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 567
gtaatcagtg gctgctgaga                                                 20

<210> SEQ ID NO 568
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 568
acagaaccct atatgaagag                                                 20

<210> SEQ ID NO 569
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 569
agacctgcat aatgacacca                                                 20

<210> SEQ ID NO 570
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 570
gcacagtgta gtcagtgctc                                                 20

<210> SEQ ID NO 571
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 571
caaggagtcc tggaacgcct                                                 20

<210> SEQ ID NO 572
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 572
ctggactaag aggacagtgt                                                 20

<210> SEQ ID NO 573
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 573
agctgatcat gatcagaagg                                                 20

```
<210> SEQ ID NO 574
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 574
tgcttccaga gacacatagg                                               20

<210> SEQ ID NO 575
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 575
gtgtagaaat ggagacacac                                               20

<210> SEQ ID NO 576
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 576
ataagagaag acactgaagc                                               20

<210> SEQ ID NO 577
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 577
ccacagtgta gcccttgtgc                                               20

<210> SEQ ID NO 578
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 578
gatgatgctt gcatctggcc                                               20

<210> SEQ ID NO 579
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 579
tacgagtcct gctcctgccc                                               20

<210> SEQ ID NO 580
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 580
gactgctttg catcaaagtc                                              20

<210> SEQ ID NO 581
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 581
tgctttatag ttcagtgccc                                              20

<210> SEQ ID NO 582
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 582
taacccgaga caagggagag                                              20

<210> SEQ ID NO 583
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 583
cagaacagac ctacaacatc                                              20

<210> SEQ ID NO 584
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 584
gaagtgaaag gccatattca                                              20

<210> SEQ ID NO 585
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 585
tagtgggatg cttatgctgg                                              20

<210> SEQ ID NO 586
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 586
aatacagcac tcaagatgac                                              20

<210> SEQ ID NO 587
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 587
ataggaaagg atctgaagag                                                20

<210> SEQ ID NO 588
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 588
catcatgaat ttgagagaga                                                20

<210> SEQ ID NO 589
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 589
aggtagatag attgattgat                                                20

<210> SEQ ID NO 590
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 590
ctgatgaata gatgatagat                                                20

<210> SEQ ID NO 591
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 591
gtaatcagta agatggatga                                                20

<210> SEQ ID NO 592
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 592
ccctcctgat agattatcca                                                20

<210> SEQ ID NO 593
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 593
```
cataatgaca ccaattgaca 20

<210> SEQ ID NO 594
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 594
ggttgcccaa acaagacctg 20

<210> SEQ ID NO 595
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 595
gtcagtgctc catcactcta 20

<210> SEQ ID NO 596
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 596
ctgattctga gcacagtgta 20

<210> SEQ ID NO 597
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 597
ctcttactgt gctgtggaca 20

<210> SEQ ID NO 598
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 598
tcccatttca ggagacctg 19

<210> SEQ ID NO 599
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 599
cccatttcag gagacctgg 19

<210> SEQ ID NO 600
<211> LENGTH: 19
<212> TYPE: DNA
<213> ORGANISM: Artificial Sequence

```
<220> FEATURE:
<223> OTHER INFORMATION: Antisense Oligonucleotide

<400> SEQUENCE: 600
gcactctgga cccaaacca                                                19

<210> SEQ ID NO 601
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 601
cactctggac ccaaaccag                                                19

<210> SEQ ID NO 602
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 602
tcccatttca ggagacct                                                 18

<210> SEQ ID NO 603
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 603
cccatttcag gagacctg                                                 18

<210> SEQ ID NO 604
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 604
ccatttcagg agacctgg                                                 18

<210> SEQ ID NO 605
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 605
gcactctgga cccaaacc                                                 18

<210> SEQ ID NO 606
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 606
actctggacc caaaccag                                                 18
```

```
<210> SEQ ID NO 607
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 607
cactctggac ccaaacca                                                    18

<210> SEQ ID NO 608
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 608
ccatttcagg agacct                                                      16

<210> SEQ ID NO 609
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 609
actctggacc caaacc                                                      16

<210> SEQ ID NO 610
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 610
tcccatttca ggaga                                                       15

<210> SEQ ID NO 611
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 611
tttcaggaga cctgg                                                       15

<210> SEQ ID NO 612
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 612
gcactctgga cccaa                                                       15

<210> SEQ ID NO 613
<211> LENGTH: 15
<212> TYPE: DNA
<213> ORGANISM: Artificial Sequence
<220> FEATURE:
<223> OTHER INFORMATION: Antisense Oligonucleotide
```

```
<400> SEQUENCE: 613
ctggacccaa accag                                                      15

<210> SEQ ID NO 614
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 614
tcccgcctgt gacatgcatt                                                 20

<210> SEQ ID NO 615
<211> LENGTH: 1681
<212> TYPE: DNA
<213> ORGANISM: Macaca fascicularis
<220> FEATURE:
<221> NAME/KEY: misc_feature
<222> LOCATION: 649
<223> OTHER INFORMATION: n = A,T,C or G
<220> FEATURE:
<221> NAME/KEY: misc_feature
<222> LOCATION: 650
<223> OTHER INFORMATION: n = A,T,C or G
<220> FEATURE:
<221> NAME/KEY: misc_feature
<222> LOCATION: 751
<223> OTHER INFORMATION: n = A,T,C or G
<220> FEATURE:
<221> NAME/KEY: misc_feature
<222> LOCATION: 1282
<223> OTHER INFORMATION: n = A,T,C or G
<220> FEATURE:
<221> NAME/KEY: misc_feature
<222> LOCATION: 1517
<223> OTHER INFORMATION: n = A,T,C or G

<400> SEQUENCE: 615
ctctcatatt tgcttgtttt tctggctcac agacatgtcg atgaaggctt ttgtgtttcc      60
caaagagtcg gataattcct atgtaaccct caaagcacgt taacgaagc ctctcaaagc     120 cttcactgtg tgcctccact tctacacaga actgtcctca acccgtgggt acagtatttt    180
ctccttatgc caccaagaga caaaataatg agattctcat attttggtct aaggatatag    240
gatacagttt tacagtgggt gggtctgaaa tattattcga agttcctgaa gtcacagtag    300
ctccagtaca catttgtaca agctgggagt ccgcctcggg gatcgtggag ttctgggtgg    360
atggaaagcc cagggcaagg aagagtctga agaggggata cactgctggg ggaagatgca    420
agcattatct tggggcagga gcaggattcc ttcggtggga gctttgaaac acagcagtcc    480
ctggtgggag acattggaaa tgtgaacatg tgggactttg tgctgtcacc agatgagatt    540
agcaccgtct atcgtggcgg gaccttcagt cctagtgtcc tgtactggcg ggcactgaag    600
tatgaagtgc aaggtgaagt gttcatcaaa ccccagctgt ggtcctgann ccagctgtgg    660
tcctgatggt acctcccggt ttttacacc gcacgcgccc cacgtctctg tctctagtac     720
ctcccggttt ttcacactgc ctggttccca ngtggttgtc tctgggcctt tgttcccctg    780
tatgcattgc aggcctgctc caccctcctc agcacctgag aatggaggta aagtgtctgg    840
tctgggagct cgttaactat gctgggaaac tttgtccaaa agaatcagaa tttgaggtgt    900
tttgttttca ttttattc ttttttaagtt ggacagatct tggagataat gtcttaccct     960
cacatagatg aaaacactga cacccagaaa ggagaaatga tgttttaaaa aatgtcacaa   1020
```

```
ggcaagaact gagaggaagt gctggtcttc tatttaattc cccgcccagg accccagaa    1080 agcaggaggg cattgcccac attcacaggg ctcttcagtc tcagaatcag gacattggcc    1140
aggtctctgg tttgggtcca gagtgctcat gatcatgcca tggaactgct ggacccaggt    1200
ctcctgaaat gggaagccca gcaatactgc acagttcctc cattttctc aaagcacact     1260 ggaaaggccg ttagaattgc cntagcagag aaggtctgct ttttttccag agcagaatga    1320
ggcactaggt ataaatatgt tgttactgcc aagaacttac ataacaatag tttttgtttg    1380
ctcgcagtgc tttcttaatt ttatggctct tctgggaaac tcctccccct ttgcacatga    1440
accttgtggg gctgtgaatt ccttctttaa cccctcattc ccaatatacc caggccacaa    1500
gagtggacat gaaccancag ggtgtcctgt cagagtagcc catctcccat ctccccagct    1560
ccctatctgg aggatagttg atagttatg tgttcccagc aggaccaatt atagcctttc     1620
caaggattga gttatggcct tgggagtga gatatcttct tgctgctgga tttccaagct     1680
g                                                                    1681

<210> SEQ ID NO 616
<211> LENGTH: 374
<212> TYPE: DNA
<213> ORGANISM: Macaca fascicularis

<400> SEQUENCE: 616
gcccctgaac ttttcagccg aatacattct tttccaaagg agtgaattca ggtccttggt     60
atcactggca gcagggcgtg accatggaga agctgttgtg tttcttggtc ttgaccagcc    120
tctctcatgc ttttggccag acagacatgt cgatgaaggc ttttgtgttt cccaaagagt    180
cggaatccag gcaggaggag gtagctctga ggcaagagat ctaggacttc tagcccctga    240
actttcagcc gaatacatct tttccaaagg agtgaattca ggtccttgta tcactggcag    300
cagggcgtga tccatggaga agctgttgtg tttcttggtc ttgaccagcc tctctcatgc    360
ttttggccag acag                                                      374

<210> SEQ ID NO 617
<211> LENGTH: 20
<212> TYPE: DNA
<213> ORGANISM: Artificial Sequence
<220> FEATURE:
<223> OTHER INFORMATION: Antisense Oligonucleotide
<220> FEATURE:
<221> NAME/KEY: misc_feature
<222> LOCATION: 1-20
<223> OTHER INFORMATION: n = A,T,C or G

<400> SEQUENCE: 617
nnnnnnnnnn nnnnnnnnnn                                                 20

<210> SEQ ID NO 618
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 618
ttgtcccagt cccaggcctc                                                 20

<210> SEQ ID NO 619
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 619
gccctccatg ctggcacagg                                              20

<210> SEQ ID NO 620
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 620
agcccattgc tggacatgca                                              20

<210> SEQ ID NO 621
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 621
gcccattgct ggacatgc                                                18

<210> SEQ ID NO 622
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 622
agcaaaagat caatccgtta                                              20

<210> SEQ ID NO 623
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 623
cgtgtgtctg tgctagtccc                                              20

<210> SEQ ID NO 624
<211> LENGTH: 19
<212> TYPE: DNA
<213> ORGANISM: Artificial Sequence
<220> FEATURE:
<223> OTHER INFORMATION: antisense Oligonucleotide

<400> SEQUENCE: 624
cgagaggcgg acgggaccg                                               19

<210> SEQ ID NO 625
<211> LENGTH: 21
<212> TYPE: DNA
<213> ORGANISM: Artificial Sequence
<220> FEATURE:
<223> OTHER INFORMATION: antisense Oligonucleotide

<400> SEQUENCE: 625
cgagaggcgg acgggaccgt t                                            21
```

```
<210> SEQ ID NO 626
<211> LENGTH: 21
<212> TYPE: DNA
<213> ORGANISM: Artificial Sequence
<220> FEATURE:
<223> OTHER INFORMATION: complement Oligonucleotide

<400> SEQUENCE: 626
ttgctctccg cctgccctgg c                                                 21

<210> SEQ ID NO 627
<211> LENGTH: 19
<212> TYPE: DNA
<213> ORGANISM: Artificial Sequence
<220> FEATURE:
<223> OTHER INFORMATION: complement Oligonucleotide

<400> SEQUENCE: 627
gctctccgcc tgccctggc                                                    19
```

MODULATION OF C-REACTIVE PROTEIN EXPRESSION

CROSS-REFERENCE TO RELATED APPLICATIONS

This is a continuation of U.S. application Ser. No. 10/858,500, filed Jun. 1, 2004, U.S. Pat. No. 7,425,545 which claims the benefit of the priority of U.S. Provisional Patent Application No. 60/475,272, filed Jun. 2, 2003, and U.S. Provisional Patent Application No. 60/540,042, filed Jan. 28, 2004, each of which is incorporated herein in its entirety.

BACKGROUND OF THE INVENTION

The present invention provides compositions and methods for modulating the expression of C-reactive protein.

C-reactive protein (also known as CRP and PTX1) is an essential human acute-phase reactant produced in the liver in response to a variety of inflammatory cytokines. The protein, first identified in 1930, is highly conserved and considered to be an early indicator of infectious or inflammatory conditions. Plasma C-reactive protein levels increase 1,000-fold in response to infection, ischemia, trauma, burns, and inflammatory conditions. Since the biological half-life of C-reactive protein is not influenced by age, liver or kidney function or pharmacotherapy, it is a reliable biochemical marker for tissue destruction, necrosis and inflammation and its measurement is widely used to monitor various inflammatory states, angina pectoris, vascular insults, end-stage renal disease, rheumatoid arthritis, obesity and atherosclerosis (Arici and Walls, *Kidney Int.*, 2001, 59, 407-414; Gabay and Kushner, *N. Engl. J. Med.*, 1999, 340, 448-454; Highton et al., *J. Rheumatol.*, 1985, 12, 871-875; Hulthe et al., *Clin Sci (Colch)*, 2001, 100, 371-378; Lagrand et al., *Circulation*, 1999, 100, 6+96-102; Morrow and Ridker, *Med. Clin. North Am.*, 2000, 84, 149-161, ix; Szalai et al., *Immunol Res*, 1997, 16, 127-136; Westhuyzen and Healy, *Ann. Clin. Lab. Sci.*, 2000, 30, 133-143; Yudkin et al., *Atherosclerosis*, 2000, 148, 209-214).

Improved methods of quantifying C-reactive protein have led to increased application to clinical medicine including diagnoses of urinary tract infections (Arici and Walls, 2001, cited above), meningitis (Ruuskanen et al., *J. Pediatr.*, 1985, 107, 97-100), neonatal sepsis, erythropoietin resistance (Barany, *Nephrol. Dial. Transplant.*, 2001, 16, 224-227) and occult bacteremia, conditions in which C-reactive protein is usually elevated.

Structurally, C-reactive protein is a member of the pentraxin family of proteins, which are characterized by a cyclic pentameric structure and radial symmetry. The five identical 24-kDa protomers consist of 206 amino acids, and are non-covalently linked (Lei et al., *J. Biol. Chem.*, 1985, 260, 13377-13383; Szalai et al., 1997, cited above). The genomic DNA sequence for human C-reactive protein has been reported by Lei et al. 1985, cited above, as have mutant forms of the protein (International Patent Publication No. WO 96/06624) and methods to deliver materials into cells using the mutant protein as a carrier (International Patent Publication No. WO 00/11207). Polypeptides corresponding to amino acids 174-185 of C-reactive protein having immunomodulatory activity are disclosed and claimed U.S. Pat. No. 5,783,179. Peptides corresponding to positions 62-71 of human C-reactive protein have also been studied for their ability to inhibit the activity of human leukocyte elastase and/or cathepsin G for the treatment of inflammatory conditions and these are disclosed in International Patent Publication No. WO 99/00418.

C-reactive protein binds to a broad range of cellular substances such as phosphocholine, fibronectin, chromatin, histones, and ribonucleoprotein in a calcium-dependent manner (Szalai et al., 1997, cited above). It is a ligand for specific receptors on phagocytic leukocytes, mediates activation reactions on monocytes and macrophages, and activates complement (Szalai et al., 1997, cited above).

The function of C-reactive protein is related to its role in the innate immune system. Similar to immunoglobulin (Ig) G, it activates complement, binds to Fc receptors and acts as an opsonin for various pathogens. Interaction of C-reactive protein with Fc receptors leads to the generation of proinflammatory cytokines that enhance the inflammatory response. Unlike IgG, which specifically recognizes distinct antigenic epitopes, C-reactive protein recognizes altered self and foreign molecules based on pattern recognition. C-reactive protein is therefore thought to act as a surveillance molecule for altered self and certain pathogens. This recognition provides early defense and leads to a proinflammatory signal and activation of the humoral, adaptive immune system. Thus, the C-reactive protein molecule has both a recognition function and an effector function.

The pharmacological modulation of C-reactive protein activity and/or its expression is therefore an appropriate point of therapeutic intervention in pathological conditions.

Strategies aimed at modulating C-reactive protein function by targeting protein levels have involved the use of antibodies, peptides and molecules that inhibit HMG-CoA reductase.

In a recent trial, it was demonstrated that lovastatin, an inhibitor of the enzyme HMG-CoA reductase, is an effective agent in reducing the risk of acute coronary events in participants with elevated C-reactive protein levels but no hyperlipidemia; the use of lovastatin resulted in a 14.8 percent reduction in median C-reactive protein levels after one year whereas no change was observed in the placebo group (Ridker et al., *N. Engl. J. Med.*, 2001, 344, 1959-1965). Another statin, cerivastatin, has also been demonstrated to lower C-reactive protein levels in patients with hypercholesterolemia (Ridker et al., *Circulation*, 2001, 103, 1191-1193.).

However, there are currently no known therapeutic agents that effectively inhibit C-reactive protein levels and function. Consequently, there remains a long felt need for agents capable of effectively and selectively inhibiting C-reactive protein.

SUMMARY OF THE INVENTION

The present invention provides compositions and methods for modulating C-reactive protein expression.

The present invention is directed to compounds, especially nucleic acid and nucleic acid-like oligomers, which are targeted to a nucleic acid encoding C-reactive protein, and which modulate the expression of C-reactive protein. In particular, this invention relates to compounds, particularly oligonucleotide compounds, which, in preferred embodiments, hybridize with nucleic acid molecules encoding C-reactive protein. Such compounds are shown herein to modulate the expression of C-reactive protein.

Antisense technology is emerging as an effective means for reducing the expression of specific gene products and is uniquely useful in a number of therapeutic, diagnostic, and research applications for the modulation of C-reactive protein expression.

Pharmaceutical and other compositions comprising the compounds of the invention are also provided. Further provided are methods of screening for modulators of C-reactive protein and methods of modulating the expression of C-reactive protein in cells, tissues or animals comprising contacting said cells, tissues or animals with one or more of the compounds or compositions of the invention. In these methods, the cells or tissues may be contacted in vivo. Alternatively, the cells or tissues may be contacted ex vivo.

Methods of treating an animal, particularly a human, suspected of having or being prone to a disease or condition associated with expression of C-reactive protein are also set forth herein. Such methods comprise administering a therapeutically or prophylactically effective amount of one or more of the compounds or compositions of the invention to the person in need of treatment.

In one aspect, the invention provides the use of a compound or composition of the invention in the manufacture of a medicament for the treatment of any and all conditions disclosed herein.

DETAILED DESCRIPTION OF THE INVENTION

A. Overview of the Invention

The present invention employs compounds, preferably oligonucleotides and similar species for use in modulating the function or effect of nucleic acid molecules encoding C-reactive protein. This is accomplished by providing oligonucleotides that specifically hybridize with one or more nucleic acid molecules encoding C-reactive protein. As used herein, the terms "target nucleic acid" and "nucleic acid molecule encoding C-reactive protein" have been used for convenience to encompass DNA encoding C-reactive protein, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of C-reactive protein. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases that pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases that can hydrogen bond with each other. Thus, "specifically hybridizable" and "complementary" are terms that are used to indicate a sufficient degree of precise pairing or complementarity over a sufficient number of nucleobases such that stable and specific binding occurs between the oligonucleotide and a target nucleic acid.

It is understood in the art that the sequence of an antisense compound can be, but need not be, 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, 1981, 2, 482-489). In some embodiments, homology, sequence identity or complementarity, between the oligomeric and target is between about 50% to about 60%. In some embodiments, homology, sequence identity or complementarity, is between about 60% to about 70%. In some embodiments, homology, sequence identity or complementarity, is between about 70% and about 80%. In further embodiments, homology, sequence identity or complementarity, is between about 80% and about 90%. In further embodiments, homology, sequence identity or complementarity, is about 90%, about 92%, about 94%, about 95%, about 96%, about 97%, about 98%, about 99%, or about 100%.

B. Compounds of the Invention

According to the present invention, compounds include antisense oligomeric compounds, antisense oligonucleotides, siRNAs, external guide sequence (EGS) oligonucleotides, alternate splicers and other short oligomeric compounds that hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds that are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of antisense compound is a single-stranded antisense oligonucleotide, in many species the introduction of double-stranded structures, such as double-stranded RNA (dsRNA) molecules, induces potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). The primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, the single-stranded RNA oligomers of antisense polarity of the dsRNAs have been reported to be the potent inducers of RNAi (Tijsterman et al., *Science*, 2002, 295, 694-697).

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

The oligonucleotides of the present invention also include modified oligonucleotides in which a different base is present at one or more of the nucleotide positions in the oligonucleotide. For example, if the first nucleotide is an adenosine, modified oligonucleotides may be produced which contain thymidine, guanosine or cytidine at this position. This may be done at any of the positions of the oligonucleotide. These oligonucleotides are then tested using the methods described herein to determine their ability to inhibit expression of C-reactive protein mRNA.

While oligonucleotides are a preferred form of the compounds of this invention, the present invention comprehends other families of compounds as well, including but not limited to oligonucleotide analogs and mimetics such as those described herein.

The compounds in accordance with this invention comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

In another embodiment, the compounds of the invention are oligonucleotides from about 12 to about 50 nucleobases. Further embodiments are those comprising from about 15 to about 30 nucleobases.

In another embodiment, the antisense compounds comprise at least 8 contiguous nucleobases of an antisense compound disclosed herein.

Antisense compounds 8-80 nucleobases in length comprising a stretch of at least eight (8) consecutive nucleobases selected from within the illustrative antisense compounds are considered to be suitable antisense compounds as well.

Exemplary antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). Exemplary compounds of this invention may be found identified in the Examples and listed in Tables 1, 2 and 3. One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes C-reactive protein.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes, having translation initiation codons with the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding C-reactive protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions of a molecule encoding C-reactive protein that may be targeted effectively with the antisense compounds of the present invention.

The open reading frame (ORF) or "coding region," which is known in the art to refer to the region between the translation initiation codon and the translation termination codon, is also a region of the molecule encoding C-reactive protein that may be targeted effectively. Within the context of the present invention, a preferred region is the intragenic region encompassing the translation initiation or termination codon of the open reading frame (ORF) of a gene.

Other target regions of molecules encoding C-reactive protein include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region of a molecule encoding C-reactive protein.

Accordingly, the present invention provides antisense compounds that target a portion of nucleotides 1-2480 as set forth in SEQ ID NO:4. In another embodiment, the antisense compounds target at least an 8 nucleobase portion of nucleotides 1-570, comprising the 5'UTR as set forth in SEQ ID NO:4. In another embodiment the antisense compounds target at least an 8 nucleobase portion of nucleotides 1183-2480 comprising the 3'UTR as set forth in SEQ ID NO:4. In another embodiment, the antisense compounds target at least an 8 nucleobase portion of nucleotides 571-1182 comprising the coding region as set forth in SEQ ID NO:4. In still other embodiments, the antisense compounds target at least an 8 nucleobase portion of a "preferred target segment" (as defined herein) as set forth in Table 4.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources, known as "fusion transcripts, are also suitable target sites. Introns can be effectively targeted using antisense compounds targeted to, for example, DNA or pre-mRNA.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target C-reactive protein nucleic acid to which the preferred antisense compounds hybridize are hereinbelow referred to as "preferred target segments." As used herein the term "preferred target segment" is defined as at least an 8-nucleobase portion of a target region of a molecule encoding C-reactive protein to which an active antisense compound is targeted. While not wishing to be bound by theory, it is presently believed that these target segments represent portions of the target nucleic acid that are accessible for hybridization.

While the specific sequences of certain preferred C-reactive protein target segments are set forth herein, one of skill in the art will recognize that these serve to illustrate and describe particular embodiments within the scope of the present invention. Additional preferred target segments may be identified by one having ordinary skill in view of this specification.

Target segments 8-80 nucleobases in length comprising a stretch of at least eight (8) consecutive nucleobases selected from within the illustrative preferred target segments of C-reactive protein are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

In one embodiment, the oligomeric antisense compounds can be targeted to regions of a target nucleobase sequence, such as those disclosed herein. All regions of a nucleobase sequence to which an oligomeric antisense compound can be targeted, wherein the regions are greater than or equal to 8 and less than or equal to 80 nucleobases, are described as follows:

Let $R(n, n+m-1)$ be a region from a target nucleobase sequence, where "n" is the 5'-most nucleobase position of the region, where "n+m-1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 8 and is less than or equal to 80.

This set of regions can be represented using the following mathematical notation:

$$A = \bigcup_m S(m) \text{ where } m \in N \mid 8 \leq m \leq 80$$

and $$S(m) = \{R_{n,n+m-1} \mid n \in \{1, 2, 3, \ldots, L-m+1\}\}$$

where the mathematical operator | indicates "such that", where the mathematical operator $\in$ indicates "a member of a set" (e.g. y$\in$Z indicates that element y is a member of set Z), where x is a variable, where N indicates all natural numbers, defined as positive integers, and where the mathematical operator $\cup$ indicates "the union of sets".

For example, the set of regions for m equal to 8, 9 and 80 can be constructed in the following manner. The set of regions, each 8 nucleobases in length, S(m=8), in a target nucleobase sequence 100 nucleobases in length (L=100), beginning at position 1 (n=1) of the target nucleobase sequence, can be created using the following expression:

$$S(8)=\{R_{1,8}|n\epsilon\{1,2,3,\ldots,93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20)=\{R_{1,20}|n\epsilon\{1,2,3,\ldots,81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80)=\{R_{1,80}|n\epsilon\{1,2,3,\ldots,21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8, 2-9, 3-10 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression:

$$A = \bigcup_m S(m)$$

where ∪ represents the union of the sets obtained by combining all members of all sets.

The mathematical expressions described herein define all possible target regions in a target nucleobase sequence of any length L, where the region is of length m, and where m is greater than or equal to 8 and less than or equal to 80 nucleobases and, and where m is less than L, and where n is less than L−m+1.

In one embodiment, the oligonucleotide compounds of this invention are 100% complementary to these sequences or to small sequences found within each of the above listed sequences. In another embodiment the oligonucleotide compounds have from at least 3 or 5 mismatches per 20 consecutive nucleobases in individual nucleobase positions to these target regions. Still other compounds of the invention are targeted to overlapping regions of the above-identified portions of the C-reactive protein sequence.

D. Screening and Target Validation

In a further embodiment, the "preferred target segments" identified herein may be employed in a screen for additional compounds that modulate the expression of C-reactive protein. "Modulators" are those compounds that decrease or increase the expression of a nucleic acid molecule encoding C-reactive protein and which comprise at least an 8-nucleobase portion that is complementary to a preferred target segment. The screening method comprises the steps of contacting a preferred target segment of a nucleic acid molecule encoding C-reactive protein with one or more candidate modulators, and selecting for one or more candidate modulators which decrease or increase the expression of a nucleic acid molecule encoding C-reactive protein. Once it is shown that the candidate modulator or modulators are capable of modulating (e.g. either decreasing or increasing) the expression of a nucleic acid molecule encoding C-reactive protein, the modulator may then be employed in further investigative studies of the function of C-reactive protein, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science*, 2002, 295, 694-697).

The compounds of the present invention can also be applied in the areas of drug discovery and target validation. The present invention comprehends the use of the compounds and preferred target segments identified herein in drug discovery efforts to elucidate relationships that exist between C-reactive protein and a disease state, phenotype, or condition. These methods include detecting or modulating C-reactive protein comprising contacting a sample, tissue, cell, or organism with the compounds of the present invention, measuring the nucleic acid or protein level of C-reactive protein and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention are utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, are used as tools in differential and/or combinatorial analyses to elucidate expression patterns of a portion or the entire complement of genes expressed within cells and tissues.

As used herein the term "biological system" or "system" is defined as any organism, cell, cell culture or tissue that expresses, or is made competent to express products of the gene encoding C-reactive protein. These include, but are not limited to, humans, transgenic animals, cells, cell cultures, tissues, xenografts, transplants and combinations thereof.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

The compounds of the invention are useful for research and diagnostics, because these compounds hybridize to nucleic acids encoding C-reactive protein. Primers and probes are useful in methods requiring the specific detection of nucleic acid molecules encoding C-reactive protein and in the amplification of said nucleic acid molecules for detection or for use in further studies of C-reactive protein. Hybridization of the primers and probes disclosed herein with a nucleic acid encoding C-reactive protein can be detected by means known in the art. Such means may include conjugation of an enzyme to the primers and probes, radiolabelling of the primers and probes or any other suitable detection means. Kits using such detection means for detecting the level of C-reactive protein in a sample may also be prepared.

The invention further provides for the use of a compound or composition of the invention in the manufacture of a medicament for the treatment of any and all conditions disclosed herein.

Antisense compounds of the invention are provided for the treatment of, or use in the manufacture of a medicament for the treatment of, neurological conditions including obstructive sleep apnea, Alzheimer's disease, ALS, Parkinson's disease, various ataxias, and macular degeneration.

Antisense compounds of the invention are provided for the treatment of, or use in the manufacture of a medicament for the treatment of, metabolic conditions including obesity, metabolic syndrome, and diabetes.

Antisense compounds of the invention are provided for the treatment of, or use in the manufacture of a medicament for the treatment of, cardiovascular conditions including sudden cardiac death, coronary artery disease (CAD), unstable angina, stroke, elective stent placement, angioplasty, atherosclerosis, post percutaneous transluminal angioplasty (PTCA), post peripheral vascular disease, post myocardial infarction (MI), cardiac transplantation, hypertension, mitral valve commissurotomy, thrombosis, deep vein thrombus, end-stage renal disease (ESRD), renal dialysis, complement activation, congestive heart failure, systemic vasculitis, and cardiopulmonary bypass Antisense compounds of the invention are provided for the treatment of, or use in the manufacture of a medicament for the treatment of, women's health conditions including premenstrual syndrome (PMS) and dysmenorhhoea.

Antisense compounds of the invention are provided for the treatment of, or use in the manufacture of a medicament for the treatment of, inflammatory diseases including gingivitis, inflammatory bowel disease, ulcerative colitis, rheumatoid arthritis, osteoarthritis, and axial spondyloarthritis.

Antisense compounds of the invention are provided for the treatment of, or use in the manufacture of a medicament for the treatment of, infectious diseases including HIV-associated rheumatic disorders and bacterial infection.

Antisense compounds of the invention are provided for the treatment of, or use in the manufacture of a medicament for the treatment of, pulmonary conditions including asthma and chronic obstructive pulmonary disease.

Antisense compounds of the invention are provided for the treatment of, or use in the manufacture of a medicament for the treatment of, musculoskeletal conditions including lower back pain, intense physical exercise, endurance training, and age-related disorders.

Antisense compounds of the invention are provided for the treatment of, or use in the manufacture of a medicament for the treatment of, cancers including pulmonary cancer and colon cancer.

Among diagnostic uses is the measurement of C-reactive protein levels in patients to identify those who may benefit from a treatment strategy aimed at attenuation of inflammation. Such patients suitable for diagnosis include patients with coronary artery stenting, e.g., to diagnose tendencies for myocardial infarction or patients with ESRD or other symptoms related to renal disorders, e.g., hypertension, duresis, renal failure.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder that can be treated by modulating the expression of C-reactive protein is treated by administering antisense compounds in accordance with this invention. For example, in one non-limiting embodiment, the methods comprise the step of administering to the animal in need of treatment, a therapeutically effective amount of a C-reactive protein inhibitor. The C-reactive protein inhibitors of the present invention effectively inhibit the activity of the C-reactive protein or inhibit the expression of the C-reactive protein. For example, such a compound or composition that reduces levels of C-reactive protein is useful to prevent morbidity and mortality for subjects with acute coronary syndrome. Such a composition is useful for reducing inflammation mediated by C-reactive protein in a subject, e.g., to treat or prevent or reduce the progression of, atherosclerosis; to treat or prevent or reduce the progression of, acute vascular damage at atherosclerotic plaque sites or in coronary arteries; or to treat or prevent or reduce the progression of, damage caused by inflammation associated with myocardial infarctions or renal inflammation. Still other therapeutic or prophylactic methods using the C-reactive protein inhibitory compounds of this invention include to treat patients with coronary artery stenting; or to treat patients with ESRD or other renal diseases or related inflammatory disorders.

In one embodiment, the activity or expression of C-reactive protein in an animal is inhibited by about 10%. Preferably, the activity or expression of C-reactive protein in an animal is inhibited by about 30%. More preferably, the activity or expression of C-reactive protein in an animal is inhibited by 50% or more. Thus, the oligomeric compounds modulate expression of C-reactive protein mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of C-reactive protein may be measured in serum, adipose tissue, liver or any other body fluid, tissue or organ of the animal. Preferably, the cells contained within said fluids, tissues or organs being analyzed contain a nucleic acid molecule encoding C-reactive protein and/or C-reactive protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue that may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497-1500.

Further embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602, 240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-O-methoxyethyl (2'-O—$CH_2CH_2OCH_3$, also known as 2'-O-(2-methoxyethyl) or 2'-methoxyethoxy or 2'-MOE) (Martin et al., *Helv. Chim. Acta,* 1995, 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in International Patent Publication Nos. WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1, 4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999), which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example International Patent Publication No. WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds that are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Preferred chimeric oligonucleotides are those disclosed in the Examples herein. Particularly preferred chimeric oligonucleotides are those referred to as ISIS 133726, ISIS 133719, ISIS 140177, ISIS 104183, ISIS 140180, ISIS 133731, ISIS 140187, ISIS 133712, ISIS 140194, ISIS 133730, and ISIS 133729.

Chimeric antisense compounds of the invention may be formed as composite structures of two or more oligonucleotides, modified oligonucleotides, oligonucleosides and/or oligonucleotide mimetics as described above. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers". Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3').

In a hemimer, an "open end" chimeric antisense compound, 20 nucleotides in length, a gap segment, located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. For example, a 20-nucleotide hemimer can have a gap segment of 10 nucleotides at the 5' end and a second segment of 10 nucleotides at the 3' end. Alternatively, a 20-nucleotide hemimer can have a gap segment of 10 nucleotides at the 3' end and a second segment of 10 nucleotides at the 5' end.

Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes, which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. Patent Publication No. 2003/0040497 (Feb. 27, 2003) and its parent applications; U.S. Patent Publication No. 2003/0027780 (Feb. 6, 2003) and its parent applications; and U.S. patent application Ser. No. 10/071,822, filed Feb. 8, 2002, each of which is incorporated herein by reference in their entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Oligonucleotides may be formulated for delivery in vivo in an acceptable dosage form, e.g. as parenteral or non-parenteral formulations. Parenteral formulations include intravenous (IV), subcutaneous (SC), intraperitoneal (IP), intravitreal and intramuscular (IM) formulations, as well as formulations for delivery via pulmonary inhalation, intranasal administration, topical administration, etc. Non-parenteral formulations include formulations for delivery via the alimentary canal, e.g. oral administration, rectal administration, intrajejunal instillation, etc. Rectal administration includes administration as an enema or a suppository. Oral administration includes administration as a capsule, a gel capsule, a pill, an elixir, etc.

In some embodiments, an oligonucleotide may be administered to a subject via an oral route of administration. The subject may be an animal or a human (man). An animal subject may be a mammal, such as a mouse, a rat, a dog, a guinea pig, a monkey, a non-human primate, a cat or a pig. Non-human primates include monkeys and chimpanzees. A suitable animal subject may be an experimental animal, such as a mouse, rat, mouse, a rat, a dog, a monkey, a non-human primate, a cat or a pig.

In some embodiments, the subject may be a human. In certain embodiments, the subject may be a human patient in need of therapeutic treatment as discussed in more detail herein. In certain embodiments, the subject may be in need of modulation of expression of one or more genes as discussed in more detail herein. In some particular embodiments, the subject may be in need of inhibition of expression of one or more genes as discussed in more detail herein. In particular embodiments, the subject may be in need of modulation, i.e. inhibition or enhancement, of C-reactive protein in order to obtain therapeutic indications discussed in more detail herein.

In some embodiments, non-parenteral (e.g. oral) oligonucleotide formulations according to the present invention result in enhanced bioavailability of the oligonucleotide. In this context, the term "bioavailability" refers to a measurement of that portion of an administered drug, which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound's blood plasma concentration curve ($AUC_0$) after non-parenteral (e.g. oral, rectal, intrajejunal) administration may be divided by the area under the drug's plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition's bioavailability is said to be enhanced in comparison to another composition's bioavailability when the first composition's relative bioavailability ($RB_1$) is greater than the second composition's relative bioavailability ($RB_2$).

In general, bioavailability correlates with therapeutic efficacy when a compound's therapeutic efficacy is related to the blood concentration achieved, even if the drug's ultimate site of action is intracellular (van Berge-Henegouwen et al., *Gastroenterol.*, 1977, 73, 300). Bioavailability studies have been used to determine the degree of intestinal absorption of a drug by measuring the change in peripheral blood levels of the drug after an oral dose (DiSanto, Chapter 76 *In: Remington's Pharmaceutical Sciences*, 18th Ed., Gennaro, ed., Mack Publishing Co., Easton, Pa., 1990, pages 1451-1458).

In general, an oral composition's bioavailability is said to be "enhanced" when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of an oligonucleotide, without interfering with the activity of the oligonucleotide, and in a such a manner the oligonucleotide can be introduced into the body of an animal without unacceptable side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, *Crit. Rev. Ther. Drug Carrier Systems,* 1990, 7, 1 and Lee et al., *Crit. Rev. Ther. Drug Carrier Systems,* 1991, 8, 91. It has been found that the uptake and delivery of oligonucleotides, relatively complex molecules which are known to be difficult to administer to animals and man, can be greatly improved even when administered by non-parenteral means through the use of a number of different classes of penetration enhancers.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal or human subject, will comprise modified oligonucleotides having one or more modifications for enhancing affinity, stability, tissue distribution, or other biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments according to the present invention, the oligonucleotide has at least two phosphorothioate linkers. In some embodiments, wherein the oligonucleotide has exactly n nucleosides, the oligonucleotide has from one to n−1 phosphorothioate linkages. In some embodiments, wherein the oligonucleotide has exactly n nucleosides, the oligonucleotide has n−1 phosphorothioate linkages. In other embodiments wherein the oligonucleotide has exactly n nucleoside, and n is even, the oligonucleotide has from 1 to n/2 phosphorothioate linkages, or, when n is odd, from 1 to (n−1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least on PS linkage.

In some embodiments, at least one of the nucleosides is modified on the ribosyl sugar unit by a modification that imparts nuclease stability, binding affinity or some other beneficial biological property to the sugar. In some cases, the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2-O-methyl, and 2'-O-substituted alkyl, e.g. 2'-O-methoxyethyl, 2'-O-aminopropyl, etc. In some embodiments, the oligonucleotide contains at least one 2'-modification. In some embodiments, the oligonucleotide contains at least 2 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides. In further embodiments, oligonucleotides are capable of eliciting cleavage by dsRNAse enzymes.

Oral compositions for administration of non-parenteral oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered.

Delivery of a drug via the oral mucosa, as in the case of buccal and sublingual administration, has several desirable features, including, in many instances, a more rapid rise in plasma concentration of the drug than via oral delivery (Harvey, Chapter 35 In: *Remington's Pharmaceutical Sciences,* 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho,* 1992, 19(10 Suppl.), 1591). Pharmaceutical compositions, including liposomal formulations, can be delivered directly into portions of the alimentary canal, such as, e.g., the duodenum (Somogyi et al., *Pharm. Res.,* 1995, 12, 149) or the gastric submucosa (Akamo et al., *Japanese J. Cancer Res.,* 1994, 85, 652) via endoscopic means. Gastric lavage devices (Inoue et al., *Artif. Organs,* 1997, 21, 28) and percutaneous endoscopic feeding devices (Pennington et al., *Ailment Pharmacol. Ther.,* 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 In: *Remington's Pharmaceutical Sciences,* 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 *In: Goodman & Gilman's The Pharmacological Basis of Therapeutics*, 9th Ed., Hardman et al., eds., McGraw-Hill, New York, N.Y., 1996).

One advantageous method of non-parenteral administration oligonucleotide compositions is oral delivery. Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"), which are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, page 92); and perfluorohemical emulsions, such as FC-43 (Takahashi et al., *J. Pharm. Phamacol.*, 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, page 92; Muranishi, Critical Reviews in Therapeutic Drug Carrier Systems, 1990, 7, 1; El-Hariri et al., *J. Pharm. Pharmacol.*, 1992, 44, 651).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at lease one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, a first phase comprises at least one oligonucleotide, at least one penetration enhancer, while a second phase comprises at least one penetration enhancer and a release-retardant. In particular embodiments, an oral oligonucleotide comprises a first phase comprising particles containing an oligonucleotide and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 *In: Goodman & Gilman's The Pharmacological Basis of Therapeutics*, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 *In: Remington's Pharmaceutical Sciences*, 18th Ed., Gennaro, ed., Mack Publishing Co., Easton, Pa., 1990, pages 782-783; Muranishi, *Critical Reviews in Therapeutic Drug Carrier Systems*, 1990, 7, 1; Yamamoto et al., *J. Pharm. Exp. Ther.*, 1992, 263, 25; Yamashita et al., *J. Pharm. Sci.*, 1990, 79, 579).

In some embodiments, penetration enhancers useful in some embodiments of present invention are mixtures of penetration enhancing compounds. One such penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Anther such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1; Buur et al., *J. Control Rel.*, 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, *Critical Reviews in Therapeutic Drug Carrier Systems*, 1990, 7, 1). This class of penetration enhancers includes, but is not limited to, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), can be used.

Some oral oligonucleotide compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115; Takakura et al., *Antisense & Nucl. Acid Drug Dev.*, 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB™ disintegrating agent); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipuritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, from 0.1 µg to 10 g per kg of body weight, from 1.0 µg to 1 g per kg of body weight, from 10.0 µg to 100 mg per kg of body weight, from 100 µg to 10 mg per kg of body weight, or from 1 mg to 5 mg per kg of body weight and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The effects of treatments with therapeutic compositions can be assessed following collection of tissues or fluids from a patient or subject receiving said treatments. It is known in the art that a biopsy sample can be procured from certain tissues without resulting in detrimental effects to a patient or subject. In certain embodiments, a tissue and its constituent cells comprise, but are not limited to, blood (e.g., hematopoietic cells, such as human hematopoietic progenitor cells, human hematopoietic stem cells, $CD34^+$ cells $CD4^+$ cells), lymphocytes and other blood lineage cells, bone marrow, breast, cervix, colon, esophagus, lymph node, muscle, peripheral blood, oral mucosa and skin. In other embodiments, a fluid and its constituent cells comprise, but are not limited to, blood, urine, semen, synovial fluid, lymphatic fluid and cerebro-spinal fluid. Tissues or fluids procured from patients can be evaluated for expression levels of the target mRNA or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry.

Furthermore, the effects of treatment can be assessed by measuring biomarkers associated with the disease or condition in the aforementioned tissues and fluids, collected from a patient or subject receiving treatment, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

While the present invention has been described with specificity in accordance with certain of its preferred embodiments, the following examples serve only to illustrate the invention and are not intended to limit the same. Each of the references, GENBANK® accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and International Patent Publication No. WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4, 4'-Dimethoxytriphenylmethyl)-2'-deoxy-N4-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-N-benzoyl-5-methylcytidin-3'-O-yl]-2-cyanoethyl-N, N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4, 4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N- diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides, such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 seconds and preceded by the normal capping step. After cleavage from the CPG column and deblocking in concentrated ammonium hydroxide at 55° C. (12-16 hours), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in International Patent Application Nos. PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group, which has the following important properties. It is stable to the conditions of nucleoside phosphoramidite synthesis and oligonucleotide synthesis. However, after oligonucleotide synthesis the oligonucleotide is treated with methylamine, which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis. Yet, when subsequently modified, this orthoester permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand*, 1990, 44, 639-641; Reddy, M. P., et al., *Tetrahedrom Lett.*, 1994, 25, 4311-4314; Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2%'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hours at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting C-Reactive Protein In accordance with the present invention, a series of nucleic acid duplexes comprising the antisense compounds of the present invention and their complements can be designed to target C-reactive protein. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex are complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising an antisense strand having the sequence CGAGAGGCGGACGGGACCG (SEQ ID NO:624) and having a two-nucleobase overhang of deoxythymidine(dT) has the following structure (Antisense SEQ ID NO:625, Complement SEQ ID NO:626):

Overhangs can range from 2 to 6 nucleobases and these nucleobases may or may not be complementary to the target nucleic acid. In another embodiment, the duplexes may have an overhang on only one terminus.

In another embodiment, a duplex comprising an antisense strand having the same sequence CGAGAGGCGGACGG-GACCG (SEQ ID NO:624) is prepared with blunt ends (no single stranded overhang) as shown (Antisense SEQ ID NO:624, Complement SEQ ID NO:627):

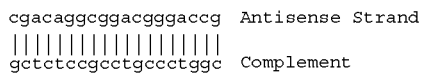

The RNA duplex can be unimolecular or bimolecular; i.e., the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM. This solution can be stored frozen (−20° C.) and freeze-thawed up to 5 times.

Once prepared, the duplexed antisense compounds are evaluated for their ability to modulate C-reactive protein expression.

When cells reached 80% confluency, they are treated with duplexed antisense compounds of the invention. For cells grown in 96-well plates, wells are washed once with 200 µL OPTI-MEM™-1 reduced-serum medium (Gibco BRL) and then treated with 130 µL of OPTI-MEM™-1 medium containing 12 µg/mL LIPOFECTIN™ reagent (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full-length material. The relative amounts of phosphorothioate and phosphodiester linkages obtained in the synthesis were determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 7

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ apparatus) or, for individually prepared samples, on a commercial CE apparatus (e.g., Beckman P/ACE™ 5000, ABI 270 apparatus). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Hep3B Cells:

The human hepatoma cell line Hep3B (Hep3B2.1-7) was obtained from the American Type Culture Collection (ATCC Catalog #HB-8064; Manassas, Va.). This cell line was initially derived from a hepatocellular carcinoma of an 8-yr-old black male. The cells are epithelial in morphology and are tumorigenic in nude mice. These cells can be induced to produce C-reactive protein by addition of media containing 1 µM dexamethasone (Sigma-Catalog #D2915 St. Louis, Mo.), 400 U/ml IL1B (Sigma-Catalog #19401) and 200 U/ml IL6 (Sigma-Catalog#I139), according to the protocol described by Lozanski, et al., (Cytokine, vol. 8, 1996 pp. 534-540). Hep3B cells were routinely cultured in Minimum Essential Medium (MEM) with Earle's Balanced Salt Solution, 2 mM L-glutamine, 1.5 g/L sodium bicarbonate, 0.1 mM nonessential amino acids, 1.0 mM sodium pyruvate (ATCC #20-2003, Manassas, Va.) and with 10% heat-inactivated fetal bovine serum (Invitrogen Corporation, Carlsbad, Calif.). Cells were routinely passaged by trypsinization and dilution when they reached 90% confluence.

In order to determine antisense oligonucleotide inhibition of induced C-reactive protein, Hep3B cells were plated at a density of 100,000 cells into each well of a 6 well plate (Primaria, Franklin N.J., Catalog# 3846) in MEM supplemented with 10% fetal bovine serum and allowed to attach overnight. The next day, cells were induced to produce C-reactive protein for 24 hours in regular media supplemented with a final concentration of 1 µM dexamethasone, 400 U/ml IL1B and 200 U/ml IL6 as described above. At the end of this induction period, the media was removed and cells treated for 4 hrs with 50-150 nM of antisense oligonucleotide and 3.0-4.5 µg LIPOFECTIN™ reagent in MEM alone (minus) serum supplemented with the three cytokines. At the end of the 4-hour drug treatment, the media was removed and fresh MEM containing FCS and cytokines was added to each well and allowed to sit for an additional 20 hrs. RNA was harvested 24 hrs after treatment with oligonucleotide using the QIAGEN® RNeasy (Qiagen Ltd, Valencia, Calif.) procedure and C-reactive protein RNA detected using RT-PCR analysis.

Primary Rat Hepatocytes:

Primary rat hepatocytes were prepared from Sprague-Dawley rats purchased from Charles River Labs (Wilmington, Mass.) and were routinely cultured in DMEM, high glucose (Invitrogen Corporation, Carlsbad, Calif.) supplemented with 10% fetal bovine serum (Invitrogen Corporation, Carlsbad, Calif.), 100 units per ml penicillin, and 100 micrograms per ml streptomycin (Invitrogen Corporation, Carlsbad, Calif.). Cells were cultured to 80% confluence for use in antisense oligonucleotide transfection experiments.

Primary Rabbit Hepatocytes:

Primary rabbit hepatocytes from New Zealand White rabbits were purchased from InVitro Technologies (Baltimore, Md.) and were routinely cultured in DMEM, high glucose (Invitrogen Corporation, Carlsbad, Calif.) supplemented with 10% fetal bovine serum (Invitrogen Corporation, Carlsbad, Calif.), 100 units per ml penicillin, and 100 micrograms per ml streptomycin (Invitrogen Corporation, Carlsbad, Calif.). Primary rabbit hepatocytes are purchased and transfected at 100% confluency.

Primary Mouse Hepatocytes:

Primary mouse hepatocytes were prepared from Balb/c mice purchased from Charles River Labs (Wilmington, Mass.) and were routinely cultured in DMEM, high glucose (Invitrogen Corporation, Carlsbad, Calif.) supplemented with 10% fetal bovine serum (Invitrogen Corporation, Carlsbad, Calif.), 100 units per ml penicillin, and 100 micrograms per ml streptomycin (Invitrogen Corporation, Carlsbad, Calif.). Cells were cultured to 80% confluence for use in antisense oligonucleotide transfection experiments.

Primary Human Hepatocytes:

Pre-plated primary human hepatocytes were purchased from InVitro Technologies (Baltimore, Md.). Cells were cultured in high-glucose DMEM (Invitrogen Corporation, Carlsbad, Calif.) supplemented with 10% fetal bovine serum (Invitrogen Corporation, Carlsbad, Calif.), 100 units/mL penicillin and 100 µg/mL streptomycin (Invitrogen Corporation, Carlsbad, Calif.). Cells were transfected with oligonucleotide upon receipt from the vendor.

Primary Cynomolgus Monkey Hepatocytes:

Pre-plated primary Cynomolgus monkey hepatocytes were purchased from InVitro Technologies (Baltimore, Md.). Cells were cultured in high-glucose DMEM (Invitrogen Corporation, Carlsbad, Calif.) supplemented with 10% fetal bovine serum (Invitrogen Corporation, Carlsbad, Calif.), 100 units/mL penicillin and 100 μg/mL streptomycin (Invitrogen Corporation, Carlsbad, Calif.). Cells were treated with oligonucleotide upon receipt from the vendor.

Treatment with Antisense Compounds:

When cells reached 65-75% confluency, they were treated with oligonucleotide. For cells grown in 96-well plates, wells were washed once with 100 μL OPTI-MEM™-1 reduced-serum medium or with serum-free DMEM, high glucose (Invitrogen Corporation, Carlsbad, Calif.) and then treated with 130 μL of OPTI-MEM™-1 medium containing 3.75 μg/mL LIPOFECTIN™ reagent (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO:1), which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO:3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of C-Reactive Protein Expression

Antisense modulation of C-reactive protein expression can be assayed in a variety of ways known in the art. For example, C-reactive protein mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of C-reactive protein can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to C-reactive protein can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of C-Reactive Protein Inhibitors

Once C-reactive protein inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of C-reactive protein in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.)

In one non-limiting example, cells determined to be appropriate for a particular phenotypic assay (i.e., MCF-7 cells selected for breast cancer studies; adipocytes for obesity studies) are treated with C-reactive protein inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status, which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the C-reactive protein inhibitors. Hallmark genes, or those genes suspected to be associated with a specific disease state, condition, or phenotype, are measured in both treated and untreated cells.

The cells subjected to the phenotypic assays described herein derive from in vitro cultures or from tissues or fluids isolated from living organisms, both human and non-human. In certain embodiments, a tissue and its constituent cells comprise, but are not limited to, blood (e.g., hematopoietic cells, such as human hematopoietic progenitor cells, human hematopoietic stem cells, $CD34^+$ cells $CD4^+$ cells), lymphocytes and other blood lineage cells, bone marrow, brain, stem cells, blood vessel, liver, lung, bone, breast, cartilage, cervix, colon, cornea, embryonic, endometrium, endothelial, epithelial, esophagus, facia, fibroblast, follicular, ganglion cells, glial cells, goblet cells, kidney, lymph node, muscle, neuron, ovaries, pancreas, peripheral blood, prostate, skin, skin, small intestine, spleen, stomach, testes and fetal tissue. In other embodiments, a fluid and its constituent cells comprise, but are not limited to, blood, urine, synovial fluid, lymphatic fluid and cerebro-spinal fluid. The phenotypic assays may also be performed on tissues treated with C-reactive protein inhibitors ex vivo.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN® BIO-ROBOT™ 9604-(Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of C-Reactive Protein mRNA Levels

Quantitation of C-reactive protein mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Gene target quantities are obtained by reverse-transcriptase, real-time PCR. Prior to the real-time PCR, isolated RNA is subjected to a reverse transcriptase (RT) reaction, for the purpose of generating complementary DNA (cDNA). Reverse transcriptase and real-time PCR reagents were obtained from Invitrogen Corporation, (Carlsbad, Calif.). RT, real-time PCR reactions were carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension). This method of obtaining gene target quantities is herein referred to as real-time PCR.

Gene target quantities obtained by real-time PCR are normalized using either the expression level of GAPDH, a gene whose expression is constant, or by quantifying total RNA using RiboGreen™ reagent (Molecular Probes, Inc. Eugene, Oreg.). GAPDH expression is quantified by real-time PCR by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ reagent are taught in Jones, L. J., et al, (*Analytical Biochemistry*, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 reader (PE Applied Biosystems) with excitation at 485 nm and emission at 530 nm.

Probes and primers to human C-reactive protein were designed to hybridize to a human C-reactive protein sequence, using published sequence information (GENBANK® accession number M11725.1, incorporated herein as SEQ ID NO:4). For human C-reactive protein the PCR primers were:

forward primer: TGACCAGCCTCTCTCATGCTT (SEQ ID NO:5)

reverse primer: TCCGACTCTTTGGGAAACACA (SEQ ID NO:6) and the PCR probe was: FAM-TGTCGAGGAAG-GCTT-TAMRA (SEQ ID NO:7) where FAM is the fluorescent dye and TAMRA is the quencher dye. For human GAPDH the PCR primers were:

forward primer: GAAGGTGAAGGTCGGAGTC (SEQ ID NO:8)

reverse primer: GAAGATGGTGATGGGATTTC (SEQ ID NO:9) and the PCR probe was: 5' JOE-CAAGCTTCCCGT-TCTCAGCC-TAMRA 3' (SEQ ID NO:10) where JOE is the fluorescent reporter dye and TAMRA is the quencher dye.

Probes and primers to rat C-reactive protein were designed to hybridize to a rat C-reactive protein sequence, using published sequence information (GENBANK® accession number M83176.1, incorporated herein as SEQ ID NO:11). For rat C-reactive protein the PCR primers were:

forward primer: AAGCACCCCCAATGTCACC (SEQ ID NO:12)

reverse primer: GGGATGGCAGAGCCAATGTA (SEQ ID NO:13) and the PCR probe was: FAM-TCCTGGAT-TCAAGCTTCTATGTGCCTTCA-TAMRA (SEQ ID NO:14) where FAM is the fluorescent reporter dye and TAMRA is the quencher dye. For rat GAPDH the PCR primers were:

forward primer: TGTTCTAGAGACAGCCGCATCTT (SEQ ID NO:15)

reverse primer: CACCGACCTTCACCATCTTGT (SEQ ID NO:16) and the PCR probe was: 5' JOE-TTGTGCAGTGC-CAGCCTCGTCTCA-TAMRA 3' (SEQ ID NO:17) where JOE is the fluorescent reporter dye and TAMRA is the quencher dye.

Example 14

Northern Blot Analysis of C-Reactive Protein mRNA Levels

Eighteen hours after antisense treatment, cell monolayers were washed twice with cold PBS and lysed in 1 mL RNA-ZOL™ reagent (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKE™ UV Crosslinker 2400 instrument (Stratagene, Inc, La Jolla, Calif.) and then probed using QUICKHYB™ hybridization solution (Stratagene, La Jolla, Calif.) using manufacturer's recommendations for stringent conditions.

To detect human C-reactive protein, a human C-reactive protein specific probe was prepared by PCR using the forward primer TGACCAGCCTCTCTCATGCTT (SEQ ID NO:5) and the reverse primer TCCGACTCTTTGGGAAACACA (SEQ ID NO:6). To normalize for variations in loading and transfer efficiency membranes were stripped and probed for human glyceraldehyde-3-phosphate dehydrogenase (GAPDH) RNA (Clontech, Palo Alto, Calif.).

To detect rat C-reactive protein, a rat C-reactive protein specific probe was prepared by PCR using the forward primer TGACCAGCCTCTCTCATGCTT (SEQ ID NO:12) and the reverse primer TCCGACTCTTTGGGAAACACA (SEQ ID NO:13). To normalize for variations in loading and transfer efficiency membranes were stripped and probed for rat glyceraldehyde-3-phosphate dehydrogenase (GAPDH) RNA (Clontech, Palo Alto, Calif.).

Example 15

Antisense Inhibition of Human C-Reactive Protein Expression by Chimeric Phosphorothioate Oligonucleotides Having 2'-MOE Wings and a Deoxy Gap In accordance with the present invention, a series of antisense compounds was designed to target different regions of the human C-reactive protein RNA, using published sequences (GENBANK® accession number M11725.1, incorporated herein as SEQ ID NO:4). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human C-reactive protein mRNA levels by quantitative real-time PCR as described in other examples herein. Data, shown in Table 1, are averages from three experiments in which cytokine-induced Hep3B cells were treated with 150 nM of the antisense oligonucleotides of the present invention. The positive control for each data point is identified in the table by sequence ID number. If present, "N.D." indicates "no data".

TABLE 1

Inhibition of human C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 133709 | 5'UTR | 4 | 16 | gcaggtgtcagagcttcggg | 77 | 19 |
| 133710 | 5'UTR | 4 | 71 | gcagtaagggagtttgcgcc | 71 | 20 |
| 133711 | 5'UTR | 4 | 181 | gcctgaattcactcctttgg | 87 | 21 |
| 133712 | Start Codon | 4 | 221 | agcttctccatggtcacgtc | 92 | 22 |
| 133713 | Coding | 4 | 281 | tggcccttacctgtctggcc | 88 | 23 |
| 133714 | Intron | 4 | 311 | ctcagatcaaaactctccca | 30 | 24 |
| 133715 | Intron | 4 | 341 | ttcatgcagtcttagacccc | N.D. | 25 |
| 133716 | Coding | 4 | 551 | gtctgtgagccagaaaaaca | 77 | 26 |
| 133717 | Coding | 4 | 701 | cgagaaaatactgtacccac | 82 | 27 |
| 133718 | Coding | 4 | 781 | gacccacccactgtaaaact | 82 | 28 |
| 133719 | Coding | 4 | 871 | cagaactccacgatccctga | 96 | 29 |
| 133720 | Coding | 4 | 1091 | attaggactgaagggcccgc | 86 | 30 |
| 133721 | Stop Codon | 4 | 1171 | agctggcctcagggccacag | 80 | 31 |
| 133722 | 3'UTR | 4 | 1191 | gaggtaccttcaggacccac | 89 | 32 |
| 133723 | 3'UTR | 4 | 1361 | cccagaccagacactttacc | 88 | 33 |
| 133724 | 3'UTR | 4 | 1391 | tggaccatttcccagcatag | 67 | 34 |
| 133725 | 3'UTR | 4 | 1631 | ttctgagactgaagagccct | 27 | 35 |
| 133726 | 3'UTR | 4 | 1671 | gcactctggacccaaaccag | 96 | 36 |
| 133727 | 3'UTR | 4 | 1711 | caggagacctgggcccagca | 85 | 37 |
| 133728 | 3'UTR | 4 | 1918 | cccagaagagccataaaatt | 27 | 38 |
| 133729 | 3'UTR | 4 | 1961 | attcacagcccacaaggtt | 90 | 39 |
| 133730 | 3'UTR | 4 | 2161 | agaagatgtctcactcccaa | 91 | 40 |
| 133731 | 3'UTR | 4 | 2291 | tgtttgtcaatcccttggct | 93 | 41 |

TABLE 1-continued

Inhibition of human C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 133732 | 3'UTR | 4 | 2431 | ttctaaagcaactatcagaa | 64 | 42 |
| 140167 | 5'UTR | 4 | 111 | gccttagagctacctcctcc | 70 | 43 |
| 140168 | 5'UTR | 4 | 201 | ctgctgccagtgatacaagg | 69 | 44 |
| 140169 | Intron | 4 | 317 | ccatacctcagatcaaaact | 48 | 45 |
| 140170 | Intron | 4 | 451 | accccttctccagttacaca | 69 | 46 |
| 140171 | Coding | 4 | 671 | cagttccgtgtagaagtgga | 43 | 47 |
| 140172 | Coding | 4 | 761 | gtatcctatatccttagacc | N.D. | 48 |
| 140173 | Coding | 4 | 821 | tggagctactgtgacttcag | 82 | 49 |
| 140174 | Coding | 4 | 861 | cgatccctgaggcggactcc | N.D. | 50 |
| 140175 | Coding | 4 | 901 | ctcttcctcaccctgggctt | 84 | 51 |
| 140176 | Coding | 4 | 921 | cagtgtatccttcttcaga | 68 | 52 |
| 140177 | Coding | 4 | 951 | gccccaagatgatgcttgct | 95 | 53 |
| 140178 | Coding | 4 | 1031 | gtcccacatgttcacatttc | 61 | 54 |
| 140179 | Coding | 4 | 1111 | agtgcccgccagttcaggac | 86 | 55 |
| 140180 | Coding | 4 | 1141 | gtgaacacttcgccttgcac | 94 | 56 |
| 140181 | 3'UTR | 4 | 1341 | tccattctcaggcgctgagg | 85 | 57 |
| 140182 | 3'UTR | 4 | 1461 | gaaattatctccaagatctg | 33 | 58 |
| 140183 | 3'UTR | 4 | 1551 | cagcgcttccttctcagctc | 94 | 59 |
| 140184 | 3'UTR | 4 | 1611 | gtgaatgtgggcaatgctcc | 58 | 60 |
| 140185 | 3'UTR | 4 | 1651 | acacctggccagtgtcctga | N.D. | 61 |
| 140186 | 3'UTR | 4 | 1771 | cctttccagtgtgctttgag | N.D. | 62 |
| 140187 | 3'UTR | 4 | 1831 | tagtgcttcattttgctctg | 93 | 63 |
| 140188 | 3'UTR | 4 | 1971 | tgaagaaagaattcacagcc | 58 | 64 |
| 140189 | 3'UTR | 4 | 2041 | ggctcctctgacaggacacc | 86 | 65 |
| 140190 | 3'UTR | 4 | 2101 | gctaggaacacgtaactatc | 71 | 66 |
| 140191 | 3'UTR | 4 | 2121 | ggaagactgtagttggtcct | 35 | 67 |
| 140192 | 3'UTR | 4 | 2211 | ctactggtggtcccaggttc | 77 | 68 |
| 140193 | 3'UTR | 4 | 2271 | cctccacttccagtttggct | 77 | 69 |
| 140194 | 3'UTR | 4 | 2341 | ctggttccagacaaggctga | 92 | 70 |
| 140195 | 3'UTR | 4 | 2402 | gactcactcaagtaaacagg | 71 | 71 |
| 140196 | 3'UTR | 4 | 2461 | ttcaaaggtcatagagaagt | 28 | 72 |

As shown in Table 1, SEQ ID NOs 19, 20, 21, 22, 23, 25, 26, 27, 28, 29, 30, 31, 32, 33, 34, 36, 37, 39, 40, 41, 42, 43, 44, 46, 48, 49, 50, 51, 52, 53, 54, 55, 56, 57, 59, 60, 61, 62, 63, 64, 65, 66, 68, 69, 70 and 71 demonstrated at least 50% inhibition of human C-reactive protein expression in this assay and are therefore preferred. More preferred are SEQ ID NOs 36, 22 and 56. The target regions to which these preferred sequences are complementary are herein referred to as "preferred target segments" and are therefore preferred for targeting by compounds of the present invention. These preferred target segments are shown in Table 4. These sequences are shown to contain thymine (T) but one of skill in the art will appreciate that thymine (T) is generally replaced by uracil (U) in RNA sequences. The sequences represent the reverse complement of the preferred antisense compounds shown in Table 1. "Target site" indicates the first (5'-most) nucleotide number on the particular target nucleic acid to which the oligonucleotide binds. Also shown in Table 4 is the species in which each of the preferred target segments was found.

In further embodiment of the present invention, a second series of antisense compounds was designed to target different regions of the human C-reactive protein RNA, using published sequences (GENBANK® accession number M11725.1, incorporated herein as SEQ ID NO:4). The compounds are shown in Table 2. "Target site" indicates the first (5'-most) nucleotide number on the particular target sequence to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE)nucleotides. The internucleoside (backbone) linkages are phosphorothioate (P=S) throughout the oligonucleotide. All cytidine residues are 5-methylcytidines.

The compounds were analyzed for their effect on human C-reactive protein mRNA levels by quantitative real-time PCR using a second set of probes and primer designed to hybridize to a human C-reactive protein sequence, using published sequence information (GENBANK® accession number M11725.1, incorporated herein as SEQ ID NO:4). For human C-reactive protein the PCR primers were:

forward primer: GCTTCCCCTCTTCCCGAA (SEQ ID NO:73)

reverse primer: TGCGCCACTATGTAAATAATTTTCC (SEQ ID NO:74) and the PCR probe was: FAM-TCTGA-CACCTGCCCCAACAAGCAATG-TAMRA (SEQ ID NO:75) where FAM is the fluorescent dye and TAMRA is the quencher dye. Data, shown in Table 2, are averages from three experiments in which cytokine-induced Hep3B cells were treated with 150 nM of the antisense oligonucleotides of the present invention. The positive control for each datapoint is identified in the table by sequence ID number. If present, "N.D." indicates "no data".

TABLE 2

Inhibition of human C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 140185 | 3' UTR | 4 | 1651 | acacctggccagtgtcctga | 37 | 61 | 1 |
| 140186 | 3' UTR | 4 | 1771 | cctttccagtgtgctttgag | 1 | 62 | 1 |
| 329883 | 3' UTR | 4 | 10 | gtcagagcttcgggaagagg | 6 | 76 | 1 |
| 329884 | 3' UTR | 4 | 37 | tttccaacattgcttgttgg | 0 | 77 | 1 |
| 329885 | 3' UTR | 4 | 47 | tgtaaataattttccaacat | 41 | 78 | 1 |
| 329886 | 3' UTR | 4 | 57 | tgcgccactatgtaaataat | 7 | 79 | 1 |
| 329887 | 3' UTR | 4 | 67 | taagggagtttgcgccacta | 40 | 80 | 1 |
| 329888 | 3' UTR | 4 | 77 | tccaaagcagtaagggagtt | 21 | 81 | 1 |
| 329889 | 3' UTR | 4 | 87 | tggatttatatccaaagcag | N.D. | 82 | |
| 329890 | 3' UTR | 4 | 94 | tcctgcctggatttatatcc | 8 | 83 | 1 |
| 329891 | 3' UTR | 4 | 107 | tagagctacctcctcctgcc | 1 | 84 | 1 |
| 329892 | 3' UTR | 4 | 122 | ccagatctcttgccttagag | 70 | 85 | 1 |
| 329893 | 3' UTR | 4 | 132 | gctagaagtcccagatctct | 38 | 86 | 1 |
| 329894 | 3' UTR | 4 | 157 | gatgtattcggctgaaagtt | 29 | 87 | 1 |
| 329895 | 3' UTR | 4 | 167 | ctttggaaaagatgtattcg | 22 | 88 | 1 |
| 329896 | 3' UTR | 4 | 191 | tgatacaagggcctgaattc | 30 | 89 | 1 |
| 329897 | Start codon | 4 | 206 | acgtcctgctgccagtgata | 44 | 90 | 1 |
| 329898 | Coding | 4 | 226 | acaacagcttctccatggtc | 43 | 91 | 1 |
| 329899 | Coding | 4 | 231 | gaaacacaacagcttctcca | 28 | 92 | 1 |
| 329900 | Coding | 4 | 241 | tcaagaccaagaaacacaac | 0 | 93 | 1 |
| 329901 | Coding | 4 | 251 | gagaggctggtcaagaccaa | 15 | 94 | 1 |

TABLE 2-continued

Inhibition of human C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 329902 | Coding | 4 | 258 | agcatgagagaggctggtca | 54 | 95 | 1 |
| 329903 | Coding | 4 | 268 | tctggccaaaagcatgagag | 48 | 96 | 1 |
| 329904 | Coding | 4 | 278 | cccttacctgtctggccaaa | 45 | 97 | 1 |
| 329905 | Coding | 4 | 283 | ggtggcccttacctgtctgg | 12 | 98 | 1 |
| 329906 | Coding | 4 | 318 | cccatacctcagatcaaaac | 0 | 99 | 1 |
| 329907 | Coding | 4 | 342 | gttcatgcagtcttagaccc | 21 | 100 | 1 |
| 329908 | Coding | 4 | 347 | agactgttcatgcagtctta | N.D. | 101 | |
| 329909 | Coding | 4 | 351 | tttgagactgttcatgcagt | 28 | 102 | 1 |
| 329910 | Coding | 4 | 381 | gttctgttcatacagtcttt | 16 | 103 | 1 |
| 329911 | Coding | 4 | 386 | ccactgttctgttcatacag | 0 | 104 | 1 |
| 329912 | Coding | 4 | 391 | atgctccactgttctgttca | 4 | 105 | 1 |
| 329913 | Coding | 4 | 396 | gaaggatgctccactgttct | 0 | 106 | 1 |
| 329914 | Coding | 4 | 401 | accatgaaggatgctccact | 49 | 107 | 1 |
| 329915 | Coding | 4 | 406 | cacacaccatgaaggatgct | 33 | 108 | 1 |
| 329916 | Coding | 4 | 411 | acacacacacaccatgaagg | 0 | 109 | 1 |
| 329917 | Coding | 4 | 449 | cccttctccagttacacacc | 3 | 110 | 1 |
| 329918 | Coding | 4 | 459 | acagactgacccctttctcca | 19 | 111 | 1 |
| 329919 | Coding | 4 | 469 | agattgagaaacagactgac | 52 | 112 | 1 |
| 329920 | Coding | 4 | 479 | atagaatttaagattgagaa | 8 | 113 | 1 |
| 329921 | Coding | 4 | 489 | tcacttacgtatagaattta | 0 | 114 | 1 |
| 329922 | Coding | 4 | 492 | ccctcacttacgtatagaat | 40 | 115 | 1 |
| 329923 | Coding | 4 | 499 | atctatcccctcacttacgt | 23 | 116 | 1 |
| 329924 | Coding | 4 | 510 | agatcacacagatctatccc | 6 | 117 | 1 |
| 329925 | Coding | 4 | 520 | gaggtttctcagatcacaca | 0 | 118 | 1 |
| 329926 | Coding | 4 | 530 | gcaaatgtgagaggtttctc | 4 | 119 | 1 |
| 329927 | Coding | 4 | 557 | cgacatgtctgtgagccaga | 39 | 120 | 1 |
| 329928 | Coding | 4 | 562 | ttcctcgacatgtctgtgag | 52 | 121 | 1 |
| 329929 | Coding | 4 | 567 | aagccttcctcgacatgtct | 81 | 122 | 1 |
| 329930 | Coding | 4 | 596 | ggaagtatccgactctttgg | 39 | 123 | 1 |
| 329931 | Coding | 4 | 605 | ggatacataggaagtatccg | 0 | 124 | 1 |
| 329932 | Coding | 4 | 615 | gtgctttgagggatacatag | 12 | 125 | 1 |
| 329933 | Coding | 4 | 625 | ttcgttaacggtgctttgag | 0 | 126 | 1 |
| 329934 | Coding | 4 | 635 | tttgagaggcttcgttaacg | 0 | 127 | 1 |
| 329935 | Coding | 4 | 645 | cagtgaaggctttgagaggc | 1 | 128 | 1 |
| 329936 | Coding | 4 | 655 | tggaggcacacagtgaaggc | 69 | 129 | 1 |

TABLE 2-continued

Inhibition of human C-reactive protein mRNA levels by
chimeric phosphorothioate oligonucleotides having 2'-MOE
wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 329937 | Coding | 4 | 660 | agaagtggaggcacacagtg | 0 | 130 | 1 |
| 329938 | Coding | 4 | 665 | cgtgtagaagtggaggcaca | 36 | 131 | 1 |
| 329939 | Coding | 4 | 675 | aggacagttccgtgtagaag | 40 | 132 | 1 |
| 329940 | Coding | 4 | 685 | ccacgggtcgaggacagttc | 46 | 133 | 1 |
| 329941 | Coding | 4 | 695 | aatactgtacccacgggtcg | 26 | 134 | 1 |
| 329942 | Coding | 4 | 716 | tctcttggtggcatacgaga | 55 | 135 | 1 |
| 329943 | Coding | 4 | 726 | cattgtcttgtctcttggtg | 70 | 136 | 1 |
| 329944 | Coding | 4 | 736 | atgagaatctcattgtcttg | 58 | 137 | 1 |
| 329945 | Coding | 4 | 746 | agaccaaaatatgagaatct | 6 | 138 | 1 |
| 329946 | Coding | 4 | 756 | ctatatccttagaccaaaat | 26 | 139 | 1 |
| 329947 | Coding | 4 | 765 | aactgtatcctatatcctta | 0 | 140 | 1 |
| 329948 | Coding | 4 | 775 | cccactgtaaaactgtatcc | 26 | 141 | 1 |
| 329949 | Coding | 4 | 785 | ttcagacccacccactgtaa | N.D. | 142 | |
| 329950 | Coding | 4 | 796 | tcgaataatatttcagaccc | 37 | 143 | 1 |
| 329951 | Coding | 4 | 806 | ttcaggaacctcgaataata | 14 | 144 | 1 |
| 329952 | Coding | 4 | 816 | ctactgtgacttcaggaacc | 59 | 145 | 1 |
| 329953 | Coding | 4 | 826 | tgtactggagctactgtgac | 39 | 146 | 1 |
| 329954 | Coding | 4 | 836 | tgtacaaatgtgtactggag | 60 | 147 | 1 |
| 329955 | Coding | 4 | 846 | actcccagcttgtacaaatg | 21 | 148 | 1 |
| 329956 | Coding | 4 | 856 | cctgaggcggactcccagct | 62 | 149 | 1 |
| 329957 | Coding | 4 | 860 | gatccctgaggcggactccc | 66 | 150 | 1 |
| 329958 | Coding | 4 | 870 | agaactccacgatccctgag | 30 | 151 | 1 |
| 329959 | Coding | 4 | 880 | ccatctacccagaactccac | 22 | 152 | 1 |
| 329960 | Coding | 4 | 890 | cctgggcttcccatctaccc | 34 | 153 | 1 |
| 329961 | Coding | 4 | 900 | tcttcctcaccctgggcttc | 52 | 154 | 1 |
| 329962 | Coding | 4 | 910 | ttcttcagactcttcctcac | 38 | 155 | 1 |
| 329963 | Coding | 4 | 920 | agtgtatcccttcttcagac | 39 | 156 | 1 |
| 329964 | Coding | 4 | 944 | gatgatgcttgcttctgccc | 55 | 157 | 1 |
| 329965 | Coding | 4 | 964 | gaatcctgctcctgccccaa | 37 | 158 | 1 |
| 329966 | Coding | 4 | 967 | aaggaatcctgctcctgccc | 55 | 159 | 1 |
| 329967 | Coding | 4 | 977 | gttcccaccgaaggaatcct | 26 | 160 | 1 |
| 329968 | Coding | 4 | 987 | ttccttcaaagttcccaccg | 59 | 161 | 1 |
| 329969 | Coding | 4 | 1000 | accagggactggcttccttc | 71 | 162 | 1 |
| 329970 | Coding | 4 | 1010 | aatgtctcccaccagggact | 7 | 163 | 1 |
| 329971 | Coding | 4 | 1020 | tcacatttccaatgtctccc | 56 | 164 | 1 |
| 329972 | Coding | 4 | 1030 | tcccacatgttcacatttcc | 49 | 165 | 1 |

TABLE 2-continued

Inhibition of human C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 329973 | Coding | 4 | 1040 | cagcacaaagtcccacatgt | 66 | 166 | 1 |
| 329974 | Coding | 4 | 1050 | catctggtgacagcacaaag | 65 | 167 | 1 |
| 329975 | Coding | 4 | 1060 | gtgttaatctcatctggtga | 47 | 168 | 1 |
| 329976 | Coding | 4 | 1070 | aagatagatggtgttaatct | 37 | 169 | 1 |
| 329977 | Coding | 4 | 1097 | caggacattaggactgaagg | 53 | 170 | 1 |
| 329978 | Coding | 4 | 1107 | cccgccagttcaggacatta | 52 | 171 | 1 |
| 329979 | Coding | 4 | 1117 | tacttcagtgcccgccagtt | 49 | 172 | 1 |
| 329980 | Coding | 4 | 1127 | ttgcacttcatacttcagtg | 69 | 173 | 1 |
| 329981 | Coding | 4 | 1137 | acacttcgccttgcacttca | 54 | 174 | 1 |
| 329982 | Coding | 4 | 1147 | ggtttggtgaacacttcgcc | 55 | 175 | 1 |
| 329983 | 3' UTR | 4 | 1193 | gggaggtaccttcaggaccc | 48 | 176 | 1 |
| 329984 | 3' UTR | 4 | 1235 | taccagagacagagacgtgg | 62 | 177 | 1 |
| 329985 | 3' UTR | 4 | 1245 | aagcgggaggtaccagagac | 62 | 178 | 1 |
| 329986 | 3' UTR | 4 | 1283 | gcccagagacagagacgtgg | 68 | 179 | 1 |
| 329987 | 3' UTR | 4 | 1293 | gggaacaaaggcccagagac | 59 | 180 | 1 |
| 329988 | 3' UTR | 4 | 1326 | tgaggagggtggagcaggcc | 44 | 181 | 1 |
| 329989 | 3' UTR | 4 | 1338 | attctcaggcgctgaggagg | 44 | 182 | 1 |
| 329990 | 3' UTR | 4 | 1348 | ctttacctccattctcaggc | 74 | 183 | 1 |
| 329991 | 3' UTR | 4 | 1358 | agaccagacactttacctcc | 29 | 184 | 1 |
| 329992 | 3' UTR | 4 | 1368 | acgagctcccagaccagaca | 70 | 185 | 1 |
| 329993 | 3' UTR | 4 | 1378 | agcatagttaacgagctccc | 64 | 186 | 1 |
| 329994 | 3' UTR | 4 | 1388 | accatttcccagcatagtta | 34 | 187 | 1 |
| 329995 | 3' UTR | 4 | 1398 | attcttttggaccatttccc | 35 | 188 | 1 |
| 329996 | 3' UTR | 4 | 1408 | tcaaattctgattcttttgg | 27 | 189 | 1 |
| 329997 | 3' UTR | 4 | 1451 | ccaagatctgtccaacttga | 55 | 190 | 1 |
| 329998 | 3' UTR | 4 | 1471 | tgtgaggtaagaaattatct | 21 | 191 | 1 |
| 329999 | 3' UTR | 4 | 1481 | ttctcatctatgtgaggtaa | 74 | 192 | 1 |
| 330000 | 3' UTR | 4 | 1491 | ggtgttagttttctcatcta | 63 | 193 | 1 |
| 330001 | 3' UTR | 4 | 1501 | ctcctttctgggtgttagtt | 70 | 194 | 1 |
| 330002 | 3' UTR | 4 | 1511 | aacatcatttctcctttctg | 41 | 195 | 1 |
| 330003 | 3' UTR | 4 | 1536 | agctcttgccttatgagttt | 58 | 196 | 1 |
| 330004 | 3' UTR | 4 | 1546 | cttccttctcagctcttgcc | 57 | 197 | 1 |
| 330005 | 3' UTR | 4 | 1556 | aagatcagcgcttccttctc | 69 | 198 | 1 |
| 330006 | 3' UTR | 4 | 1566 | aattaaatagaagatcagcg | 57 | 199 | 1 |
| 330007 | 3' UTR | 4 | 1621 | gaagagccctgtgaatgtgg | 24 | 200 | 1 |

TABLE 2-continued

Inhibition of human C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 330008 | 3' UTR | 4 | 1641 | agtgtcctgattctgagact | 53 | 201 | 1 |
| 330009 | 3' UTR | 4 | 1661 | cccaaaccagacacctggcc | 75 | 202 | 1 |
| 330010 | 3' UTR | 4 | 1681 | atgatgatgagcactctgga | 59 | 203 | 1 |
| 330011 | 3' UTR | 4 | 1691 | gttctatgacatgatgatga | 59 | 204 | 1 |
| 330012 | 3' UTR | 4 | 1719 | tcccatttcaggagacctgg | 60 | 205 | 1 |
| 330013 | 3' UTR | 4 | 1729 | ttgctgggcttcccatttca | 39 | 206 | 1 |
| 330014 | 3' UTR | 4 | 1739 | ctgcgtggtattgctgggct | 64 | 207 | 1 |
| 330015 | 3' UTR | 4 | 1749 | agtggagggactgcgtggta | 60 | 208 | 1 |
| 330016 | 3' UTR | 4 | 1761 | gtgctttgagaaagtggagg | 69 | 209 | 1 |
| 330017 | 3' UTR | 4 | 1781 | attctaatggcctttccagt | 61 | 210 | 1 |
| 330018 | 3' UTR | 4 | 1805 | aagcagatctgctctgctgg | 52 | 211 | 1 |
| 330019 | 3' UTR | 4 | 1840 | atttatacctagtgcttcat | 53 | 212 | 1 |
| 330020 | 3' UTR | 4 | 1850 | gtaacaacatatttatacct | 15 | 213 | 1 |
| 330021 | 3' UTR | 4 | 1860 | gttcttggcagtaacaacat | 74 | 214 | 1 |
| 330022 | 3' UTR | 4 | 1870 | agtcatttaagttcttggca | 67 | 215 | 1 |
| 330023 | 3' UTR | 4 | 1923 | agtttcccagaagagccata | 45 | 216 | 1 |
| 330024 | 3' UTR | 4 | 1952 | cccacaaggttcgtgtggaa | 53 | 217 | 1 |
| 330025 | 3' UTR | 4 | 1962 | aattcacagccccacaaggt | 2 | 218 | 1 |
| 330026 | 3' UTR | 4 | 1972 | atgaagaaagaattcacagc | 29 | 219 | 1 |
| 330027 | 3' UTR | 4 | 2003 | cttgtggcctgggtatattg | 59 | 220 | 1 |
| 330028 | 3' UTR | 4 | 2013 | cacgtccactcttgtggcct | 69 | 221 | 1 |
| 330029 | 3' UTR | 4 | 2023 | ccctgtggttcacgtccact | 63 | 222 | 1 |
| 330030 | 3' UTR | 4 | 2033 | tgacaggacaccctgtggtt | 29 | 223 | 1 |
| 330031 | 3' UTR | 4 | 2043 | tgggctcctctgacaggaca | 66 | 224 | 1 |
| 330032 | 3' UTR | 4 | 2043 | tcctccagatagggagctgg | N.D. | 225 | |
| 330033 | 3' UTR | 4 | 2085 | tatccaactatcctccagat | 31 | 226 | 1 |
| 330034 | 3' UTR | 4 | 2095 | aacacgtaactatccaacta | 27 | 227 | 1 |
| 330035 | 3' UTR | 4 | 2105 | tcctgctaggaacacgtaac | 72 | 228 | 1 |
| 330036 | 3' UTR | 4 | 2115 | ctgtagttggtcctgctagg | 56 | 229 | 1 |
| 330037 | 3' UTR | 4 | 2126 | ccttgggaagactgtagttg | 34 | 230 | 1 |
| 330038 | 3' UTR | 4 | 2136 | ataactcaatccttgggaag | 27 | 231 | 1 |
| 330039 | 3' UTR | 4 | 2146 | cccaaagtccataactcaat | 22 | 232 | 1 |
| 330040 | 3' UTR | 4 | 2156 | atgtctcactcccaaagtcc | 36 | 233 | 1 |
| 330041 | 3' UTR | 4 | 2166 | cagcaagaagatgtctcact | 50 | 234 | 1 |
| 330042 | 3' UTR | 4 | 2176 | ggaaatccagcagcaagaag | 48 | 235 | 1 |
| 330043 | 3' UTR | 4 | 2186 | ctctcagcttggaaatccag | 57 | 236 | 1 |

TABLE 2-continued

Inhibition of human C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 330044 | 3' UTR | 4 | 2196 | ggttcacgtcctctcagctt | 76 | 237 | 1 |
| 330045 | 3' UTR | 4 | 2205 | gtggtcccaggttcacgtcc | 50 | 238 | 1 |
| 330046 | 3' UTR | 4 | 2215 | atggctactggtggtcccag | N.D. | 239 | |
| 330047 | 3' UTR | 4 | 2225 | ggcaaacaagatggctactg | 56 | 240 | 1 |
| 330048 | 3' UTR | 4 | 2235 | ctctccatgtggcaaacaag | 53 | 241 | 1 |
| 330049 | 3' UTR | 4 | 2245 | ctcacagtctctctccatgt | 58 | 242 | 1 |
| 330050 | 3' UTR | 4 | 2255 | ggcttctgtcctcacagtct | 50 | 243 | 1 |
| 330051 | 3' UTR | 4 | 2265 | cttccagtttggcttctgtc | 65 | 244 | 1 |
| 330052 | 3' UTR | 4 | 2275 | ggctcctccacttccagttt | 71 | 245 | 1 |
| 330053 | 3' UTR | 4 | 2285 | tcaatcccttggctcctcca | 53 | 246 | 1 |
| 330054 | 3' UTR | 4 | 2295 | ctgttgtttgtcaatccctt | 61 | 247 | 1 |
| 330055 | 3' UTR | 4 | 2305 | ggtcaaggctctgttgtttg | 30 | 248 | 1 |
| 330056 | 3' UTR | 4 | 2315 | gactccacgtggtcaaggct | 79 | 249 | 1 |
| 330057 | 3' UTR | 4 | 2325 | ctgattcagagactccacgt | 69 | 250 | 1 |
| 330058 | 3' UTR | 4 | 2335 | ccagacaaggctgattcaga | 45 | 251 | 1 |
| 330059 | 3' UTR | 4 | 2345 | agatctggttccagacaagg | 59 | 252 | 1 |
| 330060 | 3' UTR | 4 | 2355 | gtccaggtgtagatctggtt | 53 | 253 | 1 |
| 330061 | 3' UTR | 4 | 2365 | gacctgggcagtccaggtgt | 38 | 254 | 1 |
| 330062 | 3' UTR | 4 | 2378 | ttattggcttatagacctgg | 56 | 255 | 1 |
| 330063 | 3' UTR | 4 | 2410 | acagcttggactcactcaag | 30 | 256 | 1 |
| 330064 | 3' UTR | 4 | 2432 | cttctaaagcaactatcaga | 10 | 257 | 1 |
| 330065 | 3' UTR | 4 | 2442 | ttagtcacaacttctaaagc | 13 | 258 | 1 |
| 330066 | 3' UTR | 4 | 2452 | catagagaagttagtcacaa | 22 | 259 | 1 |

As shown in Table 2, SEQ ID NOs 85, 95, 112, 121, 122, 129, 135, 136, 137, 145, 147, 149, 150, 154, 157, 159, 161, 162, 164, 166, 167, 170, 171, 173, 174, 175, 177, 178, 179, 180, 183, 185, 186, 190, 192, 193, 194, 196, 197, 198, 199, 201, 202, 203, 204, 205, 207, 208, 209, 210, 211, 212, 214, 215, 217, 220, 221, 222, 224, 228, 229, 234, 236, 237, 238, 240, 241, 242, 243, 244, 245, 246, 247, 249, 250, 252, 253 and 255 demonstrated at least 50% inhibition of human C-reactive protein expression in this assay and are therefore preferred. The target regions to which these preferred sequences are complementary are herein referred to as "preferred target segments" and are therefore preferred for targeting by compounds of the present invention. These preferred target segments are shown in Table 4. These sequences are shown to contain thymine (T) but one of skill in the art will appreciate that thymine (T) is generally replaced by uracil (U) in RNA sequences. The sequences represent the reverse complement of the preferred antisense compounds shown in Table 2. "Target site" indicates the first (5'-most) nucleotide number on the particular target nucleic acid to which the oligonucleotide binds. Also shown in Table 4 is the species in which each of the preferred target segments was found.

Example 16

Antisense Inhibition of Rat C-Reactive Protein Expression by Chimeric Phosphorothioate Oligonucleotides Having 2'-MOE Wings and a Deoxy Gap In accordance with the present invention, a series of antisense compounds was designed to target different regions of the rat C-reactive protein RNA, using published sequences (GENBANK® accession number M83176.1, incorporated herein as SEQ ID NO:11). The compounds are shown in Table 3. "Target site" indicates the first (5'-most) nucleotide number on the particular target nucleic acid to which the compound binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE)nucleotides. The internucleoside (backbone) linkages are phosphorothioate (P=S) throughout the oligonucleotide. All cytidine residues are 5-methylcytidines.

The compounds were analyzed for their effect on rat C-reactive protein mRNA levels by quantitative real-time PCR as described in other examples herein. Data, shown in Table 3, are averages from three experiments in which primary rat hepatocytes were treated with 150 nM of the antisense oligonucleotides of the present invention. If present, "N.D." indicates "no data".

TABLE 3

Inhibition of rat C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 197163 | Start Codon | 11 | 1 | caccatagtagcttctccat | 26 | 260 |
| 197164 | Coding | 11 | 21 | agcttatcgtgatcagaaga | 27 | 261 |
| 197165 | Coding | 11 | 41 | atgaccaaaagcctgagaga | 26 | 262 |
| 197166 | Coding | 11 | 61 | gcctgtttagacatgtcttc | 57 | 263 |
| 197167 | Coding | 11 | 81 | acactccgggaaatacgaag | 47 | 264 |
| 197168 | Coding | 11 | 101 | ggacacataggcagtagctg | 61 | 265 |
| 197169 | Coding | 11 | 121 | ttctttgactctgcttccag | 36 | 266 |
| 197170 | Coding | 11 | 141 | cagtgaaggcttccagtggc | 56 | 267 |
| 197171 | Coding | 11 | 161 | agcgtgggcatagagacaca | 48 | 268 |
| 197172 | Coding | 11 | 181 | ctgaagcttcggctcacatc | 23 | 269 |
| 197173 | Coding | 11 | 201 | tggtagcgtaagagaagatg | 26 | 270 |
| 197174 | Coding | 11 | 221 | aatctcgttaaagctcgtct | 34 | 271 |
| 197175 | Coding | 11 | 261 | ctgcaatactaaacccttga | 38 | 272 |
| 197176 | Coding | 11 | 281 | cagtatttcaggcccaccta | 39 | 273 |
| 197177 | Coding | 11 | 301 | ggaatttctgaagcactgaa | 30 | 274 |
| 197178 | Coding | 11 | 320 | gatgtgtgttggtacctcag | 21 | 275 |
| 197179 | Coding | 11 | 411 | caatgtagcccttctgcaga | 48 | 276 |
| 197180 | Coding | 11 | 431 | gatgcttgcatttgtcccca | 51 | 277 |
| 197181 | Coding | 11 | 451 | tcctgctcctgcccaagat | 19 | 278 |
| 197182 | Coding | 11 | 471 | caaagccaccgccatacgag | 28 | 279 |
| 197183 | Coding | 11 | 491 | caccaaagactgattcgcgt | 14 | 280 |
| 197184 | Coding | 11 | 511 | ttcacatctccaatgtctcc | 35 | 281 |
| 197185 | Coding | 11 | 531 | atagcacaaagtcccacatg | 53 | 282 |
| 197186 | Coding | 11 | 551 | tgcattgatctgttctggag | 37 | 283 |
| 197187 | Coding | 11 | 571 | aataccctaccaacatagac | 47 | 284 |
| 197188 | Coding | 11 | 601 | agtgcccgccagttcaaaac | 40 | 285 |
| 197189 | Coding | 11 | 621 | caccgtgtgtttcatacttc | 31 | 286 |
| 197190 | Coding | 11 | 641 | ctgcggcttgataaacacat | 21 | 287 |
| 197191 | Coding | 11 | 661 | cagtcagtcaagggccacag | 43 | 288 |
| 197192 | Coding | 11 | 671 | ggactcacaacagtcagtca | 35 | 289 |

TABLE 3-continued

Inhibition of rat C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|

As shown in Table 3, SEQ ID NOs 260, 261, 262, 263, 264, 265, 266, 267, 268, 270, 271, 272, 273, 274, 276, 277, 279, 281, 282, 283, 284, 285, 286, 288 and 289 demonstrated at least 25% inhibition of rat C-reactive protein expression in this experiment and are therefore preferred. The target regions to which these preferred sequences are complementary are herein referred to as "preferred target segments" and are therefore preferred for targeting by compounds of the present invention. These preferred target segments are shown in Table 4. These sequences are shown to contain thymine (T) but one of skill in the art will appreciate that thymine (T) is generally replaced by uracil (U) in RNA sequences. The sequences represent the reverse complement of the preferred antisense compounds shown in Tables 1, 2 and 3. "Target site" indicates the first (5'-most) nucleotide-number on the particular target nucleic acid to which the oligonucleotide binds. Also shown in Table 4 is the species in which each of the preferred target segments was found.

TABLE 4

Sequence and position of preferred target segments identified in C-reactive protein.

| SITE ID | TARGET SEQ ID NO | TARGET SITE | SEQUENCE | REV COMP OF SEQ ID | ACTIVE IN | SEQ ID NO |
|---|---|---|---|---|---|---|
| 44586 | 11 | 16 | cccgaagctctgacacctgc | 19 | H. sapiens | 290 |
| 44587 | 11 | 71 | ggcgcaaactcccttactgc | 20 | H. sapiens | 291 |
| 44588 | 11 | 181 | ccaaaggagtgaattcaggc | 21 | H. sapiens | 292 |
| 44589 | 11 | 221 | gacgtgaccatggagaagct | 22 | H. sapiens | 293 |
| 44590 | 11 | 281 | ggccagacaggtaagggcca | 23 | H. sapiens | 294 |
| 44592 | 11 | 341 | ggggtctaagactgcatgaa | 25 | H. sapiens | 295 |
| 44593 | 11 | 551 | tgttttctggctcacagac | 26 | H. sapiens | 296 |
| 44594 | 11 | 701 | gtgggtacagtattttctcg | 27 | H. sapiens | 297 |
| 44595 | 11 | 781 | agttttacagtgggtgggtc | 28 | H. sapiens | 298 |
| 44596 | 11 | 871 | tcagggatcgtggagttctg | 29 | H. sapiens | 299 |
| 44597 | 11 | 1091 | gcgggcccttcagtcctaat | 30 | H. sapiens | 300 |
| 44598 | 11 | 1171 | ctgtggccctgaggccagct | 31 | H. sapiens | 301 |
| 44599 | 11 | 1191 | gtgggtcctgaaggtacctc | 32 | H. sapiens | 302 |
| 44600 | 11 | 1361 | ggtaaagtgtctggtctggg | 33 | H. sapiens | 303 |
| 44601 | 11 | 1391 | ctatgctgggaaatggtcca | 34 | H. sapiens | 304 |
| 44603 | 11 | 1671 | ctggtttgggtccagagtgc | 36 | H. sapiens | 305 |
| 44604 | 11 | 1711 | tgctgggcccaggtctcctg | 37 | H. sapiens | 306 |
| 44606 | 11 | 1961 | aaccttgtggggctgtgaat | 39 | H. sapiens | 307 |
| 44607 | 11 | 2161 | ttgggagtgagacatcttct | 40 | H. sapiens | 308 |
| 44608 | 11 | 2291 | agccaagggattgacaaaca | 41 | H. sapiens | 309 |
| 44609 | 11 | 2431 | ttctgatagttgctttagaa | 42 | H. sapiens | 310 |
| 53590 | 11 | 111 | ggaggaggtagctctaaggc | 43 | H. sapiens | 311 |
| 53589 | 11 | 201 | ccttgtatcactggcagcag | 44 | H. sapiens | 312 |

TABLE 4-continued

Sequence and position of preferred target segments identified in C-reactive protein.

| SITE ID | TARGET SEQ ID NO | TARGET SITE | SEQUENCE | REV COMP OF SEQ ID | ACTIVE IN | SEQ ID NO |
|---|---|---|---|---|---|---|
| 53587 | 11 | 451 | tgtgtaactggagaaggggt | 46 | H. sapiens | 313 |
| 53585 | 11 | 761 | ggtctaaggatataggatac | 48 | H. sapiens | 314 |
| 53584 | 11 | 821 | ctgaagtcacagtagctcca | 49 | H. sapiens | 315 |
| 53583 | 11 | 861 | ggagtccgcctcagggatcg | 50 | H. sapiens | 316 |
| 53582 | 11 | 901 | aagcccagggtgaggaagag | 51 | H. sapiens | 317 |
| 53581 | 11 | 921 | tctgaagaagggatacactg | 52 | H. sapiens | 318 |
| 53580 | 11 | 951 | agcaagcatcatcttggggc | 53 | H. sapiens | 319 |
| 53579 | 11 | 1031 | gaaatgtgaacatgtgggac | 54 | H. sapiens | 320 |
| 53578 | 11 | 1111 | gtcctgaactggcgggcact | 55 | H. sapiens | 321 |
| 53577 | 11 | 1141 | gtgcaaggcgaagtgttcac | 56 | H. sapiens | 322 |
| 53576 | 11 | 1341 | cctcagcgcctgagaatgga | 57 | H. sapiens | 323 |
| 53574 | 11 | 1551 | gagctgagaaggaagcgctg | 59 | H. sapiens | 324 |
| 53573 | 11 | 1611 | ggagcattgcccacattcac | 60 | H. sapiens | 325 |
| 53572 | 11 | 1651 | tcaggacactggccaggtgt | 61 | H. sapiens | 326 |
| 53571 | 11 | 1771 | ctcaaagcacactggaaagg | 62 | H. sapiens | 327 |
| 53570 | 11 | 1831 | cagcgcaaaatgaagcacta | 63 | H. sapiens | 328 |
| 53569 | 11 | 1971 | ggctgtgaattctttcttca | 64 | H. sapiens | 329 |
| 53568 | 11 | 2041 | ggtgtcctgtcagaggagcc | 65 | H. sapiens | 330 |
| 53567 | 11 | 2101 | gatagttacgtgttcctagc | 66 | H. sapiens | 331 |
| 53565 | 11 | 2211 | gaacctgggaccaccagtag | 68 | H. sapiens | 332 |
| 53564 | 11 | 2271 | agccaaactggaagtggagg | 69 | H. sapiens | 333 |
| 53563 | 11 | 2341 | tcagccttgtctggaaccag | 70 | H. sapiens | 334 |
| 53562 | 11 | 2402 | cctgtttacttgagtgagtc | 71 | H. sapiens | 335 |
| 246578 | 11 | 122 | ctctaaggcaagagatctgg | 85 | H. sapiens | 336 |
| 246588 | 11 | 258 | tgaccagcctctctcatgct | 95 | H. sapiens | 337 |
| 246605 | 11 | 469 | gtcagtctgtttctcaatct | 112 | H. sapiens | 338 |
| 246614 | 11 | 562 | ctcacagacatgtcgaggaa | 121 | H. sapiens | 339 |
| 246615 | 11 | 567 | agacatgtcgaggaaggctt | 122 | H. sapiens | 340 |
| 246622 | 11 | 655 | gccttcactgtgtgcctcca | 129 | H. sapiens | 341 |
| 246628 | 11 | 716 | tctcgtatgccaccaagaga | 135 | H. sapiens | 342 |
| 246629 | 11 | 726 | caccaagagacaagacaatg | 136 | H. sapiens | 343 |
| 246630 | 11 | 736 | caagacaatgagattctcat | 137 | H. sapiens | 344 |
| 246638 | 11 | 816 | ggttcctgaagtcacagtag | 145 | H. sapiens | 345 |
| 246640 | 11 | 836 | ctccagtacacatttgtaca | 147 | H. sapiens | 346 |
| 246642 | 11 | 856 | agctgggagtccgcctcagg | 149 | H. sapiens | 347 |
| 246643 | 11 | 860 | gggagtccgcctcagggatc | 150 | H. sapiens | 348 |

TABLE 4-continued

Sequence and position of preferred target segments identified in C-reactive protein.

| SITE ID | TARGET SEQ ID NO | TARGET SITE | SEQUENCE | REV COMP OF SEQ ID | ACTIVE IN | SEQ ID NO |
|---|---|---|---|---|---|---|
| 246647 | 11 | 900 | gaagcccagggtgaggaaga | 154 | H. sapiens | 349 |
| 246650 | 11 | 944 | gggcagaagcaagcatcatc | 157 | H. sapiens | 350 |
| 246652 | 11 | 967 | gggcaggagcaggattcctt | 159 | H. sapiens | 351 |
| 246654 | 11 | 987 | cggtgggaactttgaaggaa | 161 | H. sapiens | 352 |
| 246655 | 11 | 1000 | gaaggaagccagtccctggt | 162 | H. sapiens | 353 |
| 246657 | 11 | 1020 | gggagacattggaaatgtga | 164 | H. sapiens | 354 |
| 246659 | 11 | 1040 | acatgtgggactttgtgctg | 166 | H. sapiens | 355 |
| 246660 | 11 | 1050 | ctttgtgctgtcaccagatg | 167 | H. sapiens | 356 |
| 246663 | 11 | 1097 | ccttcagtcctaatgtcctg | 170 | H. sapiens | 357 |
| 246664 | 11 | 1107 | taatgtcctgaactggcggg | 171 | H. sapiens | 358 |
| 246666 | 11 | 1127 | cactgaagtatgaagtgcaa | 173 | H. sapiens | 359 |
| 246667 | 11 | 1137 | tgaagtgcaaggcgaagtgt | 174 | H. sapiens | 360 |
| 246668 | 11 | 1147 | ggcgaagtgttcaccaaacc | 175 | H. sapiens | 361 |
| 246670 | 11 | 1235 | ccacgtctctgtctctggta | 177 | H. sapiens | 362 |
| 246671 | 11 | 1245 | gtctctggtacctcccgctt | 178 | H. sapiens | 363 |
| 246672 | 11 | 1283 | ccacgtctctgtctctgggc | 179 | H. sapiens | 364 |
| 246673 | 11 | 1293 | gtctctgggcctttgttccc | 180 | H. sapiens | 365 |
| 246676 | 11 | 1348 | gcctgagaatggaggtaaag | 183 | H. sapiens | 366 |
| 246678 | 11 | 1368 | tgtctggtctgggagctcgt | 185 | H. sapiens | 367 |
| 246679 | 11 | 1378 | gggagctcgttaactatgct | 186 | H. sapiens | 368 |
| 246683 | 11 | 1451 | tcaagttggacagatcttgg | 190 | H. sapiens | 369 |
| 246685 | 11 | 1481 | ttacctcacatagatgagaa | 192 | H. sapiens | 370 |
| 246686 | 11 | 1491 | tagatgagaaaactaacacc | 193 | H. sapiens | 371 |
| 246687 | 11 | 1501 | aactaacacccagaaaggag | 194 | H. sapiens | 372 |
| 246689 | 11 | 1536 | aaactcataaggcaagagct | 196 | H. sapiens | 373 |
| 246690 | 11 | 1546 | ggcaagagctgagaaggaag | 197 | H. sapiens | 374 |
| 246691 | 11 | 1556 | gagaaggaagcgctgatctt | 198 | H. sapiens | 375 |
| 246692 | 11 | 1566 | cgctgatcttctatttaatt | 199 | H. sapiens | 376 |
| 246694 | 11 | 1641 | agtctcagaatcaggacact | 201 | H. sapiens | 377 |
| 246695 | 11 | 1661 | ggccaggtgtctggtttggg | 202 | H. sapiens | 378 |
| 246696 | 11 | 1681 | tccagagtgctcatcatcat | 203 | H. sapiens | 379 |
| 246697 | 11 | 1691 | tcatcatcatgtcatagaac | 204 | H. sapiens | 380 |
| 246698 | 11 | 1719 | ccaggtctcctgaaatggga | 205 | H. sapiens | 381 |
| 246700 | 11 | 1739 | agcccagcaataccacgcag | 207 | H. sapiens | 382 |
| 246701 | 11 | 1749 | taccacgcagtccctccact | 208 | H. sapiens | 383 |
| 246702 | 11 | 1761 | cctccactttctcaaagcac | 209 | H. sapiens | 384 |

TABLE 4-continued

Sequence and position of preferred target segments identified in C-reactive protein.

| SITE ID | TARGET SEQ ID NO | TARGET SITE | SEQUENCE | REV COMP OF SEQ ID | ACTIVE IN | SEQ ID NO |
|---|---|---|---|---|---|---|
| 246703 | 11 | 1781 | actggaaaggccattagaat | 210 | H. sapiens | 385 |
| 246704 | 11 | 1805 | ccagcagagcagatctgctt | 211 | H. sapiens | 386 |
| 246705 | 11 | 1840 | atgaagcactaggtataaat | 212 | H. sapiens | 387 |
| 246707 | 11 | 1860 | atgttgttactgccaagaac | 214 | H. sapiens | 388 |
| 246708 | 11 | 1870 | tgccaagaacttaaatgact | 215 | H. sapiens | 389 |
| 246710 | 11 | 1952 | ttccacacgaaccttgtggg | 217 | H. sapiens | 390 |
| 246713 | 11 | 2003 | caatatacccaggccacaag | 220 | H. sapiens | 391 |
| 246714 | 11 | 2013 | aggccacaagagtggacgtg | 221 | H. sapiens | 392 |
| 246715 | 11 | 2023 | agtggacgtgaaccacaggg | 222 | H. sapiens | 393 |
| 246717 | 11 | 2043 | tgtcctgtcagaggagccca | 224 | H. sapiens | 394 |
| 246721 | 11 | 2105 | gttacgtgttcctagcagga | 228 | H. sapiens | 395 |
| 246722 | 11 | 2115 | cctagcaggaccaactacag | 229 | H. sapiens | 396 |
| 246727 | 11 | 2166 | agtgagacatcttcttgctg | 234 | H. sapiens | 397 |
| 246729 | 11 | 2186 | ctggatttccaagctgagag | 236 | H. sapiens | 398 |
| 246730 | 11 | 2196 | aagctgagaggacgtgaacc | 237 | H. sapiens | 399 |
| 246731 | 11 | 2205 | ggacgtgaacctgggaccac | 238 | H. sapiens | 400 |
| 246733 | 11 | 2225 | cagtagccatcttgtttgcc | 240 | H. sapiens | 401 |
| 246734 | 11 | 2235 | cttgtttgccacatggagag | 241 | H. sapiens | 402 |
| 246735 | 11 | 2245 | acatggagagagactgtgag | 242 | H. sapiens | 403 |
| 246736 | 11 | 2255 | agactgtgaggacagaagcc | 243 | H. sapiens | 404 |
| 246737 | 11 | 2265 | gacagaagccaaactggaag | 244 | H. sapiens | 405 |
| 246738 | 11 | 2275 | aaactggaagtggaggagcc | 245 | H. sapiens | 406 |
| 246739 | 11 | 2285 | tggaggagccaagggattga | 246 | H. sapiens | 407 |
| 246740 | 11 | 2295 | aagggattgacaaacaacag | 247 | H. sapiens | 408 |
| 246742 | 11 | 2315 | agccttgaccacgtggagtc | 249 | H. sapiens | 409 |
| 246743 | 11 | 2325 | acgtggagtctctgaatcag | 250 | H. sapiens | 410 |
| 246745 | 11 | 2345 | ccttgtctggaaccagatct | 252 | H. sapiens | 411 |
| 246746 | 11 | 2355 | aaccagatctacacctggac | 253 | H. sapiens | 412 |
| 246748 | 11 | 2378 | ccaggtctataagccaataa | 255 | H. sapiens | 413 |
| 115255 | 252 | 1 | atggagaagctactatggtg | 260 | R. norvegicus | 414 |
| 115256 | 252 | 21 | tcttctgatcacgataagct | 261 | R. norvegicus | 415 |
| 115257 | 252 | 41 | tctctcaggcttttggtcat | 262 | R. norvegicus | 416 |
| 115258 | 252 | 61 | gaagacatgtctaaacaggc | 263 | R. norvegicus | 417 |
| 115259 | 252 | 81 | cttcgtatttcccggagtgt | 264 | R. norvegicus | 418 |
| 115260 | 252 | 101 | cagctactgcctatgtgtcc | 265 | R. norvegicus | 419 |
| 115261 | 252 | 121 | ctggaagcagagtcaaagaa | 266 | R. norvegicus | 420 |

TABLE 4-continued

Sequence and position of preferred target segments identified in C-reactive protein.

| SITE ID | TARGET SEQ ID NO | TARGET SITE | SEQUENCE | REV COMP OF SEQ ID | ACTIVE IN | SEQ ID NO |
|---|---|---|---|---|---|---|
| 115262 | 252 | 141 | gccactggaagccttcactg | 267 | R. norvegicus | 421 |
| 115263 | 252 | 161 | tgtgtctctatgcccacgct | 268 | R. norvegicus | 422 |
| 115265 | 252 | 201 | catcttctcttacgctacca | 270 | R. norvegicus | 423 |
| 115266 | 252 | 221 | agacgagctttaacgagatt | 271 | R. norvegicus | 424 |
| 115267 | 252 | 261 | tcaagggtttagtattgcag | 272 | R. norvegicus | 425 |
| 115268 | 252 | 281 | taggtgggcctgaaatactg | 273 | R. norvegicus | 426 |
| 115269 | 252 | 301 | ttcagtgcttcagaaattcc | 274 | R. norvegicus | 427 |
| 115271 | 252 | 411 | tctgcagaagggctacattg | 276 | R. norvegicus | 428 |
| 115272 | 252 | 431 | tggggacaaatgcaagcatc | 277 | R. norvegicus | 429 |
| 115274 | 252 | 471 | ctcgtatggcggtggctttg | 279 | R. norvegicus | 430 |
| 115276 | 252 | 511 | ggagacattggagatgtgaa | 281 | R. norvegicus | 431 |
| 115277 | 252 | 531 | catgtgggactttgtgctat | 282 | R. norvegicus | 432 |
| 115278 | 252 | 551 | ctccagaacagatcaatgca | 283 | R. norvegicus | 433 |
| 115279 | 252 | 571 | gtctatgttggtagggtatt | 284 | R. norvegicus | 434 |
| 115280 | 252 | 601 | gttttgaactggcgggcact | 285 | R. norvegicus | 435 |
| 115281 | 252 | 621 | gaagtatgaaacacacggtg | 286 | R. norvegicus | 436 |
| 115283 | 252 | 661 | ctgtggcccttgactgactg | 288 | R. norvegicus | 437 |
| 115284 | 252 | 671 | Tgactgactgttgtgagtcc | 289 | R. norvegicus | 438 |

As these "preferred target segments" have been found by experimentation to be open to, and accessible for, hybridization with the antisense compounds of the present invention, one of skill in the art armed with the knowledge of the present invention will recognize or be able to ascertain, using no more than routine experimentation, further embodiments of the invention that encompass other compounds that specifically hybridize to these preferred target segments and consequently inhibit the expression of C-reactive protein.

According to the present invention, antisense compounds include antisense oligomeric compounds, antisense oligonucleotides, siRNAs, external guide sequence (EGS) oligonucleotides, alternate splicers, and other short oligomeric compounds that hybridize to at least a portion of the target nucleic acid.

Example 17

Western Blot Analysis of C-Reactive Protein Protein Levels

Western blot analysis (immunoblot analysis) is carried out using standard methods. Cells are harvested 16-20 hours after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to C-reactive protein is used, with a radiolabeled or fluorescently labeled secondary antibody directed against the primary antibody species. Bands are visualized using a PHOSPHORIMAGER™ instrument (Molecular Dynamics, Sunnyvale Calif.).

Example 18

Antisense Inhibition of Rabbit C-Reactive Protein Expression by Chimeric Phosphorothioate Oligonucleotides Having 2'-MOE Wings and a Deoxy Gap In accordance with the present invention, a series of antisense compounds was designed to target different regions of the rabbit C-reactive protein RNA, using published sequences (GENBANK® accession number M13497.1, incorporated herein as SEQ ID NO:439). The compounds are shown in Table 5. "Target site" indicates the first (5'-most) nucleotide number on the particular target nucleic acid to which the compound binds. All compounds in Table 5 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE)nucleotides. The internucleoside (backbone) linkages are phosphorothioate (P=S) throughout the oligonucleotide. All cytidine residues are 5-methylcytidines.

The compounds were analyzed for their effect on rabbit C-reactive protein mRNA levels by quantitative real-time PCR as described in other examples herein. Probes and primers to rabbit C-reactive protein were designed to hybridize to a rabbit C-reactive protein sequence, using published sequence information (GENBANK® accession number M13497.1, incorporated herein as SEQ ID NO:439). For rabbit C-reactive protein the PCR primers were:

forward primer: GGCGCGAGCTGACATATCA (SEQ ID NO:440)

reverse primer: CTTGGCAGAGCTCAGGGC (SEQ ID NO:441) and the PCR probe was: FAM-TACGTGGTGAAG-TACATGTCAAGCCCCAG-TAMRA (SEQ ID NO:442) where FAM is the fluorescent reporter dye and TAMRA is the quencher dye. For rabbit GAPDH the PCR primers were:

forward primer: TGTTCTAGAGACAGCCGCATCTT (SEQ ID NO:443)

reverse primer: CACCGACCTTCACCATCTTGT (SEQ ID NO:444) and the PCR probe was: 5' JOE-TTGTGCAGTGC-CAGCCTCGTCTCA-TAMRA 3' (SEQ ID NO:445) where JOE is the fluorescent reporter dye and TAMRA is the quencher dye. Data, shown in Table 5, are averages from three experiments in which primary rabbit hepatocytes were treated with 10 nM of the antisense oligonucleotides of the present invention. If present, "N.D." indicates "no data".

TABLE 5

Inhibition of rabbit C-reactive protein mRNA levels by chimeric phosphorothioate oligonucleotides having 2'-MOE wings and a deoxy gap

| ISIS # | Region | Target Seq ID NO | Start Site | SEQUENCE | % Inhib | SEQ ID NO |
|---|---|---|---|---|---|---|
| 196123 | 5' UTR | 439 | 3 | cgtctctggctgaaggctca | N.D. | 446 |
| 196124 | 5' UTR | 439 | 31 | ggctcagaatccactccttt | N.D. | 447 |
| 196125 | 5' UTR | 439 | 51 | gccaccagtgctaccgagca | N.D. | 448 |
| 196126 | Start Codon | 439 | 71 | cttctccatggtcactccct | N.D. | 449 |
| 196127 | Coding | 439 | 131 | catgcctgcctggtcagaca | N.D. | 450 |
| 196128 | Coding | 439 | 181 | gacacgtaggaattatctga | N.D. | 451 |
| 196129 | Coding | 439 | 201 | tctttaactgtgcgttgagg | N.D. | 452 |
| 196130 | Coding | 439 | 241 | gtgtagaagtagaggcacac | N.D. | 453 |
| 196131 | Coding | 439 | 261 | cacgagtcatggacagatca | N.D. | 454 |
| 196132 | coding | 439 | 341 | actatatcctatgtccttgg | N.D. | 455 |
| 196133 | Coding | 439 | 371 | gaatattatttcatctccac | N.D. | 456 |
| 196134 | Coding | 439 | 421 | tcccagcttgcacagaggtg | N.D. | 457 |
| 196135 | Coding | 439 | 441 | ctgcaatgcctgtgctggac | N.D. | 458 |
| 196136 | Coding | 439 | 461 | cttcccatctacccagagct | N.D. | 459 |
| 196137 | Coding | 439 | 491 | gcccttcttcagactcttcc | N.D. | 460 |
| 196138 | Coding | 439 | 526 | cccagaataatgcttgcctc | N.D. | 461 |
| 196139 | Coding | 439 | 601 | atgttcacatttccaatgtc | N.D. | 462 |
| 196140 | Coding | 439 | 621 | gtgaaagtgcatagtcccac | N.D. | 463 |
| 196141 | Coding | 439 | 661 | ctaaaggtcccaccagcata | N.D. | 464 |
| 196142 | 3' UTR | 439 | 771 | caagaagcaccttcaggatc | N.D. | 465 |
| 196143 | 3' UTR | 439 | 811 | ggtccacagccagaagtatg | N.D. | 466 |
| 196144 | 3' UTR | 439 | 841 | tagcaggcattcagtatatg | N.D. | 467 |
| 196145 | 3' UTR | 439 | 921 | caatgtagtccacaagatcc | N.D. | 468 |
| 196146 | 3' UTR | 439 | 1111 | accaatgtcctcttcccagt | N.D. | 469 |
| 196147 | 3' UTR | 439 | 1181 | gtgaatgtgggcaactacct | N.D. | 470 |

TABLE 5-continued

Inhibition of rabbit C-reactive protein mRNA levels by chimeric phosphorothioate oligonucleotides having 2'-MOE wings and a deoxy gap

| ISIS # | Region | Target Seq ID NO | Start Site | SEQUENCE | % Inhib | SEQ ID NO |
|---|---|---|---|---|---|---|
| 196148 | 3' UTR | 439 | 1201 | ttctgagagtgaatagccct | N.D. | 471 |
| 196149 | 3' UTR | 439 | 1221 | agtcctagctgatagcctaa | N.D. | 472 |
| 196150 | 3' UTR | 439 | 1251 | agaatgagcactgtgaactc | N.D. | 473 |
| 196151 | 3' UTR | 439 | 1371 | gcaagccttctctctaaggc | N.D. | 474 |
| 196152 | 3' UTR | 439 | 1411 | tgactatacccagatgccac | N.D. | 475 |
| 196153 | 3' UTR | 439 | 1561 | cctgactcttgtggcctgaa | N.D. | 476 |
| 196154 | 3' UTR | 439 | 1581 | taggacagcctgagtctcac | N.D. | 477 |
| 196155 | 3' UTR | 439 | 1601 | gagagatggactactctggt | N.D. | 478 |
| 196156 | 3' UTR | 439 | 1621 | gcaacatacagccatccatg | N.D. | 479 |
| 196157 | 3' UTR | 439 | 1641 | gtctgtaattgctcctgcta | N.D. | 480 |
| 196158 | 3' UTR | 439 | 1681 | acgtcttatcccagagtcc | N.D. | 481 |
| 196159 | 3' UTR | 439 | 1751 | tggtcaacaagatagctgca | N.D. | 482 |
| 196160 | 3' UTR | 439 | 1801 | agctctcagctcttccagct | N.D. | 483 |
| 196161 | 3' UTR | 439 | 1821 | cagattccaccactctgtca | N.D. | 484 |
| 196162 | 3' UTR | 439 | 1881 | caggaagtccaggtatagat | N.D. | 485 |
| 196163 | 3' UTR | 439 | 1901 | agctatattagtcacagacc | N.D. | 486 |
| 196164 | 3' UTR | 439 | 1951 | cctctaatgcaaccatcaga | N.D. | 487 |
| 196165 | 3' UTR | 439 | 2011 | atggtcagtctgagctcaca | N.D. | 488 |
| 196166 | 3' UTR | 439 | 2041 | tgccacggactctcccttgc | N.D. | 489 |
| 196167 | 3' UTR | 439 | 2071 | ccttgcaggagactccagat | N.D. | 490 |
| 196168 | 3' UTR | 439 | 2221 | tgaccatgacagcagatttg | N.D. | 491 |
| 196263 | 3' UTR | 439 | 2 | gtctctggctgaaggctcag | N.D. | 492 |
| 196264 | Coding | 439 | 525 | ccagaataatgcttgcctct | N.D. | 493 |
| 280264 | 5'UTR | 439 | 27 | cagaatccactcctttggag | 66 | 494 |
| 280265 | 5'UTR | 439 | 61 | gtcactccctgccaccagtg | 74 | 495 |
| 280266 | Start Codon | 439 | 81 | accacagcagcttctccatg | 25 | 496 |
| 280267 | Coding | 439 | 111 | tattagagaagctgaccaag | 27 | 497 |
| 280268 | Coding | 439 | 141 | ccttcttgtgcatgcctgcc | 74 | 498 |
| 280269 | Coding | 439 | 221 | agtgaaggctttgagtggct | 25 | 499 |
| 280270 | Coding | 439 | 311 | gaggatctcgttaaattgtc | 50 | 500 |
| 280271 | Coding | 439 | 364 | atttcatctccacccactga | 60 | 501 |
| 280272 | Coding | 439 | 411 | cacagaggtgagttggatcc | 59 | 502 |
| 280273 | Coding | 439 | 431 | tgtgctggactcccagcttg | 63 | 503 |
| 280274 | Coding | 439 | 451 | acccagagctctgcaa-gcc | 45 | 504 |
| 280275 | Coding | 439 | 495 | tgtagcccttcttcagactc | 46 | 505 |

TABLE 5-continued

Inhibition of rabbit C-reactive protein mRNA levels by chimeric phosphorothioate oligonucleotides having 2'-MOE wings and a deoxy gap

| ISIS # | Region | Target Seq ID NO | Start Site | SEQUENCE | % Inhib | SEQ ID NO |
|---|---|---|---|---|---|---|
| 280276 | Coding | 439 | 544 | aacgaatcctgatcctgccc | 70 | 506 |
| 280277 | Coding | 439 | 641 | gacggtattaatctcttctg | 70 | 507 |
| 280278 | 3'UTR | 439 | 773 | cccaagaagcaccttcagga | 92 | 508 |
| 280279 | 3'UTR | 439 | 851 | gctgtttatgtagcaggcat | 91 | 509 |
| 280280 | 3'UTR | 439 | 881 | ctctggtgttgaagaaggca | 86 | 510 |
| 280281 | 3'UTR | 439 | 1041 | ctaggcgtcaactttctcat | 100 | 511 |
| 280282 | 3'UTR | 439 | 1071 | tgacttaaaagtcacttctc | 46 | 512 |
| 280283 | 3'UTR | 439 | 1091 | taagtggtgaacctgtcttg | 72 | 513 |
| 280284 | 3'UTR | 439 | 1121 | tagacagaagaccaatgtcc | 79 | 514 |
| 280285 | 3'UTR | 439 | 1171 | gcaactaccttctactctct | 60 | 515 |
| 280286 | 3'UTR | 439 | 1211 | gatagcctaattctgagagt | 64 | 516 |
| 280287 | 3'UTR | 439 | 1291 | atcttctatttcagaagact | 81 | 517 |
| 280288 | 3'UTR | 439 | 1312 | agaatggcacagtattgctg | 72 | 518 |
| 280289 | 3'UTR | 439 | 1401 | cagatgccacttttgcccag | 65 | 519 |
| 280290 | 3'UTR | 439 | 1447 | atataagcaagcaaacaccc | 86 | 520 |
| 280291 | 3'UTR | 439 | 1571 | tgagtctcaccctgactctt | 56 | 521 |
| 280292 | 3'UTR | 439 | 1611 | gccatccatggagagatgga | 47 | 522 |
| 280293 | 3'UTR | 439 | 1631 | gctcctgctagcaacataca | 85 | 523 |
| 280294 | 3'UTR | 439 | 1671 | cccagagtccacactgaatc | 67 | 524 |
| 280295 | 3'UTR | 439 | 1725 | cccaggttcatgccttctaa | 92 | 525 |
| 280296 | 3'UTR | 439 | 1771 | cttctccatctccctccaca | 58 | 526 |
| 280297 | 3'UTR | 439 | 1861 | ttggttccatgcaaggctga | 39 | 527 |
| 280298 | 3'UTR | 439 | 1891 | gtcacagacccaggaagtcc | 81 | 528 |
| 280299 | 3'UTR | 439 | 1919 | ttcacccaggtaaccaagag | 77 | 529 |
| 280300 | 3'UTR | 439 | 1961 | gatagtcagacctctaatgc | 73 | 530 |
| 280301 | 3'UTR | 439 | 2031 | tctcccttgcaaggacagca | 57 | 531 |
| 280302 | 3'UTR | 439 | 2051 | gagattagagtgccacggac | 68 | 532 |
| 280303 | 3'UTR | 439 | 2081 | cagcaagaatccttgcagga | 85 | 533 |
| 280304 | 3'UTR | 439 | 2124 | cccacacgaatgactaattg | 75 | 534 |
| 280305 | 3'UTR | 439 | 2155 | gaataagagcattaagaccc | 62 | 535 |
| 280306 | 3'UTR | 439 | 2211 | agcagatttgagcttctcaa | 22 | 536 |
| 280307 | 3'UTR | 439 | 2271 | gaggagtctgtttctacaac | 10 | 537 |
| 280308 | 3'UTR | 439 | 2281 | ccttacctttgaggagtctg | 11 | 538 |
| 280309 | 3'UTR | 439 | 2285 | aagcccttacctttgaggag | 8 | 539 |

As shown in Table 5, SEQ ID NOs 494, 495, 498, 501, 502, 503, 506, 507, 508, 509, 510, 511, 513, 514, 515, 516, 517, 518, 519, 520, 521, 523, 524, 525, 526, 528, 529, 530, 531, 532, 533, 534 and 535 demonstrated at least 25% inhibition of rabbit C-reactive protein expression in this experiment and are therefore preferred.

Example 19

Antisense Inhibition of Human C-Reactive Protein Expression by Chimeric Phosphorothioate Oligonucleotides Having 2'-MOE Wings and a Deoxy Gap Dose Response Studies In a further embodiment of the present invention, five oligonucleotides were selected for additional dose-response studies. Cytokine-induced Hep3B cells were treated with 50, 100 and 150 nM of ISIS 133712, 133719, 133726, 140180 and 140177 and mRNA levels were measured 24 hours after oligonucleotide treatment as described in other examples herein. Untreated cells served as a control.

Results of these studies are shown in Table 6. Data are averages from two experiments and are expressed as percent inhibition of cytokine-induced control.

TABLE 6

Inhibition of cytokine-induced human C-reactive protein mRNA expression in Hep3B cells 24 hours after oligonucleotide treatment

| | % Inhibition Dose of oligonucleotide | | | |
|---|---|---|---|---|
| ISIS # | 50 nM | 100 nM | 150 nM | SEQ ID NO |
| 133712 | 60 | 84 | 77 | 22 |
| 133719 | 0 | 46 | 76 | 29 |
| 133726 | 75 | 85 | 92 | 36 |
| 140177 | 31 | 45 | 15 | 53 |
| 140180 | 26 | 59 | 91 | 56 |

As shown in Table 6, ISIS 133712, ISIS 133726 and ISIS 140180 were effective at reducing human C-reactive protein mRNA levels in a dose-dependent manner and are therefore preferred compounds of the present invention.

Example 20

Antisense Inhibition of Rat C-Reactive Protein Expression by Chimeric Phosphorothioate Oligonucleotides Having 2'-MOE Wings and a Deoxy Gap Dose Response Studies In a further embodiment of the present invention, three oligonucleotides were selected for additional dose-response studies. Rat primary hepatocytes were treated with 50, 150 and 300 nM of ISIS 197181, 197178, 197183 and 197190. Target mRNA levels were measured at 24 hours post oligonucleotide treatment as described in other examples herein. Untreated cells served as a control.

Results of these studies are shown in Table 7. Data are averages from three experiments and are expressed as percent inhibition of control.

TABLE 7

Inhibition of rat C-reactive protein mRNA expression in primary hepatocytes: dose response

| | | % Inhibition Dose, nM | | |
|---|---|---|---|---|
| ISIS # | SEQ ID NO | 50 | 150 | 300 |
| 197181 | 278 | 38 | 37 | 37 |
| 197178 | 275 | 38 | 56 | 65 |
| 197183 | 280 | 9 | 73 | 84 |
| 197190 | 287 | 55 | 71 | 85 |

As shown in Table 7, ISIS 197181, ISIS 197178, ISIS 197183 and ISIS 197190 were effective at reducing rat C-reactive protein mRNA levels in a dose-dependent manner and are therefore preferred compounds of the present invention.

Example 21

Antisense Inhibition of Rat C-Reactive Protein Expression by Chimeric Phosphorothioate Oligonucleotides Having 2'-MOE Wings and a Deoxy Gap In Vivo Dose Response Studies In a further embodiment of the present invention, three oligonucleotides were selected for additional in vivo dose response studies. Three-month old male Sprague-Dawley rats received subcutaneous injections of saline or 1, 10 or 25 mg/kg of ISIS 197178 (SEQ ID NO:275), ISIS 197183 (SEQ ID NO:280) and ISIS 197190 (SEQ ID NO:287) twice weekly for 2 weeks. At the end of the treatment period, animals were sacrificed and liver target mRNA levels were measured by real-time PCR as described in other examples herein. Saline treated animals served as a control. Rat liver C-reactive protein mRNA levels were reduced by 5% following a 1 mg/kg dose of 197178 and by 18% following a 10 mg/kg dose of ISIS 197190.

Example 22

Antisense Inhibition of Rabbit C-Reactive Protein Expression by Chimeric Phosphorothioate Oligonucleotides Having 2'-MOE Wings and a Deoxy Gap Dose Response Studies In a further embodiment of the present invention, four oligonucleotides were selected for additional dose-response studies. Rabbit primary hepatocytes were treated with 10, 50 150 and 300 nM of ISIS 280279, 280290, 280298 and 282303. mRNA levels were measured 24 hours after oligonucleotide treatment as described in other examples herein. Untreated cells served as a control.

Results of these studies are shown in Table 8. Data are averages from two experiments and are expressed as percent inhibition of control.

TABLE 8

Inhibition of rabbit C-reactive protein mRNA expression in rabbit primary hepatocytes: dose response % Inhibition

| ISIS # | SEQ ID NO | Dose of oligonucleotide | | | |
|---|---|---|---|---|---|
| | | 10 nM | 50 nM | 150 nM | 300 nM |
| 280279 | 509 | 55 | 53 | 62 | 35 |
| 280290 | 520 | 49 | 77 | 84 | 81 |
| 280298 | 528 | 55 | 53 | 62 | 36 |
| 282303 | 533 | 40 | 76 | 80 | 87 |

As shown in Table 8, ISIS 280303 and ISIS 280290 were effective at reducing C-reactive protein mRNA levels in a dose-dependent manner and are therefore preferred compounds of the present invention.

Example 23

Antisense Inhibition of C-Reactive Protein Expression (ISIS 133726) in Liver Tissue of the Cynomolgus Monkey In a further embodiment, male Cynomolgus monkeys were treated with ISIS 133726 (SEQ ID NO:36) and levels of C-reactive protein mRNA were measured in liver tissue.

Male Cynomolgus monkeys were divided into two treatment groups, control animals (n=4; saline treatment only) and treated animals (n=8; treated with ISIS 133726). Animals in the treatment group were dosed subcutaneously twice a week for 4 weeks with 10 mg/kg and 20 mg/kg of ISIS 133726, respectively. Animals in the control group were treated with saline only. Three days later, all animals were sacrificed and livers were taken for analysis of C-reactive protein mRNA. Levels of mRNA were normalized to those of the saline treated animals. In animals treated with 10 mg/kg and 20 mg/kg ISIS 133726, C-reactive protein mRNA levels within liver were reduced by 42% and 69%, respectively.

Levels of the liver enzymes ALT and AST were measured weekly and showed no change, indicating no ongoing toxic effects of the oligonucleotide treatment.

The results of this study demonstrate a significant reduction in liver C-reactive protein mRNA upon treatment with ISIS 133726.

Example 24

Modulation of Mouse C-Reactive Protein Expression by Chimeric Phosphorothioate Oligonucleotides Having 2'-MOE Wings and a Deoxy Gap In accordance with the present invention, a series of antisense compounds was designed to target different regions of the mouse C-reactive protein RNA, using published sequences (GENBANK® accession number NM_007768.1, incorporated herein as SEQ ID NO:540). The compounds are shown in Table 9. "Target site" indicates the first (5'-most) nucleotide number on the particular target nucleic acid to which the compound binds. All compounds in Table 9 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE)nucleotides. The internucleoside (backbone) linkages are phosphorothioate (P=S) throughout the oligonucleotide. All cytidine residues are 5-methylcytidines.

The compounds were analyzed for their effect on mouse C-reactive protein mRNA levels by quantitative real-time PCR as described in other examples herein. Probes and primers to mouse C-reactive protein were designed to hybridize to a mouse C-reactive protein sequence, using published sequence information (GENBANK® accession number NM_007768.1, incorporated herein as SEQ ID NO:540). For mouse C-reactive protein the PCR primers were:

forward primer: TGGATTGATGGGAAACCCAA (SEQ ID NO:541)

reverse primer: GCATCTGGCCCCACAGTG (SEQ ID NO:542) and the PCR probe was: FAM-TGCG-GAAAAGTCTGCACAAGGGC-TAMRA (SEQ ID NO: 543) where FAM is the fluorescent reporter dye and TAMRA is the quencher dye. For mouse GAPDH the PCR primers were:

forward primer: GGCAAATTCAACGGCACAGT (SEQ ID NO:544)

reverse primer: GGGTCTCGCTCCTGGAAGAT (SEQ ID NO:545) and the PCR probe was: 5' JOE-AAGGC-CGAGAATGGGAAGCTTGTCATC-TAMRA 3' (SEQ ID NO:546) where JOE is the fluorescent reporter dye and TAMRA is the quencher dye. Data, shown in Table 9, are from an experiment in which primary mouse hepatocytes were treated with 150 nM the antisense oligonucleotides of the present invention. The data are presented as percent expression relative to control, untreated cells. If present, "N.D." indicates "no data".

TABLE 9

Modulation of mouse C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % CONTROL | SEQ ID NO |
|---|---|---|---|---|---|---|
| 133685 | 5' UTR | 540 | 21 | TTTGTCTGAAAGATCAAGGA | 83 | 547 |
| 133686 | 5' UTR | 540 | 31 | AGGACAGTGTTTTGTCTGAA | 55 | 548 |
| 133687 | start codon | 540 | 71 | CTTCTCCATGGCTATGGATG | 68 | 549 |
| 133688 | start codon | 540 | 81 | ACCAGAGTAGCTTCTCCATG | 131 | 550 |

TABLE 9-continued

Modulation of mouse C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % CONTROL | SEQ ID NO |
|---|---|---|---|---|---|---|
| 133689 | coding | 540 | 221 | AGTAAAGGTGTTCAGTGGCT | 84 | 551 |
| 133690 | coding | 540 | 301 | TTAGAGTTCTTCTTGGTAGC | 36 | 552 |
| 133691 | coding | 540 | 371 | GAATCGTACTTCAGCACCAC | 139 | 553 |
| 133692 | coding | 540 | 411 | CACAGATGTGTGTTGGAGCC | 128 | 554 |
| 133693 | coding | 540 | 441 | CTACAATCCCCGTAGCAGAC | 122 | 555 |
| 133694 | coding | 540 | 531 | CCTGCCCCAAGATGATGCTT | 238 | 556 |
| 133695 | coding | 540 | 661 | CTGAGTGTCCCACCAACATA | 183 | 557 |
| 133696 | coding | 540 | 711 | CATCACCCTGTGCTTTATAG | 175 | 558 |
| 133697 | stop codon | 540 | 741 | GTCAGGACCACAGCTGCGGC | 48 | 559 |
| 133698 | stop codon | 540 | 761 | TTCAGGGTTCACAACAGTAG | 67 | 560 |
| 133699 | 3' UTR | 540 | 781 | AATGTAATCCCAGGAGGTGC | 44 | 561 |
| 133700 | 3' UTR | 540 | 891 | GTGCTCTAGTGCTGAGGACC | 102 | 562 |
| 133701 | 3' UTR | 540 | 1091 | CTCCTTTCTGTGCATCTATT | 70 | 563 |
| 133702 | 3' UTR | 540 | 1261 | AGATGATAGGTATTATGCAT | 120 | 564 |
| 133703 | 3' UTR | 540 | 1361 | CCAGTGTCCAGTCTTCAACA | 52 | 565 |
| 133704 | 3' UTR | 540 | 1381 | GGGCCCTCCTGATAGATTAT | 87 | 566 |
| 133705 | 3' UTR | 540 | 1425 | GTAATCAGTGGCTGCTGAGA | 46 | 567 |
| 133706 | 3' UTR | 540 | 1451 | ACAGAACCCTATATGAAGAG | 94 | 568 |
| 133707 | 3' UTR | 540 | 1508 | AGACCTGCATAATGACACCA | 34 | 569 |
| 133708 | 3' UTR | 540 | 1551 | GCACAGTGTAGTCAGTGCTC | 50 | 570 |
| 147859 | 5' UTR | 540 | 1 | CAAGGAGTCCTGGAACGCCT | 414 | 571 |
| 147860 | 5' UTR | 540 | 41 | CTGGACTAAGAGGACAGTGT | 81 | 572 |
| 147861 | coding | 540 | 102 | AGCTGATCATGATCAGAAGG | 435 | 573 |
| 147862 | coding | 540 | 191 | TGCTTCCAGAGACACATAGG | 262 | 574 |
| 147863 | coding | 540 | 241 | GTGTAGAAATGGAGACACAC | 212 | 575 |
| 147864 | coding | 540 | 281 | ATAAGAGAAGACACTGAAGC | 129 | 576 |
| 147865 | coding | 540 | 501 | CCACAGTGTAGCCCTTGTGC | N.D. | 577 |
| 147866 | coding | 540 | 521 | GATGATGCTTGCATCTGGCC | 148 | 578 |
| 147867 | coding | 540 | 544 | TACGAGTCCTGCTCCTGCCC | 106 | 579 |
| 147868 | coding | 540 | 571 | GACTGCTTTGCATCAAAGTC | 26 | 580 |
| 147869 | coding | 540 | 701 | TGCTTTATAGTTCAGTGCCC | 72 | 581 |
| 147870 | 3' UTR | 540 | 801 | TAACCCGAGACAAGGGAGAG | 95 | 582 |
| 147871 | 3' UTR | 540 | 841 | CAGAACAGACCTACAACATC | 89 | 583 |
| 147872 | 3' UTR | 540 | 861 | GAAGTGAAAGGCCATATTCA | 91 | 584 |

TABLE 9-continued

Modulation of mouse C-reactive protein mRNA levels by chimeric phosphorothioate oligonucleotides having 2'-MOE wings and a deoxy gap

| ISIS # | REGION | TARGET SEQ ID NO | TARGET SITE | SEQUENCE | % CONTROL | SEQ ID NO |
|---|---|---|---|---|---|---|
| 147873 | 3' UTR | 540 | 931 | TAGTGGGATGCTTATGCTGG | 275 | 585 |
| 147874 | 3' UTR | 540 | 1141 | AATACAGCACTCAAGATGAC | 212 | 586 |
| 147875 | 3' UTR | 540 | 1181 | ATAGGAAAGGATCTGAAGAG | 93 | 587 |
| 147876 | 3' UTR | 540 | 1211 | CATCATGAATTTGAGAGAGA | 138 | 588 |
| 147877 | 3' UTR | 540 | 1281 | AGGTAGATAGATTGATTGAT | 314 | 589 |
| 147878 | 3' UTR | 540 | 1301 | CTGATGAATAGATGATAGAT | 228 | 590 |
| 147879 | 3' UTR | 540 | 1321 | GTAATCAGTAAGATGGATGA | 381 | 591 |
| 147880 | 3' UTR | 540 | 1378 | CCCTCCTGATAGATTATCCA | 38 | 592 |
| 147881 | 3' UTR | 540 | 1501 | CATAATGACACCAATTGACA | 101 | 593 |
| 147882 | 3' UTR | 540 | 1521 | GGTTGCCCAAACAAGACCTG | 144 | 594 |
| 147883 | 3' UTR | 540 | 1541 | GTCAGTGCTCCATCACTCTA | 44 | 595 |
| 147884 | 3' UTR | 540 | 1561 | CTGATTCTGAGCACAGTGTA | 233 | 596 |

Example 25

Antisense Inhibition of Mouse C-Reactive Protein Expression by Chimeric Phosphorothioate Oligonucleotides Having 2'-MOE Wings and a Deoxy Gap Dose Response Studies In a further embodiment of the present invention, seven oligonucleotides were selected for additional dose-response studies. Primary mouse hepatocytes were treated with 10, 50 150 and 300 nM of ISIS 133688, 133697, 133702, 133708, 147880, 147868, 147883. mRNA levels were measured 24 hours after oligonucleotide treatment as described in other examples herein. Untreated cells served as a control.

Results of these studies are shown in Table 10. Data are averages from three experiments and are expressed as percent inhibition of control.

TABLE 10

Inhibition of mouse C-reactive protein mRNA expression in mouse primary hepatocytes: dose response

| ISIS # | SEQ ID NO | % Inhibition Dose of oligonucleotide | | | |
|---|---|---|---|---|---|
| | | 10 nM | 50 nM | 150 nM | 300 nM |
| 133688 | 550 | 59 | 75 | 75 | 67 |
| 133697 | 559 | 63 | 63 | 76 | 76 |
| 133702 | 564 | 43 | 35 | 45 | 52 |
| 133708 | 570 | 72 | 74 | 72 | 72 |
| 147868 | 580 | 59 | 59 | 76 | 80 |
| 147880 | 592 | 61 | 69 | 82 | 77 |
| 147883 | 595 | 90 | 82 | 91 | 70 |

As demonstrated in Table 10, ISIS 113697 and 147868 inhibited C-reactive protein expression in a dose-dependent manner.

Example 26

Antisense Inhibition of Rabbit C-Reactive Protein In Vivo

In a further embodiment of the present invention, ISIS 280303 (SEQ ID NO:533) was tested for its effects on C-reactive proteins in rabbits. Male New Zealand white rabbits were fed a normal diet and received subcutaneous injections of 20 mg/kg ISIS 280303 twice per week for a period of three weeks. Saline-injected animals served as a control. Oligonucleotide- and saline-injected groups included 4 animals each. At the end of the treatment period, the animals were sacrificed and the liver was isolated for RNA extraction. C-reactive protein mRNA levels in liver were measured by real-time PCR as described by other examples herein. Relative to the saline control, ISIS 280303 inhibited C-reactive protein mRNA expression by 52%.

Example 27

Rabbit Models for Study of Atherosclerotic Plaque Formation

The Watanabe heritable hyperlipidemic (WHHL) strain of rabbit is used as a model for atherosclerotic plaque formation. New Zealand white rabbits on a high-fat diet are also used as a model of atherosclerotic plaque formation. Treatment of WHHL or high fat fed New Zealand white rabbits with C-reactive protein antisense compounds is used to test their potential as therapeutic or prophylactic treatments for atherosclerotic plaque disease. Rabbits are injected with 5, 10, 29 or 50 mg/kg of antisense oligonucleotides targeted to C-reactive protein. Animals treated with saline alone or a control oligonucleotide serve as controls. Throughout the treatment, serum samples are collected and evaluated for serum lipids, including cholesterol, LDL-cholesterol, VLDL-cholesterol, HDL-cholesterol and triglycerides, by routine clinical analysis. Liver tissue triglyceride content is measured using a Triglyceride GPO Assay (Sigma-Aldrich, St. Louis, Mo.). Liver, kidney, heart, aorta and other tissues are procured and processed for histological analysis using routine procedures. Liver and kidney tissues are examined for evidence of basophilic granules and inflammatory infiltrates. The aorta is stained using routine procedures, with a dye such as Sudan IV, to visualize atherosclerosis. Aorta tissue is also embedded in paraffin and sectioned, using routine histological procedures, and the sections are evaluated for the presence of intimal lesions.

Example 28

A Mouse Model for Atherosclerotic Plaque Formation

Human C-Reactive Protein Transgenic Mice Lacking the LDL Receptor Gene

The LDL receptor is responsible for clearing C-reactive protein-containing LDL particles. Without the LDL receptor, animals cannot effectively clear C-reactive protein-containing LDL particles from the plasma, thus the serum levels of C-reactive protein and LDL cholesterol are markedly elevated. Mice expressing the human C-reactive protein transgene (TgN-hApoB+/+) and mice deficient for the LDL receptor (LDLr-/-) are both used as animal models of atherosclerotic plaque development. When the LDL receptor deficiency genotype is combined with a human C-reactive protein transgenic genotype (TgN-hApoB+/+; LDLr-/-), atherosclerotic plaques develop rapidly. In accordance with the present invention, mice of this genetic background are used to investigate the ability of compounds to prevent atherosclerosis and plaque formation.

Male TgN-hApoB+/+; LDLr-/- mice are treated twice weekly with 10 or 20 mg/kg of C-reactive protein antisense oligonucleotides for 12 weeks. Control groups are treated with saline or control oligonucleotide. Serum total cholesterol, HDL-cholesterol, LDL-cholesterol and triglycerides are measured at 2, 4, 6, 8 and 12 weeks by routine clinical analysis using an Olympus Clinical Analyzer (Olympus America Inc., Melville, N.Y.). Mouse apolipoprotein mRNA in liver is measured at 12 weeks.

Additionally, a four month study is performed in TgN-hApoB+/+; LDLr-/- mice, with treatment conditions used in the 12 week study. Mice are treated for 4 months with antisense oligonucleotides targeted to C-reactive protein to evaluate the ability of such compounds to prevent atherosclerotic plaque formation. Serum total cholesterol, HDL-cholesterol, LDL-cholesterol and triglycerides are measured at 2, 4, 6, 8, 12 and 16 weeks by routine clinical analysis using an Olympus Clinical Analyzer (Olympus America Inc., Melville, N.Y.). Mouse C-reactive protein mRNA in liver at 16 weeks is measured by real-time PCR. At the end of the 4-month treatment period, additional treated mice are anesthetized and perfused with 10% formalin. The perfused arterial tree is isolated and examined for the presence of atherosclerotic plaques. Sections of the arterial tree are embedded in paraffin and prepared for histological analysis using routine methods.

Example 29

A Mouse Model for Atherosclerotic Plaque Formation

B6.129P-Apoe$^{tm1Unc}$ Knockout Mice

B6.129P-ApoE$^{tm1Unc}$ knockout mice (herein referred to as ApoE knockout mice) obtained from The Jackson Laboratory (Bar Harbor, Me.), are homozygous for the Apoe$^{tm1Unc}$ mutation and show a marked increase in total plasma cholesterol levels that are unaffected by age or sex. These animals present with fatty streaks in the proximal aorta at 3 months of age. These lesions increase with age and progress to lesions with less lipid but more elongated cells, typical of a more advanced stage of pre-atherosclerotic lesion.

The mutation in these mice resides in the apolipoprotein E (ApoE) gene. The primary role of the ApoE protein is to transport cholesterol and triglycerides throughout the body. It stabilizes lipoprotein structure, binds to the low density lipoprotein receptor (LDLR) and related proteins, and is present in a subclass of HDLs, providing them the ability to bind to LDLR. ApoE is expressed most abundantly in the liver and brain. Female B6.129P-Apoetm1Unc knockout mice (ApoE knockout mice) were used in the following studies to evaluate C-reactive protein antisense oligonucleotides as potential compounds for preventing atherosclerotic plaque formation.

Female ApoE knockout mice range in age from 5 to 7 weeks and are placed on a normal diet for 2 weeks before study initiation. ApoE knockout mice are then fed ad libitum a 60% fat diet, with 0.15% added cholesterol to induce dyslipidemia and obesity. Control animals are maintained on a high-fat diet with no added cholesterol. After overnight fasting, mice from each group are dosed intraperitoneally every three days with 5, 25 or 50 mg/kg of antisense oligonucleotide targeted to C-reactive protein, for a period of six weeks. Control groups consist of animals injected with a control oligonucleotide and animals injected with saline.

During and at the end of the treatment period, glucose levels, cholesterol (total cholesterol, HDL-cholesterol and LDL-cholesterol), triglyceride and liver enzyme levels are measured by routine clinical analysis using an Olympus Clinical Analyzer (Olympus America Inc., Melville, N.Y.). At study termination and forty-eight hours after the final injections, animals were sacrificed and evaluated for target mRNA levels in liver by real-time PCR. At the end of the treatment period, additional treated mice are anesthetized and perfused with 10% formalin. The perfused arterial tree is isolated and examined for the presence of atherosclerotic plaques. Sec-

Example 30

Antisense Inhibition of Human C-Reactive Protein mRNA Expression by Chimeric Phosphorothioate Oligonucleotides Having 2'-MOE Wings and a Deoxy Gap

Dose Response Study

In a further embodiment, four oligonucleotides were selected for an additional dose-response study. Cytokine-induced Hep3B cells, cultured as described herein, were treated with 25, 50, 75 and 150 nM of ISIS 329956 (SEQ ID NO: 149), ISIS 330012 (SEQ ID NO:205), ISIS 330031 (SEQ ID NO: 224) and ISIS 133726 (SEQ ID NO:36). 24 hours following oligonucleotide treatment, human C-reactive protein mRNA levels were quantitated using real-time PCR as described herein. ISIS 113529 (CTCTTACTGTGCTGTGGACA; incorporated herein as SEQ ID NO:597) does not target C-reactive protein and served as a control. Cells were treated with 150 and 300 nM of ISIS 113529. ISIS 113529 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Levels of C-reactive protein mRNA expression were also measured in cytokine-induced cells that were not treated with oligonucleotide (induced) and cells that receive neither cytokine nor oligonucleotide treatment (basal).

The results of this dose-response study are shown in Table 11. Data are averages from three experiments. Results were normalized to expression of C-reactive protein mRNA from cytokine-induced cells. Basal C-reactive protein mRNA was 11% of the cytokine-induced expression. Cells treated with 150 and 300 nM of ISIS 113529 expressed C-reactive protein mRNA at 76 and 84% of the cytokine-induced levels, respectively.

TABLE 11

Inhibition of cytokine-induced human C-reactive protein mRNA expression in Hep3B cells 24 hours after oligonucleotide treatment

| | % C-reactive protein mRNA expression relative to cytokine-induced cells Dose of oligonucleotide | | | |
|---|---|---|---|---|
| ISIS # | 25 nM | 50 nM | 75 nM | 150 nM |
| 329956 | 45 | 41 | 21 | 19 |
| 330012 | 48 | 33 | 22 | 12 |
| 330031 | 53 | 29 | 21 | 26 |
| 133726 | 94 | 51 | 33 | 23 |

These data reveal that ISIS 329956, ISIS 330012, ISIS 330031 and ISIS 133726 inhibited human C-reactive protein expression in cytokine-induced Hep3B cells, in a dose-dependent manner.

Example 31

Antisense Inhibition of Human C-Reactive Protein Secretion by Hep3B Cells

Dose Response Study

In a further embodiment of the present invention, four oligonucleotides were selected for an additional dose-response study to measure the effect of antisense oligonucleotide treatment on the secretion of C-reactive protein from cytokine-induced Hep3B cells. Cytokine-induced Hep3B cells, cultured as described herein, were treated with 150 and 300 nM of ISIS 329956 (SEQ ID NO:149), ISIS 330012 (SEQ ID NO:205), ISIS 330031 (SEQ ID NO:224) and ISIS 133726 (SEQ ID NO:36). Cells were treated with the control oligonucleotide ISIS 113529 (SEQ ID NO:597) at 150 and 300 nM. 24 hours following oligonucleotide treatment human C-reactive protein secreted from cytokine-induced Hep3B cells into the culture media was measured by ELISA using a commercially available kit (ALerCHEK Inc., Portland, Me.). C-reactive protein secretion was also measured in cytokine-induced cells that were not treated with oligonucleotide (induced) and cells that received neither cytokine nor oligonucleotide treatment (basal).

The results of this dose-response study are shown in Table 12. Data are averages from three experiments. Results were normalized to C-reactive protein levels secreted from cytokine-induced cells. Basal C-reactive protein level in the culture media was 8% of the cytokine-induced level.

TABLE 12

Inhibition of cytokine-induced human C-reactive protein secretion from Hep3B cells 24 hours after oligonucleotide treatment

| | % C-reactive protein secretion relative to cytokine-induced cells Dose of oligonucleotide | |
|---|---|---|
| | 150 nM | 300 nM |
| 329956 | 71 | 65 |
| 330012 | 69 | 47 |
| 330031 | 78 | 107 |
| 133726 | 76 | 55 |
| 113529 | 127 | 113 |

These data reveal that ISIS 329956, ISIS 330012 and ISIS 133726 inhibited secretion of C-reactive protein from cytokine-induced Hep3B cells, in a dose-dependent manner. ISIS 330031 inhibited C-reactive protein secretion at the lower dose of oligonucleotide. The control oligonucleotide ISIS 113529 did not inhibit C-reactive protein secretion.

Example 32

Antisense Oligonucleotides Targeted to C-Reactive Protein Having Variable 2'-Deoxy Gaps and Variable 2'-MOE Wings In a further embodiment, antisense oligonucleotides targeted to C-reactive protein were designed using the nucleotide sequences of SEQ ID NOs 36 and 205 and employing various gap and wing segment lengths. The compounds are shown in Table 13. "Target site" indicates the first (5'-most) nucleotide number on the particular target sequence to which the compound binds. All compounds in Table 13 are chimeric oligonucleotides ("gapmers") ranging from 16 to 20 nucleotides in length. The "gap" region consists of 2'-deoxynucleotides, which is flanked on one or both sides (5' and 3' directions) by "wings" composed of 2'-O-methoxyethyl (2'-MOE) nucleotides. The length of the 2'-deoxy gap varies from 10 to 18 nucleotides and the length of the 2'-MOE wings varies from 1 to 5 nucleotides. The exact structure of each oligonucleotide is designated in Table 13 as the "configuration". A designation of 3~14~3, for instance, indicates that the first (5'-most) 3 nucleotides and the last (3'-most) 3 nucleotides are 2'-MOE nucleotides and the 14 nucleotides in the gap are 2'-deoxynucleotides. The internucleoside (backbone) linkages are phosphorothioate (P=S) throughout the oligonucleotide. All cytidine residues are 5-methylcytidines.

otides, with phosphorothioate internucleoside linkages throughout the oligonucleotide. All cytosines are 5-methylcytosines.

A subset of these antisense oligonucleotides was selected for testing in cytokine-induced Hep3B cells. All oligonucleotides tested share the same nucleotide sequence represented herein as SEQ ID NO:205, and vary with respect to modifications of the sugar moieties. Cells were cultured and induced as described herein, and subsequently treated with 50, 100 and 200 nM of ISIS 353470, ISIS 353512, ISIS 353472, ISIS 353473 and ISIS 330012 for a period of 24 hours. Cytokine-induced cells served as the control to which data were normalized. C-reactive protein mRNA was measured by real-time PCR as described herein. Data, shown in Table 14, represent the average of 3 experiments and are normalized to data from cells receiving cytokine treatment only. For the gapmers, the configuration of each oligonucleotide is indicated in the same manner as described for Table 13. The

TABLE 13

Antisense oligonucleotides targeted to C-reactive protein having varying 2'-deoxy gaps and varying 2'-MOE wings

| ISIS # | REGION | TARGET SEQ ID NO | TARGET SITE | SEQUENCE | Configuration | SEQ ID NO |
|---|---|---|---|---|---|---|
| 353490 | 3' UTR | 4 | 1671 | GCACTCTGGACCCAAACCAG | 4~12~4 | 36 |
| 353491 | 3' UTR | 4 | 1671 | GCACTCTGGACCCAAACCAG | 3~14~3 | 36 |
| 353492 | 3' UTR | 4 | 1671 | GCACTCTGGACCCAAACCAG | 2~16~2 | 36 |
| 353470 | 3' UTR | 4 | 1719 | TCCCATTTCAGGAGACCTGG | 4~12~4 | 205 |
| 353471 | 3' UTR | 4 | 1719 | TCCCATTTCAGGAGACCTGG | 3~16~1 | 205 |
| 353472 | 3' UTR | 4 | 1719 | TCCCATTTCAGGAGACCTGG | 2~16~2 | 205 |
| 353512 | 3' UTR | 4 | 1719 | TCCCATTTCAGGAGACCTGG | 3~14~3 | 205 |
| 353480 | 3' UTR | 4 | 1719 | TCCCATTTCAGGAGACCTG | 5~10~4 | 598 |
| 353486 | 3' UTR | 4 | 1719 | CCCATTTCAGGAGACCTGG | 4~10~4 | 599 |
| 353499 | 3' UTR | 4 | 1672 | GCACTCTGGACCCAAACCA | 5~10~4 | 600 |
| 353502 | 3' UTR | 4 | 1671 | CACTCTGGACCCAAACCAG | 4~10~5 | 601 |
| 353481 | 3' UTR | 4 | 1720 | TCCCATTTCAGGAGACCT | 5~10~3 | 602 |
| 353483 | 3' UTR | 4 | 1721 | CCCATTTCAGGAGACCTG | 4~10~4 | 603 |
| 353487 | 3' UTR | 4 | 1719 | CCATTTCAGGAGACCTGG | 3~10~5 | 604 |
| 353500 | 3' UTR | 4 | 1672 | GCACTCTGGACCCAAACC | 5~10~3 | 605 |
| 353503 | 3' UTR | 4 | 1671 | ACTCTGGACCCAAACCAG | 3~10~5 | 606 |
| 353505 | 3' UTR | 4 | 1673 | CACTCTGGACCCAAACCA | 4~10~4 | 607 |
| 353484 | 3' UTR | 4 | 1722 | CCATTTCAGGAGACCT | 3~10~3 | 608 |
| 353506 | 3' UTR | 4 | 1674 | ACTCTGGACCCAAACC | 3~10~3 | 609 |

Additional oligonucleotides were designed, using the nucleotide sequence of SEQ ID Nos 36 and 205 and incorporating uniformly modified nucleotides. ISIS 353489 and ISIS 353473 (sequences incorporated herein as SEQ ID Nos 36 and 205, respectively) hybridize to target sites 1671 and 1719 of SEQ ID NO:4, respectively. These two compounds are uniformly comprised of 2'-O-methoxyethyl (2'-MOE) nucleoligonucleotide uniformly comprised of 2'-MOE nucleotides is indicated by "uniform 2'-MOE".

TABLE 14

Comparison of antisense inhibition by oligonucleotides targeted to C-reactive protein having varying 2'-deoxy gaps and varying 2'-MOE wings

| ISIS # | Configuration | % mRNA expression relative to cytokine-induced control cells Dose of oligonucleotide | | |
|---|---|---|---|---|
| | | 50 nM | 100 nM | 200 nM |
| 353470 | 4~12~4 | 37 | 28 | 15 |
| 353512 | 3~14~3 | 20 | 16 | 28 |
| 353472 | 2~16~2 | 74 | 42 | 9 |
| 353473 | Uniform 2'-MOE | 117 | 89 | 80 |
| 330012 | 5~10~5 | 55 | 39 | 29 |

Additional oligonucleotides were designed, using the nucleotide sequence of SEQ ID Nos 36 and 205 and employing differing internucleoside linkages in the compound. ISIS 353514 and ISIS 353515 (sequences incorporated herein as SEQ ID Nos 36 and 205, respectively) hybridize to target sites 1671 and 1719 of SEQ ID NO:4, respectively. These two compounds are chimeric oligonucleotides, having a 14 nucleotide gap segment composed of 2'-deoxynucleotides, which is flanked on both sides (5' and 3') by 3 nucleotide wing segments composed of 2'-O-methoxyethyl (2'-MOE) nucleotides. The internucleoside linkages between nucleotides 2 and 3 and between nucleotides 18 and 19 are phosphodiester. All other nucleoside linkages in the compounds are phosphorothioate. All cytosines are 5-methylcytosines.

Additional olignucleotides were designed using the publicly available sequence of human C-reactive protein (incorporated herein as SEQ ID NO:4). The compounds are shown in Table 15. "Target site" indicates the first (5'-most) nucleotide number on the particular target sequence to which the compound binds. These compounds are hemimers, or "open end" type compounds, 15 nucleotides in length, wherein the "gap" segment is located at either the 3' or the 5' terminus of the oligomeric compound and consists of 2'-deoxynucleotides. The remaining segment is composed of 2'-O-methoxyethyl (2'-MOE) nucleotides. The exact structure of each oligonucleotide is designated in Table 15 as the "configuration". A designation of 5-10, for instance, indicates that a 5 nucleotide segment of a first chemical modification is at the 5' terminus and a 10 nucleotide segment of a second chemical modification is at the 3' terminus. A designation of 2'-MOE-2'-deoxy indicates that the 5' terminus is comprised of 2'-MOE nucleotides, and the 3' terminus is comprised of 2'-deoxynucleotides; 2'-MOE nucleotides are further indicated in bold type. Where present, "O" indicates that the internucleoside (backbone) linkages are phosphodiester. All other internucleoside linkages are phosphorothioate (P=S). All cytidine residues are 5-methylcytidines.

Example 33

Antisense Inhibition of Human C-Reactive Protein Expression by Chimeric Phosphorothioate Oligonucleotides Having 2'-MOE Wings and a Deoxy Gap

Dose Response Studies

In a further embodiment, oligonucleotides targeted to human C-reactive protein were selected for additional dose-response studies. Following antisense oligonucleotide treatment, C-reactive protein mRNA and secreted protein were measured in primary human hepatocytes, cultured as described herein and cytokine-induced as described herein for Hep3B cells.

Primary human hepatocytes were treated with 12.5, 25, 50, 100 and 200 nM of ISIS 330012 (SEQ ID NO:205) and ISIS 133726 (SEQ ID NO:36). Cytokine-induced cells that did not receive oligonucleotide treatment served as controls to which all data were normalized. ISIS 13650 (TCCCGCCTGTGA-CATGCATT, SEQ ID NO:614) and ISIS 113529 (SEQ ID NO:597), neither of which target C-reactive protein, served as control oligonucleotides. Cells were treated with 100 and 200 nM of ISIS 113529 and ISIS 13650. ISIS 13650 is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

C-reactive protein mRNA levels were measured after 24 hours of oligonucleotide treatment by real-time PCR as described in other examples herein. Results of these studies are shown in Table 16. Data are averages from three experiments and are expressed as percent mRNA expression relative to data from cytokine-induced cells. Where present, "N.D." indicates not determined.

TABLE 16

Inhibition of human C-reactive protein mRNA expression in human primary hepatocytes: 24 hr dose response % mRNA expression relative to

TABLE 15

Chimeric hemimers targeted to C-reactive protein

| ISIS # | REGION | TARGET SEQ ID NO | TARGET SITE | SEQUENCE | Configuration | SEQ ID NO |
|---|---|---|---|---|---|---|
| 353698 | 3' UTR | 4 | 1720 | TCCCA$_O$TTTCAGGAGA | 5~10 2'-MOE~2'-deoxy | 610 |
| 353699 | 3' UTR | 4 | 1719 | TTTGAGGAGA$_O$CCTGG | 10~5 2'-deoxy~2'-MOE | 611 |
| 353501 | 3' UTR | 4 | 1672 | GCACTCTGGACCCAA | 5~10 2'-MOE~2'-deoxy | 612 |
| 353504 | 3' UTR | 4 | 1671 | CTGGACCCAAACCAG | 1~14 2'-deoxy~2'-MOE | 613 |

| | | cytokine-induced control cells Dose of oligonucleotide | | | | |
|---|---|---|---|---|---|---|
| ISIS # | SEQ ID NO | 12.5 nM | 25 nM | 50 nM | 100 nM | 200 nM |
| 330012 | 205 | 42 | 66 | 43 | 45 | 26 |
| 133726 | 36 | 53 | 73 | 56 | 36 | 34 |
| 113529 | 597 | N.D. | N.D. | N.D. | 73 | 97 |
| 13650 | 614 | N.D. | N.D. | N.D. | 74 | 57 |

As demonstrated in Table 16, doses of 25, 50, 100 and 200 nM of ISIS 330012 and 133726 inhibited C-reactive mRNA expression in a dose-dependent manner following 24 hours of oligonucleotide treatment.

In a further embodiment, in the same experiment presented in Table 16, C-reactive protein secreted into the tissue culture media from the cytokine-induced primary human hepatocytes was measured by ELISA using a commercially available kit (ALerCHEK Inc., Portland, Me.) following 24 hours of oligonucleotide treatment. Data, shown in Table 17, are averages from three experiments and are expressed as percent protein secreted relative to cytokine-induced controls. Where present, "N.D." indicates not determined.

TABLE 17

Inhibition of human C-reactive protein secretion in human primary hepatocytes: 24 hour dose response

| | | % Protein secretion relative to cytokine-induced control cells Dose of oligonucleotide | | | | |
|---|---|---|---|---|---|---|
| ISIS # | SEQ ID NO | 12.5 nM | 25 nM | 50 nM | 100 nM | 200 nM |
| 330012 | 205 | 85 | 67 | 61 | 66 | 65 |
| 133726 | 36 | 63 | 67 | 66 | 61 | 68 |
| 113529 | 597 | N.D. | N.D. | N.D. | 80 | 80 |
| 13650 | 614 | N.D. | N.D. | N.D. | 79 | 91 |

As demonstrated in Table 17, ISIS 330012 inhibited C-reactive protein secretion following 24 hours of oligonucleotide treatment.

In a further embodiment, C-reactive protein mRNA levels in cytokine-induced primary human hepatocytes were measured following 48 hours of oligonucleotide treatment. Cells were treated with 12.5, 25, 50, 100 and 200 nM of ISIS 330012 and ISIS 133726. ISIS 13650 and ISIS 113529 served as control oligonucleotides. Cells were treated with 100 and 200 nM of ISIS 113529 and ISIS 13650. Data, shown in Table 18, are averages from three experiments and are expressed as percent mRNA expression relative to cytokine-induced control cells. Where present, "N.D." indicates not determined.

TABLE 18

Inhibition of human C-reactive mRNA expression in human primary hepatocytes: 48 hour dose response

| | | % mRNA expression relative to cytokine-induced control cells Dose of oligonucleotide | | | | |
|---|---|---|---|---|---|---|
| ISIS # | SEQ ID NO | 12.5 nM | 25 nM | 50 nM | 100 nM | 200 nM |
| 330012 | 205 | 73 | 53 | 58 | 27 | 19 |
| 133726 | 36 | 65 | 53 | 39 | 34 | 19 |
| 113529 | 597 | N.D. | N.D. | N.D. | 116 | 79 |
| 13650 | 598 | N.D. | N.D. | N.D. | 116 | 85 |

As demonstrated in Table 18, ISIS 330012 and 133726 inhibited C-reactive mRNA expression in a dose-dependent manner following 48 hours of oligonucleotide treatment.

In a further embodiment, treatment with ISIS 330012 and ISIS 133726 for 48 hours was repeated, and both C-reactive protein mRNA and protein were measured. C-reactive protein was measured by real-time PCR following 48 hours of oligonucleotide treatment. Data, shown in Table 19, are averages from three experiments and are expressed as percent mRNA expression relative to cytokine-induced control cells. Where present, "N.D." indicates not determined.

TABLE 19

Inhibition of human C-reactive protein mRNA expression in human primary hepatocytes: 48 hour dose response

| | | % mRNA expression relative to cytokine-induced control cells Dose of oligonucleotide | | |
|---|---|---|---|---|
| ISIS # | SEQ ID NO | 50 | 100 | 200 |
| 330012 | 205 | 54 | 36 | 17 |
| 133726 | 36 | 72 | 33 | 25 |
| 113529 | 597 | N.D. | N.D. | 112 |

As demonstrated in Table 19, ISIS 330012 and 133726 inhibited C-reactive mRNA expression in a dose-dependent manner following 48 hours of oligonucleotide treatment.

In a further embodiment, in the same experiment presented in Table 19, C-reactive protein secreted into the tissue culture media from the cytokine-induced primary human hepatocytes was measured by ELISA using a commercially available kit (ALerCHEK Inc., Portland, Me.) following 48 hours of oligonucleotide treatment. Data, shown in Table 20, are averages from three experiments and are expressed as percent protein secreted relative to cytokine-induced controls. Where present, "N.D." indicates not determined.

TABLE 20

Inhibition of human C-reactive protein secretion in human primary hepatocytes: 48 hour dose response

| | | % Protein secretion relative to cytokine-induced control cells Dose of oligonucleotide | | |
|---|---|---|---|---|
| ISIS # | SEQ ID NO | 50 | 100 | 200 |
| 330012 | 205 | 40 | 25 | 18 |
| 133726 | 36 | 37 | 18 | 20 |
| 113529 | 597 | N.D. | N.D. | 104 |

As demonstrated in Table 20, ISIS 330012 and 133726 inhibited C-reactive protein expression in a dose-dependent manner following 48 hours of oligonucleotide treatment. At the 200 nM dose, ISIS 133726 and ISIS 330012 were able to lower C-reactive protein mRNA in cytokine-induced cells to levels below basal expression levels, i.e. levels observed in cells not induced with cytokine. Northern and immunoblot analyses also confirmed the reduction in C-reactive protein mRNA and protein expression after 48 hours of oligonucleotide treatment.

Example 34

Sequencing of Cynomolgus Monkey (*Macaca fascicularis*) C-Reactive Protein mRNA In accordance with the present invention, a portion of the cynomolgus monkey C-reactive protein mRNA not available in the art was amplified and sequenced. Positions 537 to 2201 of the human C-reactive protein mRNA sequence (GEN-BANK® accession number M11725.1, incorporated herein as SEQ ID NO: 4) contain the target segment to which ISIS 133726 and ISIS 330012 hybridize. The corresponding segment of Cynomolgus monkey C-reactive protein mRNA was amplified and sequenced, using a series of 8 primer sets designed to the human sequence. Total RNA was purified from Cynomolgus monkey primary hepatocytes (In Vitro Technologies, Gaithersburg, Md.). A reverse transcription was performed to produce cDNA and was followed by approximately 40 rounds of PCR amplification. Following gel purification of the Cynomolgus fragments, the forward and reverse sequencing reactions of each product were performed using the RETROGEN™ kit (Invitrogen). This kit was used to create the single-stranded cDNA and provided reagents for AMPLITAQ™ PCR reaction. The sequenced products were assembled to largely complete the Cynomolgus monkey C-reactive protein mRNA. This Cynomolgus monkey sequence is incorporated herein as SEQ ID NO:615 and is 93% homologous to positions 537 to 2201 of the human C-reactive protein mRNA. An additional sequence that shares 97% homology with human C-reactive protein from positions 101-290 is incorporated herein as SEQ ID NO:616.

Example 35

Antisense Inhibition of Cynomolgus Monkey C-Reactive Protein Expression by Chimeric Phosphorothioate Oligonucleotides Having 2'-MOE Wings and a Deoxy Gap

Dose Response Studies

In a further embodiment, oligonucleotides targeted to human C-reactive protein were selected for additional dose-response studies were tested for their ability to inhibit target mRNA in primary Cynomolgus monkey hepatocytes. Due to the high degree of identity between human and Cynmolgus monkey C-reactive protein, ISIS 133726 (SEQ ID NO:36) and ISIS 330012 (SEQ ID NO:205) hybridize to Cynomolgus monkey C-reactive protein with perfect complementarity, at target sites 1147 and 1195 of the Cynomolgus monkey mRNA disclosed herein (SEQ ID NO:615), respectively. Primary Cynolmolgus monkey hepatocytes were induced with cytokine as described herein for Hep3B cells and were treated with 50, 100 and 200 nM of ISIS 330012 (SEQ ID NO:205) and ISIS 133726 (SEQ ID NO:36). ISIS 113529 (SEQ ID NO:597) served as the control oligonucleotide. Cells were treated with 150 and 300 nM of ISIS 113529.

C-reactive protein mRNA levels were measured following 24 hours of oligonucleotide treatment. Data, shown in Table 21, are averages from three experiments and are expressed as percent mRNA expression relative to cytokine-induced controls. Where present, "N.D." indicates not determined.

TABLE 21

Inhibition of Cynomolgus monkey C-reactive protein mRNA expression in human primary hepatocytes: 24 hour dose response

| | | % mRNA xpression elative to cytokine-induced control cells Dose of oligonucleotide | | | |
|---|---|---|---|---|---|
| ISIS # | SEQ ID NO | 25 nM | 50 nM | 150 nM | 300 nM |
| 330012 | 205 | 66 | 62 | 48 | 13 |
| 133726 | 36 | 104 | 111 | 47 | 22 |
| 113529 | 597 | N.D. | N.D. | 130 | 86 |

As demonstrated in Table 21, ISIS 330012 (at all doses tested) and ISIS 133726 (at 150 and 300 nM) inhibited C-reactive protein mRNA expression in a dose-dependent manner following 24 hours of oligonucleotide treatment.

In a further embodiment, in the same experiment presented in Table 21, C-reactive protein secreted into the tissue culture media from the cytokine-induced primary Cynomolgus hepatocytes was measured by ELISA using a commercially available kit (ALerCHEK Inc., Portland, Me.) following 24 hours of oligonucleotide treatment. Data, shown in Table 22, are averages from three experiments and are expressed as percent protein secreted relative to cytokine-induced control cells. Where present, "N.D." indicates not determined.

TABLE 22

Inhibition of Cynomolgus monkey C-reactive protein secretion in Cynomolgus monkey primary hepatocytes: 24 hour dose response

| | | % protein secretion relative to cytokine induced control cells Dose of oligonucleotide | | |
|---|---|---|---|---|
| ISIS # | SEQ ID NO | 50 | 100 | 200 |
| 330012 | 205 | 40 | 25 | 18 |
| 133726 | 36 | 37 | 18 | 20 |
| 113529 | 597 | N.D. | N.D. | 104 |

As demonstrated in Table 22, ISIS 330012 and 133726 inhibited C-reactive protein secretion in a dose-dependent manner following 48 hours of oligonucleotide treatment.

These data demonstrate that ISIS 133726 and ISIS 330012, while designed to target the human C-reactive protein mRNA, are capable of inhibiting both C-reactive protein mRNA and secreted protein in Cynomolgus monkey primary hepatocytes, and are therefore antisense oligonucleotides that can be used to test the inhibition of Cynomolgus monkey C-reactive protein in vivo.

Example 36

Antisense Inhibition of C-Reactive Protein In Vivo Cynomolgus Monkeys

Cynomolgus monkeys (male or female) are useful to evaluate antisense oligonucleotides for their potential to lower C-reactive protein mRNA or protein levels, as well as phenotypic endpoints associated with C-reactive protein including, but not limited to cardiovascular indicators, atherosclerosis, lipid diseases, obesity, and plaque formation. One study includes normal and induced hypercholesterolemic monkeys fed diets that are normal or high in lipid and cholesterol. Parameters that are observed during the test period include:

total plasma cholesterol, LDL-cholesterol, HDL-cholesterol, triglyceride, arterial wall cholesterol content, and coronary intimal thickening.

In a further embodiment, Cynomolgus monkeys fed an atherogenic diet develop atherosclerosis with many similarities to atherosclerosis of humans and are used to evaluate the potential of antisense compounds to prevent or ameliorate atherosclerosis. Female Cynomolgus macaques share several similarities in lipoproteins and the cardiovascular system with humans. In addition to these characteristics, there are similarities in reproductive biology. The Cynomolgus female has a 28-day menstrual cycle like that of women. Plasma hormone concentrations have been measured throughout the Cynomolgus menstrual cycle, and the duration of the follicular and luteal phases, as well as plasma estradiol and progesterone concentrations across the cycle, are also remarkably similar to those in women.

Antisense oligonucleotides targeted to C-reactive protein are evaluated for efficacy and toxicity in Cynomolgus monkeys. The oligonucleotides chosen for these studies hybridize to two distinct regions of the 3' UTR of both human and monkey C-reactive protein mRNA. ISIS 133726 (SEQ ID NO: 36) and ISIS 330012 (SEQ ID NO:205) are chimeric oligonucleotides with a 5~10~5 configuration, as described herein. ISIS 353512 (SEQ ID NO:36) and ISIS 353491 (SEQ ID NO:205) are the same chimeric oligonucleotides, respectively, with a 3~14~3 configuration, as described herein. Cynomolgus monkeys are treated as described in Table 23. Each of the 9 groups presented in Table 23 consists of 5 animals, and the number of males and females in each of these groups is indicated.

TABLE 23

Treatment of Cynomolgus monkeys with oligonucleotides targeted to C-reactive protein: study design

| Group # | Treatment | Number of Females/Males | Dose mg/kg |
|---|---|---|---|
| 1 | Saline | 3/2 | |
| 2 | ISIS 330012 | 2/3 | 7 |
| 3 | ISIS 330012 | 3/2 | 20 |
| 4 | ISIS 133726 | 2/3 | 7 |
| 5 | ISIS 133726 | 3/2 | 20 |
| 6 | ISIS 353512 | 2/3 | 7 |
| 7 | ISIS 353512 | 3/2 | 20 |
| 8 | ISIS 353491 | 2/3 | 7 |
| 9 | ISIS 353491 | 3/2 | 20 |

All animals are dosed via subcutaneous injection on the study days 1, 3, 5, 8, 11, 15, 18, 22, 25 and 29. The first day of dosing is designated Day 1. The animals are evaluated for changes in general appearance and behavior, food consumption and body weight. Blood samples are collected at 1, 2 and 3 week intervals prior to the start of the study, on days 1 and 29 just prior to dosing and at 1, 2, 4 and 24 hours after dosing and on days 8, 15 and 22 just prior to dosing. Blood samples are subjected to clinical pathology evaluations, which include serum chemistry, hematology, coagulation and urinalysis parameters. Serum chemistry parameters analyzed include sodium, potassium, chloride, carbon dioxide, total bilirubin, alkaline phosphatase (ALP), lactate dehydrogenase (LDH), aspartate aminotransferase (AST), alanine aminotransferase (ALT), gamma-glutamyltransferase (GGT), calcium, phosphorus, blood urea nitrogen (BUN), creatinine, total protein, albumin, globulin, albumin/globulin ratio, glucose, cholesterol and triglycerides. Hematology parameters include red blood cell (RBC) counts, white blood cell (WBC) counts, hemoglobin concentration, hematocrit, reticulocyte counts, plasmodium evaluation, mean corpuscular hemoglobin (MCH), mean corpuscular volume (MCV), mean corpuscular hemoglobin concentration (MCHC), platelet counts and blood cell morphology. Coagulation parameters that are evaluated include activated partial thromboplastin time (APTT) and prothromgin time (PT). Urinalysis parameters that are evaluated include color, character, pH, specific gravity, leukocyte esterase, nitrite, urobilinogen, protein, glucose, ketones, bilirubin, occult blood and microscopics. C-reactive protein in serum is measured using an immunochemiluminescence assay (ICMA). All clinical parameters are measured using routine procedures known in the art. Additionally, a toxicokinetic analysis is performed to determine the concentration of C-reactive protein oligonucleotide in serum. Furthermore, serum levels of cytokines and chemokines, including interleukin-1, interleukin-6, interleukin-8, interferon-gamma, tumor necrosis factor-alpha, monocyte chemoattractant protein-1 (MCP-1), macrophage inflammatory protein-1α (MIP-1α), macrophage inflammatory protein-1β (MIP-1β), and regulated-on-activation, normal T cell expressed and secreted cytokine (RANTES), are measured to determine the extent of any immune or inflammatory response.

On day 30 of the study, 24 hours after the final dose of saline or oligonucleotide, animals are sacrificed. Final body weights are recorded, and a gross necropsy examination is conducted to evaluate the carcass, muscular/skeletal system, all external surfaces and orifices, cranial cavity and external surface of the brain, neck with associated organs and tissues, thoraci, abdominal and pelvic cavities with associated organs and tissues. Urine is collected from the bladder and analyzed as previously described herein. Kidney, liver, lung, heart and spleen weights are recorded. Cardiovascular, digestive, lymphoid/hematopoietic, urogenital and endocrine tissues are collected and preserved in 10% neutral-buffered formalin. Tissues collected from animals treated with saline and 20 mg/kg oligonucleotide, following preservation in 10% neutral-buffered formalin, are embedded in paraffin, sectioned, stained with hematoxylin and eosin and examined for pathological abnormalities. Bone marrow smears are collected for microscopic examination in cases where bone marrow sections reveal changes or abnormalities. A portion of the liver tissue collected, which has not been preserved in formalin, is homogenized in a buffer that inhibits Rnase activity and is evaluated for C-reactive protein mRNA expression by real-time PCR as described herein. The parameters evaluated in this study determine the efficacy and toxicity of antisense oligonucleotides targeted to C-reactive protein.

Example 37

Antisense Oligonucleotides Targeted to Human C-Reactive Protein In Vivo

Lean Mouse Study

In a further embodiment, antisense oligonucleotides targeted to human C-reactive protein were tested for their effects on serum lipids, serum glucose and indicators of toxicity. Male C57Bl/6 mice (Charles River Laboratories, Wilmington, Mass.) were fed a standard rodent diet. Mice were given intraperitoneal injections of 25 and 50 mg/kg of each of the following antisense oligonucleotides: ISIS 133726 (SEQ ID NO:36), ISIS 329956 (SEQ ID NO:149), ISIS 330012 (SEQ ID NO:205) and ISIS 330031 (SEQ ID NO:224). Each oligonucleotide-treated group consisted of 5 mice. A total of 10 saline-injected animals served as controls. Injections were administered twice weekly for a period of 4 weeks. At the end of the treatment period, mice were sacrificed. Body, liver and spleen weights were recorded and exhibited no significant changes.

Serum was collected for routine clinical analysis of ALT, AST, cholesterol (CHOL), glucose (GLUC), HDL-cholesterol (HDL), LDL-cholesterol (LDL), triglycerides (TRIG) and non-esterified free fatty acids (NEFA). These parameters were measured by routine procedures using an Olympus Clinical Analyzer (Olympus America Inc., Melville, N.Y.). The data are presented in Table 24.

TABLE 24

Serum chemistry analysis of mice treated with antisense oligonucleotides targeted to human C-reactive protein

| Treatment | Dose mg/kg | ALT IU/L | AST IU/L | CHOL mg/dL | GLUC mg/dL | HDL mg/dL | TG mg/dL | LDL mg/dL | NEFA mEq/L |
|---|---|---|---|---|---|---|---|---|---|
| SALINE |  | 45 | 86 | 81 | 187 | 63 | 132 | 14 | 1.0 |
| 133726 | 25 | 36 | 62 | 85 | 172 | 63 | 158 | 16 | 1.2 |
|  | 50 | 42 | 64 | 73 | 179 | 54 | 139 | 15 | 1.4 |
| 329956 | 25 | 31 | 57 | 98 | 172 | 77 | 117 | 17 | 1.5 |
|  | 50 | 37 | 60 | 105 | 176 | 82 | 149 | 18 | 1.7 |
| 330012 | 25 | 34 | 71 | 89 | 200 | 71 | 123 | 13 | 1.5 |
|  | 50 | 35 | 59 | 93 | 187 | 75 | 115 | 12 | 1.5 |
| 330031 | 25 | 36 | 94 | 80 | 194 | 63 | 131 | 14 | 1.5 |
|  | 50 | 153 | 443 | 150 | 152 | 83 | 131 | 66 | 1.6 |

These data reveal that only the 50 mg/kg dose of ISIS 330031 resulted in a significant increase in the liver transaminases ALT and AST, suggesting a hepatotoxic effect at the highest dose of ISIS 330031. Treatment with ISIS 330031 at 50 mg/kg also resulted in an increase in cholesterol and LDL-cholesterol. A moderate increase in cholesterol was observed in animals treated with ISIS 329956 at 50 mg/kg. Increases in non-esterified free fatty acids were observed in mice treated with all oligonucleotides used in this study.

These data reveal that antisense oligonucleotides targeted to human C-reactive protein effectively inhibited target expression in lean mice, without producing overt toxicities.

Example 38

Antisense Inhibition of C-Reactive Protein In Vivo

Rat Study

In a further embodiment, antisense oligonucleotides targeted to C-reactive protein were tested in an additional animal model. Male Sprague Dawley rats (Charles River Laboratories, Wilmington, Mass.), maintained on a standard rodent diet, received intraperitoneal injections of 75 and 100 mg/kg ISIS 197178 (SEQ ID NO:275) once per week for a period of 6 weeks. Saline-injected animals served as controls. Each treatment group consisted of 5 animals. At the end of the treatment period, the animals were sacrificed and evaluated for C-reactive protein mRNA and protein expression and liver, as well as C-reactive protein expression in serum. mRNA was measured by real-time PCR as described by other examples herein. Protein was measured by ELISA using a commercially available kit (BD Biosciences, Bedford, Mass.). The data, averaged from the 5 animals in each treatment group, are normalized to results from saline-treated animals and are presented in Table 25.

TABLE 25

Effects of antisense inhibition of C-reactive protein in rats

| | % control Dose of ISIS 197178 | |
|---|---|---|
| C-reactive protein: | 75 mg/kg | 100 mg/kg |
| mRNA | 12 | 13 |
| protein, serum | 15 | 15 |
| protein, liver | 32 | 33 |

TABLE 25-continued

Effects of antisense inhibition of C-reactive protein in rats

| | % control Dose of ISIS 197178 | |
|---|---|---|
| C-reactive protein: | 75 mg/kg | 100 mg/kg |

These data demonstrate that ISIS 197178 markedly decreased liver C-reactive protein mRNA and protein, as well as serum protein. Reduction of serum C-reactive protein levels was confirmed by immunoblot analysis using the rat C-reactive protein antibody from the ELISA kit. These results reveal that reduction in liver C-reactive protein mRNA lowers serum C-reactive protein levels, illustrating an important link between liver C-reactive protein production and serum levels.

Example 39

Specificity of Oligonucleotides Targeted to C-Reactive Protein

In a further embodiment, the specificity of ISIS 330012 to C-reactive protein mRNA was investigated. A BLAST search was conducted to determine whether ISIS 330012 could hybridize to genes other than C-reactive protein. This search revealed several genes with sequences that harbor potential binding sites for ISIS 330012. These genes are shown in Table 26, where the number of mismatches is indicated. All potential ISIS 330012 target sites contain 2-3 mismatched nucleotides with respect to ISIS 330012. Also shown are the Unigene ID accession numbers of sequences, both of which are available through the National Center for Biotechnology Information database. The number of times the binding site is repeated in the gene sequence is indicated in the "count" column in Table 26.

TABLE 26

Gene sequences sharing 2-3 mismatches with C-reactive protein at the ISIS 330012 binding site

| # Mismatches | Unigene ID | GENBANK ® Accession # | Gene Name | Count |
|---|---|---|---|---|
| 2 | Hs.256184 | NM_001404.1 | eukaryotic translation elongation factor 1 gamma | 1 |
| 2 | Hs.441043 | NM_014817.1 | importin 11 | 1 |
| 2 | Hs.54971 | NM_016505.1 | putative S1 RNA binding domain protein | 1 |
| 3 | Hs.11417 | NM_006423.1 | Rab acceptor 1 (prenylated) | 3 |
| 3 | Hs.121549 | NM_145752.1 | CDP-diacylglycerol--inositol 3-phosphatidyltransferase (phosphatidylinositol synthase) | 1 |
| 3 | Hs.131842 | NM_015255.1 | ubiquitin ligase E3 alpha-II | 2 |
| 3 | Hs.135226 | NM_001908.1 | cathepsin B | 1 |
| 3 | Hs.135805 | BC016490.1 | skeletrophin | 1 |
| 3 | Hs.180577 | NM_002087.1 | granulin | 1 |
| 3 | Hs.200063 | NM_015401.1 | histone deacetylase 7A | 1 |
| 3 | Hs.20157 | NM_025197.1 | CDK5 regulatory subunit associated protein 3 | 1 |
| 3 | Hs.248017 | NM_014364.1 | glyceraldehyde-3-phosphate dehydrogenase, testis-specific | 1 |
| 3 | Hs.274268 | NM_145648.1 | solute carrier family 15, member 4 | 1 |
| 3 | Hs.387667 | AF106698.1 | peroxisome proliferative activated receptor, gamma | 1 |
| 3 | Hs.418167 | NM_000477.3 | albumin | 2 |

To test whether ISIS 330012 affects the expression of the genes in Table 26, primary human hepatocytes, cultured as described herein, were treated with 200 nM ISIS 330012 for 48 hours. Expression of the genes in Table 26 was measured by real-time PCR as described herein, using primers and probes designed to publicly available sequences. These data revealed that ISIS 330012 did not modulate the expression of any of the genes in Table 26, illustrating that, in primary hepatocytes, ISIS 330012 specifically hybridizes to, and inhibits, C-reactive protein mRNA.

Example 40

Cell Proliferation and Survival in Response to Cells Treated with Oligomeric Compounds Targeted to C-Reactive Protein Cell cycle regulation is the basis for various cancer therapeutics. Unregulated cell proliferation is a characteristic of cancer cells, thus most current chemotherapy agents target dividing cells, for example, by blocking the synthesis of new DNA required for cell division. However, cells in healthy tissues are also affected by agents that modulate cell proliferation.

In some cases, a cell cycle inhibitor causes apoptosis in cancer cells, but allows normal cells to undergo growth arrest and therefore remain unaffected (Blagosklonny, *Bioessays,* 1999, 21, 704-709; Chen et al., *Cancer Res.,* 1997, 57, 2013-2019; Evan and Littlewood, *Science,* 1998, 281, 1317-1322; Lees and Weinberg, *Proc. Natl. Acad. Sci. USA,* 1999, 96, 4221-4223). An example of sensitization to anti-cancer agents is observed in cells that have reduced or absent expression of the tumor suppressor genes p53 (Bunz et al., *Science,* 1998, 282, 1497-1501; Bunz et al., *J. Clin. Invest.,* 1999, 104, 263-269; Stewart et al., *Cancer Res.,* 1999, 59, 3831-3837; Wahl et al., *Nat. Med.,* 1996, 2, 72-79). However, cancer cells often escape apoptosis (Lowe and Lin, *Carcinogenesis,* 2000, 21, 485-495; Reed, *Cancer J. Sci. Am.,* 1998, 4 Suppl 1, S8-14). Further disruption of cell cycle checkpoints in cancer cells can increase sensitivity to chemotherapy while allowing normal cells to take refuge in G1 and remain unaffected. Cell cycle assays are employed to identify genes, such as p53, whose inhibition sensitizes cells to anti-cancer agents.

Cell Cycle Assay

The effect of oligomeric compounds targeted to C-reactive protein were examined in normal human mammary epithelial cells (HMECs) as well as in two breast carcinoma cell lines, MCF7 and T47D. All of the cell lines are obtained from the American Type Culture Collection (Manassas, Va.). The latter two cell lines express similar genes. MCF7 cells express the tumor suppressor p53, while T47D cells are deficient in p53. MCF-7 and HMECs cells are routinely cultured in DMEM low glucose (Invitrogen Life Technologies, Carlsbad, Calif.) supplemented with 10% fetal bovine serum (Invitrogen Life Technologies, Carlsbad, Calif.). T47D cells were cultured in DMEM High glucose media (Invitrogen Life Technologies, Carlsbad, Calif.) supplemented with 10% fetal bovine serum. Cells were routinely passaged by trypsinization and dilution when they reached approximately 90% confluence. Cells were plated in 24-well plates at approximately 50,000-60,000 cells per well for HMEC cells, approximately 140,000 cells per well for MCF-7 and approximately 170,000 cells per well for T47D cells, and allowed to attach to wells overnight.

ISIS 133726 (SEQ ID NO:36) was used to test the effects of antisense inhibition of C-reactive protein on cell cycle progression. A randomized control oligonucleotide, ISIS 29848 (NNNNNNNNNNNNNNNNNNNN; where N is A, T, C or G; herein incorporated as SEQ ID NO:617) was used a negative control, a compound that does not modulate cell cycle progression. In addition, a positive control for the inhibition of cell proliferation was assayed. The positive control was ISIS 148715 (TTGTCCCAGTCCCAGGCCTC; herein incorporated as SEQ ID NO:618), which targets human Jagged2 and is known to inhibit cell cycle progression. ISIS 29248 and ISIS 148715 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Oligonucleotide was mixed with LIPOFECTIN™ reagent (Invitrogen Life Technologies, Carlsbad, Calif.) in OPTI-MEM™ medium (Invitrogen Life Technologies, Carlsbad, Calif.) to achieve a final concentration of 200 nM of oligonucleotide and 6 μg/mL LIPOFECTIN™ reagent. Before adding to cells, the oligonucleotide, LIPOFECTIN™ reagent and OPTI-MEM™ medium were mixed thoroughly and incubated for 0.5 hrs. The medium was removed from the plates and the plates were tapped on sterile gauze. Each well containing T47D or MCF7 cells was washed with 150 μl of phosphate-buffered saline. Each well containing HMECs was washed with 150 μL of Hank's balanced salt solution. The wash buffer in each well was replaced with 100 μL of the oligonucleotide/OPTI-MEM™ medium/LIPOFECTIN™ reagent cocktail. Control cells received LIPOFECTIN™ reagent only. The plates were incubated for 4 hours at 37° C., after which the medium was removed and the plate was tapped on sterile gauze. 100 μl of full growth medium was added to each well. After 72 hours, routine procedures were used to prepare cells for flow cytometry analysis and cells were stained with propidium iodide to generate a cell cycle profile using a flow cytometer. The cell cycle profile was analyzed with the ModFit program (Verity Software House, Inc., Topsham Me.).

Fragmentation of nuclear DNA is a hallmark of apoptosis and produces an increase in cells with a hypodiploid DNA content, which are categorized as "subG1". An increase in cells in G1 phase is indicative of a cell cycle arrest prior to entry into S phase; an increase in cells in S phase is indicative of cell cycle arrest during DNA synthesis; and an increase in cells in the G2/M phase is indicative of cell cycle arrest just prior to or during mitosis. Data are expressed as percentage of cells in each phase relative to the cell cycle profile of untreated control cells and are shown in Table 27.

TABLE 27

Cell cycle profile of cells treated with oligomeric compounds targeted to C-reactive protein

| | Treatment | Sub G1 | G1 Phase | S Phase | G2/M Phase |
|---|---|---|---|---|---|
| HMEC | ISIS 133726 | 135 | 101 | 80 | 111 |
| | ISIS 29848 | 117 | 99 | 82 | 113 |
| | ISIS 148715 | 47 | 99 | 88 | 107 |
| MCF7 | ISIS 133726 | 116 | 110 | 83 | 103 |
| | ISIS 29848 | 130 | 106 | 91 | 98 |
| | ISIS 148715 | 42 | 109 | 80 | 110 |
| T47D | ISIS 133726 | 349 | 82 | 111 | 130 |
| | ISIS 29848 | 154 | 86 | 111 | 118 |
| | ISIS 148715 | 62 | 83 | 116 | 124 |

These data reveal that ISIS 133726 did not significantly affect cell cycle progression in HMECs, MCF7 cells or T47D cells.

Caspase Assay

Programmed cell death, or apoptosis, is an important aspect of various biological processes, including normal cell turnover, as well as immune system and embryonic development. Apoptosis involves the activation of caspases, a family of intracellular proteases through which a cascade of events leads to the cleavage of a select set of proteins. The caspase family can be divided into two groups: the initiator caspases, such as caspase-8 and -9, and the executioner caspases, such as caspase-3, -6 and -7, which are activated by the initiator caspases. The caspase family contains at least 14 members, with differing substrate preferences (Thornberry and Lazebnik, Science, 1998, 281, 1312-1316). A caspase assay is utilized to identify genes whose inhibition selectively causes apoptosis in breast carcinoma cell lines, without affecting normal cells, and to identify genes whose inhibition results in cell death in the p53-deficient T47D cells, and not in the MCF7 cells which express p53 (Ross et al., Nat. Genet., 2000, 24, 227-235; Scherf et al., Nat. Genet., 2000, 24, 236-244). The chemotherapeutic drugs taxol, cisplatin, etoposide, gemcitabine, camptothecin, aphidicolin and 5-fluorouracil all have been shown to induce apoptosis in a caspase-dependent manner.

In a further embodiment of the invention, oligomeric compounds targeted to C-reactive protein were examined in normal human mammary epithelial cells (HMECs) as well as in two breast carcinoma cell lines, MCF7 and T47D. HMECs and MCF7 cells express p53, whereas T47D cells do not express this tumor suppressor gene. Cells were cultured as described for the cell cycle assay in 96-well plates with black sides and flat, transparent bottoms (Corning Incorporated, Corning, N.Y.). DMEM media, with and without phenol red, were obtained from Invitrogen Life Technologies (Carlsbad, Calif.). MEGM media, with and without phenol red, were obtained from Cambrex Bioscience (Walkersville, Md.).

ISIS 133726 (SEQ ID NO:36) was used to test the effects of antisense inhibition of C-reactive protein on caspase-activity. A randomized control oligonucleotide, ISIS 29848 (NNNNNNNNNNNNNNNNNNNN; where N is A, T, C or G; incorporated herein as SEQ ID NO:617) was used as a negative control, a compound that does not effect caspase activity. As a positive control for caspase activation, an oligonucleotide targeted to human Jagged2 ISIS 148715 (SEQ ID NO:618) or human Notch1 ISIS 226844 (GCCCTCCATGCTGGCACAGG; herein incorporated as SEQ ID NO:619) was also assayed. Both of these genes are known to induce caspase activity, and subsequently apoptosis, when inhibited. ISIS 29248, ISIS 148715 and ISIS 226844 are all chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Oligonucleotide was mixed with LIPOFECTIN™ reagent (Invitrogen Life Technologies, Carlsbad, Calif.) in OPTI-MEM™ medium (Invitrogen Life Technologies, Carlsbad, Calif.) to achieve a final concentration of 200 nM of oligonucleotide and 6 μg/mL LIPOFECTIN™ reagent. Before adding to cells, the oligonucleotide, LIPOFECTIN™ reagent and OPTI-MEM™ medium were mixed thoroughly and incubated for 0.5 hrs. The medium was removed from the plates and the plates were tapped on sterile gauze. Each well was washed in 150 μl of phosphate-buffered saline (150 μL Hank's balanced salt solution for HMEC cells). The wash buffer in each well was replaced with 100 μL of the oligonucleotide/OPTI-MEM™ medium/LIPOFECTIN™ reagent cocktail. Compounds targeted to C-reactive protein, ISIS 226844 and ISIS 148715 were tested in triplicate, and ISIS 29848 was tested in up to six replicate wells. Untreated control cells received LIPOFECTIN™ reagent only. The plates were incubated for 4 hours at 37° C., after which the medium was removed and the plate was tapped on sterile gauze. 100 μl of full growth medium without phenol red was added to each well.

Caspase-3 activity was evaluated with a fluorometric HTS Caspase-3 assay (Catalog #HTS02; EMD Biosciences, San Diego, Calif.) that detects cleavage after aspartate residues in the peptide sequence (DEVD). The DEVD substrate is labeled with a fluorescent molecule, which exhibits a blue to green shift in fluorescence upon cleavage by caspase-3. Active caspase-3 in the oligonucleotide treated cells is measured by this assay according to the manufacturer's instructions. 48 hours following oligonucleotide treatment, 50 uL of assay buffer containing 10 μM dithiothreitol was added to each well, followed by addition 20 uL of the caspase-3 fluorescent substrate conjugate. Fluorescence in wells was immediately detected (excitation/emission 400/505 nm) using a fluorescent plate reader (SPECTRAMAX™ GEMINIXS™ reader, Molecular Devices, Sunnyvale, Calif.). The plate was covered and incubated at 37° C. for and additional three hours, after which the fluorescence was again measured (excitation/emission 400/505 nm). The value at time zero was subtracted from the measurement obtained at 3 hours. The measurement obtained from the untreated control cells was designated as 100% activity.

The experiment was replicated in each of the 3 cell types, HMECs, T47D and MCF7 and the results are shown in Table 28. From these data, values for caspase activity above or below 100% are considered to indicate that the compound has the ability to stimulate or inhibit caspase activity, respectively. The data are shown as percent increase in fluorescence relative to untreated control values.

TABLE 28

Effects of antisense inhibition of C-reactive protein on apoptosis in the caspase assay

| Cell Type | Treatment | Percent relative to untreated control |
| --- | --- | --- |
| HMEC | ISIS 133726 | 148 |
|  | ISIS 29848 | 275 |
|  | ISIS 148715 | 1006 |
| MCF7 | ISIS 133726 | 77 |
|  | ISIS 29848 | 103 |
|  | ISIS 226844 | 199 |
| T47D | ISIS 133726 | 125 |
|  | ISIS 29848 | 154 |
|  | ISIS 148715 | 380 |

From these data it is evident that inhibition of C-reactive protein expression by ISIS 133726 resulted in an inhibition of apoptosis in MCF7 cells, as compared to untreated control cells controls. These data indicate that this oligomeric compound is a candidate agent with applications in the treatment of conditions in which inhibition of apoptosis is desirable, for example, in neurodegenerative disorders.

Example 41

Assay for Inhibition of Angiogenesis Using Oligomeric Compounds Targeted to C-Reactive Protein Angiogenesis is the growth of new blood vessels (veins and arteries) by endothelial cells. This process is important in the development of a number of human diseases, and is believed to be particularly important in regulating the growth of solid tumors. Without new vessel formation it is believed that tumors will not grow beyond a few millimeters in size. In addition to their use as anti-cancer agents, inhibitors of angiogenesis have potential for the treatment of diabetic retinopathy, cardiovascular disease, rheumatoid arthritis and psoriasis (Carmeliet and Jain, *Nature,* 2000, 407, 249-257; Freedman and Isner, *J. Mol. Cell. Cardiol.,* 2001, 33, 379-393; Jackson et al., *Faseb J.,* 1997, 11, 457-465; Saaristo et al., *Oncogene,* 2000, 19, 6122-6129; Weber and De Bandt, *Joint Bone Spine,* 2000, 67, 366-383; Yoshida et al., *Histol. Histopathol.,* 1999, 14, 1287-1294).

Endothelial Tube Formation Assay as a Measure of Angiogenesis

Angiogenesis is stimulated by numerous factors that promote interaction of endothelial cells with each other and with extracellular matrix molecules, resulting in the formation of capillary tubes. This morphogenic process is necessary for the delivery of oxygen to nearby tissues and plays an essential role in embryonic development, wound healing, and tumor growth (Carmeliet and Jain, *Nature,* 2000, 407, 249-257). Moreover, this process can be reproduced in a tissue culture assay that evaluated the formation of tube-like structures by endothelial cells. There are several different variations of the assay that use different matrices, such as collagen I (Kanayasu et al., *Lipids,* 1991, 26, 271-276), Matrigel (Yamagishi et al., *J. Biol. Chem.,* 1997, 272, 8723-8730) and fibrin (Bach et al., *Exp. Cell Res.,* 1998, 238, 324-334), as growth substrates for the cells. In this assay, HUVECs are plated on a matrix derived from the Engelbreth-Holm-Swarm mouse tumor, which is very similar to Matrigel (Kleinman et al., *Biochemistry,* 1986, 25, 312-318; Madri and Pratt, *J. Histochem. Cytochem.,* 1986, 34, 85-91). Untreated HUVECs form tube-like structures when grown on this substrate. Loss of tube formation in vitro has been correlated with the inhibition of angiogenesis in vivo (Carmeliet and Jain, *Nature,* 2000, 407, 249-257; Zhang et al., *Cancer Res.,* 2002, 62, 2034-2042), which supports the use of in vitro tube formation as an endpoint for angiogenesis.

In a further embodiment, primary human umbilical vein endothelial cells (HuVECs) were used to measure the effects of oligomeric compounds targeted to C-reactive protein on tube formation activity. HuVECs were routinely cultured in EBM (Clonetics Corporation, Walkersville, Md.) supplemented with SingleQuots supplements (Clonetics Corporation, Walkersville, Md.). Cells were routinely passaged by trypsinization and dilution when they reached approximately 90% confluence and were maintained for up to 15 passages. HuVECs are plated at approximately 3000 cells/well in 96-well plates. One day later, cells are transfected with antisense oligonucleotides. The tube formation assay is performed using an in vitro Angiogenesis Assay Kit (Chemicon International, Temecula, Calif.).

ISIS 133726 (SEQ ID NO:36) was used to test the effects of inhibition of C-reactive protein on endothelial tube formation. A randomized control oligonucleotide, ISIS 29848 (NNNNNNNNNNNNNNNNNNNN; where N is A, T, C or G; herein incorporated as SEQ ID NO:617) served as a negative control, a compound that does not affect tube formation. ISIS 196103 (AGCCCATTGCTGGACATGCA, incorporated herein as SEQ ID NO:620) which is targeted to integrin-β3 and is known to inhibit endothelial tube formation, was used as a positive control Oligonucleotide was mixed with LIPOFECTIN™ reagent (Invitrogen Life Technologies, Carlsbad, Calif.) in OPTI-MEM™ medium (Invitrogen Life Technologies, Carlsbad, Calif.) to achieve a final concentration of 75 nM of oligonucleotide and 2.25 µg/mL LIPOFECTIN™ reagent. Before adding to cells, the oligonucleotide, LIPOFECTIN™ reagent and OPTI-MEM™ medium were mixed thoroughly and incubated for 0.5 hrs. Untreated control cells received LIPOFECTIN™ reagent only. The medium was removed from the plates and the plates were tapped on sterile gauze. Each well was washed in 150 µl of phosphate-buffered saline. The wash buffer in each well was replaced with 100 µL of the oligonucleotide/OPTI-MEM™ medium/LIPOFECTIN™ reagent cocktail. ISIS 133726 and ISIS 196103 were tested in triplicate, and ISIS 29848 was tested in up to six replicates. The plates were incubated for 4 hours at 37° C., after which the medium was removed and the plate was tapped on sterile gauze. 100 µl of full growth medium was added to each well. Fifty hours after transfection, cells are transferred to 96-well plates coated with ECMa-trix™ (Chemicon Inter-national). Under these conditions, untreated HUVECs form tube-like structures. After an overnight incubation at 37° C., treated and untreated cells are inspected by light microscopy. Individual wells are assigned discrete scores from 1 to 5 depending on the extent of tube formation. A score of 1 refers to a well with no tube formation while a score of 5 is given to wells where all cells are forming an extensive tubular network. Results are expressed as percent tube formation relative to untreated control samples. Treatment with ISIS 133726, ISIS 29848 and ISIS 196103 resulted in 81%, 100% and 51% tube formation, respectively. These results illustrate that ISIS 133726 inhibited tube formation and is thus a candidate agent with applications in the treatment of conditions where the inhibition of angiogenesis is desirable, for example, in the treatment of cancer, diabetic retinopathy, cardiovascular disease, rheumatoid arthritis and psoriasis.

Matrix Metalloproteinase Activity

During angiogenesis, endothelial cells must degrade the extracellular matrix (ECM) and thus secrete matrix metalloproteinases (MMPS) in order to accomplish this degradation. MMPs are a family of zinc-dependent endopeptidases that fall into eight distinct classes: five are secreted and three are membrane-type MMPs (MT-MMPs) (Egeblad and Werb, *J. Cell Science,* 2002, 2, 161-174). MMPs exert their effects by cleaving a diverse group of substrates, which include not only structural components of the extracellular matrix, but also growth-factor-binding proteins, growth-factor pre-cursors, receptor tyrosine-kinases, cell-adhesion molecules and other proteinases (Xu et al., *J. Cell Biol.,* 2002, 154, 1069-1080).

In a further embodiment, the antisense inhibition of apolipoprotein B was evaluated for effects on MMP activity in the media above human umbilical-vein endothelial cells (HUVECs). MMP activity was measured using the EnzChek Gelatinase/Collagenase Assay Kit (Molecular Probes, Eugene, Oreg.). HUVECs are cultured as described for the tube formation assay. HUVECs are plated at approximately 4000 cells per well in 96-well plates and transfected one day later.

HUVECs were treated with ISIS 133726 (SEQ ID NO:36) to inhibit C-reactive protein expression. An oligonucleotide with a randomized sequence, ISIS 29848 (NNNNNNNNNNNNNNNNNNNN; where N is A, T, C or G; herein incorporated as SEQ ID NO:617) served as a negative control, or a treatment not expected to affect MMP activity. ISIS 25237 (GCCCATTGCTGGACATGC, SEQ ID NO:621) targets integrin beta 3 and was used as a positive control for the inhibition of MMP activity. ISIS 25237 is a chimeric oligonucleotide ("gapmers") 18 nucleotides in length, composed of a central "gap" region consisting of ten 2'-deoxynucleotides, which is flanked on both sides (5' and 3' directions) by four-nucleotide "wings". The wings are composed of 2'-O-methoxyethyl (2'-MOE) nucleotides. The internucleoside (backbone) linkages are phosphorothioate (P=S) throughout the oligonucleotides. All cytidine residues are 5-methylcytidines.

Cells were treated as described for the tube formation assay, with 75 nM of oligonucleotide and 2.25 µg/mL LIPOFECTIN™ reagent. ISIS 133726 and ISIS 25237 were tested in triplicate, and the ISIS 29848 was tested in up to six replicates. The plates were incubated for approximately 4 hours at 37° C., after which the medium was removed and the plate was tapped on sterile gauze. 100 µl of full growth medium was added to each well. Approximately 50 hours after transfection, a p-aminophenylmercuric acetate (APMA, Sigma-Aldrich, St. Louis, Mo.) solution is added to each well of a Corning-Costar 96-well clear bottom plate (VWR International, Brisbane, Calif.). The APMA solution is used to promote cleavage of inactive MMP precursor proteins. Media above the HUVECs is then transferred to the wells in the 96-well plate. After 30 minutes, the quenched, fluorogenic MMP cleavage substrate is added, and baseline fluorescence is read immediately at 485 nm excitation/530 nm emission. Following an overnight incubation at 37° C. in the dark, plates are read again to determine the amount of fluorescence, which corresponds to MMP activity. Total protein from HUVEC lysates is used to normalize the readings, and MMP activities are expressed as a percent relative to MMP activity from untreated control cells that did not receive oligonucleotide treatment. MMP activities were 78%, 82% and 58% in the culture media from cells treated with ISIS 133726, ISIS 29848 and ISIS 25237. These data reveal that ISIS 133726 did not inhibit MMP activity.

Example 42

Adipocyte Assay of Oligomeric Compounds Targeted to C-Reactive Protein

Insulin is an essential signaling molecule throughout the body, but its major target organs are the liver, skeletal muscle and adipose tissue. Insulin is the primary modulator of glucose homeostasis and helps maintain a balance of peripheral glucose utilization and hepatic glucose production. The reduced ability of normal circulating concentrations of insulin to maintain glucose homeostasis manifests in insulin resistance which is often associated with diabetes, central obesity, hypertension, polycystic ovarian syndrom, dyslipidemia and atherosclerosis (Saltiel, *Cell,* 2001, 104, 517-529; Saltiel and Kahn, *Nature,* 2001, 414, 799-806).

Response of Undifferentiated Adipocytes to Insulin

Insulin promotes the differentiation of preadipocytes into adipocytes. The condition of obesity, which results in increases in fat cell number, occurs even in insulin-resistant states in which glucose transport is impaired due to the antilipolytic effect of insulin. Inhibition of triglyceride breakdown requires much lower insulin concentrations than stimulation of glucose transport, resulting in maintenance or expansion of adipose stores (Kitamura et al., *Mol. Cell. Biol.*, 1999, 19, 6286-6296; Kitamura et al., *Mol. Cell. Biol.*, 1998, 18, 3708-3717).

One of the hallmarks of cellular differentiation is the upregulation of gene expression. During adipocyte differentiation, the gene expression patterns in adipocytes change considerably. Some genes known to be upregulated during adipocyte differentiation include hormone-sensitive lipase (HSL), adipocyte lipid binding protein (aP2), glucose transporter 4 (Glut4), and peroxisome proliferator-activated receptor gamma (PPAR-γ). Insulin signaling is improved by compounds that bind and inactivate PPAR-γ, a key regulator of adipocyte differentiation (Olefsky, *J. Clin. Invest.*, 2000, 106, 467-472). Insulin induces the translocation of GLUT4 to the adipocyte cell surface, where it transports glucose into the cell, an activity necessary for triglyceride synthesis. In all forms of obesity and diabetes, a major factor contributing to the impaired insulin-stimulated glucose transport in adipocytes is the downregulation of GLUT4. Insulin also induces hormone sensitive lipase (HSL), which is the predominant lipase in adipocytes that functions to promote fatty acid synthesis and lipogenesis (Fredrikson et al., *J. Biol. Chem.*, 1981, 256, 6311-6320). Adipocyte fatty acid binding protein (aP2) belongs to a multi-gene family of fatty acid and retinoid transport proteins. aP2 is postulated to serve as a lipid shuttle, solubilizing hydrophobic fatty acids and delivering them to the appropriate metabolic system for utilization (Fu et al., *J. Lipid Res.*, 2000, 41, 2017-2023; Pelton et al., *Biochem. Biophys. Res. Commun.*, 1999, 261, 456-458). Together, these genes play important roles in the uptake of glucose and the metabolism and utilization of fats.

Leptin secretion and an increase in triglyceride content are also well-established markers of adipocyte differentiation. While it serves as a marker for differentiated adipocytes, leptin also regulates glucose homeostasis through mechanisms (autocrine, paracrine, endocrine and neural) independent of the adipocyte's role in energy storage and release. As adipocytes differentiate, insulin increases triglyceride accumulation by both promoting triglyceride synthesis and inhibiting triglyceride breakdown (Spiegelman and Flier, *Cell*, 2001, 104, 531-543). As triglyceride accumulation correlates tightly with cell size and cell number, it is an excellent indicator of differentiated adipocytes.

The effect of antisense inhibition of C-reactive protein by on the expression of markers of cellular differentiation was examined in preadipocytes. Human white preadipocytes (Zen-Bio Inc., Research Triangle Park, N.C.) were grown in preadipocyte media (ZenBio Inc., Research Triangle Park, N.C.). One day before transfection, 96-well plates were seeded with approximately 3000 cells/well.

A randomized control oligonucleotide, ISIS 29848 (NNNNNNNNNNNNNNNNNNNN; where N is A, T, C or G; herein incorporated as SEQ ID NO:617) was used a negative control, a compound that does not modulate adipocyte differentiation. Tumor necrosis factor-alpha (TNF-α), which inhibits adipocyte differentiation, was used as a positive control for the inhibition of adipocyte differentiation as evaluated by leptin secretion. For all other parameters measured, ISIS 105990 (AGCAAAAGATCAATCCGTTA, incorporated herein as SEQ ID NO:622), an inhibitor of PPAR-γ, served as a positive control for the inhibition of adipocyte differentiation. ISIS 29848 and ISIS 105990 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Oligonucleotide was mixed with LIPOFECTIN™ reagent (Invitrogen Life Technologies, Carlsbad, Calif.) in OPTI-MEM™ medium (Invitrogen Life Technologies, Carlsbad, Calif.) to achieve a final concentration of 250 nM of oligonucleotide and 7.5 μg/mL LIPOFECTIN™ reagent. Before adding to cells, the oligonucleotide, LIPOFECTIN™ reagent and OPTI-MEM™ medium were mixed thoroughly and incubated for 0.5 hrs. Untreated control cells received LIPOFECTIN™ reagent only. The medium was removed from the plates and the plates were tapped on sterile gauze. Each well was washed in 150 μl of phosphate-buffered saline. The wash buffer in each well was replaced with 100 μL of the oligonucleotide/OPTI-MEM™ medium/LIPOFECTIN™ reagent cocktail. ISIS 133726 and ISIS 105990 were tested in triplicate, ISIS 29848 was tested in up to six replicate wells. The plates were incubated for 4 hours at 37° C., after which the medium was removed and the plate was tapped on sterile gauze. 100 μl of full growth medium was added to each well. After the cells have reached confluence (approximately three days), they were exposed for three days to differentiation media (Zen-Bio, Inc.) containing a PPAR-γ agonist, IBMX, dexamethasone, and insulin. Cells were then fed adipocyte media (Zen-Bio, Inc.), which was replaced at 2 to 3 day intervals.

Leptin secretion into the media in which adipocytes are cultured was measured by protein ELISA. On day nine post-transfection, 96-well plates were coated with a monoclonal antibody to human leptin (R&D Systems, Minneapolis, Minn.) and left at 4° C. overnight. The plates were blocked with bovine serum albumin (BSA), and a dilution of the treated adipocyte media was incubated in the plate at room temperature for 2 hours. After washing to remove unbound components, a second monoclonal antibody to human leptin (conjugated with biotin) was added. The plate was then incubated with strepavidin-conjugated horseradish peroxidase (HRP) and enzyme levels were determined by incubation with 3,3',5,5'-tetramethlybenzidine, which turns blue when cleaved by HRP. The $OD_{450}$ was read for each well, where the dye absorbance is proportional to the leptin concentration in the cell lysate. Results, shown in Table 29, are expressed as a percent control relative to untreated control samples. With respect to leptin secretion, values above or below 100% are considered to indicate that the compound has the ability to stimulate or inhibit leptin secretion, respectively.

The triglyceride accumulation assay measures the synthesis of triglyceride by adipocytes. Triglyceride accumulation was measured using the Infinity™ Triglyceride reagent kit (Sigma-Aldrich, St. Louis, Mo.). On day nine post-transfection, cells were washed and lysed at room temperature, and the triglyceride assay reagent was added. Triglyceride accumulation was measured based on the amount of glycerol liberated from triglycerides by the enzyme lipoprotein lipase. Liberated glycerol is phosphorylated by glycerol kinase, and hydrogen peroxide is generated during the oxidation of glycerol-1-phosphate to dihydroxyacetone phosphate by glycerol phosphate oxidase. Horseradish peroxidase (HRP) uses $H_2O_2$ to oxidize 4-aminoantipyrine and 3,5 dichloro-2-hydroxybenzene sulfonate to produce a red-colored dye. Dye absorbance, which is proportional to the concentration of glycerol, was measured at 515 nm using an UV spectrophotometer. Glycerol concentration was calculated from a standard curve for each assay, and data were normalized to total cellular protein as determined by a Bradford assay (Bio-Rad Laboratories, Hercules, Calif.). Results, shown in Table 29, are expressed as a percent control relative to untreated control samples. From these data, values for triglyceride (TRIG) accumulation above or below 100% are considered to indicate that the compound has the ability to stimulate or inhibit triglyceride accumulation, respectively.

Expression of the four hallmark genes, HSL, aP2, Glut4, and PPARγ, was also measured in adipocytes transfected with compounds of the invention. Cells were lysed on day nine post-transfection, in a guanadinium-containing buffer and total RNA is harvested. The amount of total RNA in each sample was determined using a Ribogreen Assay (Invitrogen Life Technologies, Carlsbad, Calif.). Real-time PCR was performed on the total RNA using primer/probe sets for the adipocyte differentiation hallmark genes Glut4, HSL, aP2, and PPAR-γ. mRNA levels, shown in Table 29, are expressed as percent control relative to the untreated control values. With respect to the four adipocyte differentiation hallmark genes, values above or below 100% are considered to indicate that the compound has the ability to stimulate adipocyte differentiation, or inhibit it, respectively.

TABLE 29

Effects of antisense inhibition of Tudor-SN on adipocyte differentiation

| Treatment | Leptin | TRIG | aP2 | Glut4 | HSL | PPARγ |
|---|---|---|---|---|---|---|
| ISIS 133726 | 85 | 67 | 93 | 63 | 99 | 77 |
| ISIS 29848 | 94 | 76 | 87 | 70 | 87 | 72 |
| ISIS 105990 | N.D. | 38 | 55 | 53 | 55 | 38 |
| TNF-α | 27 | N.D. | N.D. | N.D. | N.D. | N.D. |

ISIS 133726 reduced the expression levels leptin, triglycerides and GLUT4, suggesting that this antisense oligonucleotide is a candidate agent for applications where inhibition of adipocytes differentiation is desirable, for example, obesity, hyperlipidemia, atherosclerosis, atherogenesis, diabetes, hypertension, or other metabolic diseases, as well as having potential applications in the maintenance of the pluripotent phenotype of stem or precursor cells.

Example 43

Inflammation Assays Using Oligomeric Compounds Targeted to C-Reactive Protein

Inflammation assays are designed to identify genes that regulate the activation and effector phases of the adaptive immune response. During the activation phase, T lymphocytes (also known as T-cells) receiving signals from the appropriate antigens undergo clonal expansion, secrete cytokines, and upregulate their receptors for soluble growth factors, cytokines and co-stimulatory molecules (Cantrell, Annu. Rev. Immunol., 1996, 14, 259-274). These changes drive T-cell differentiation and effector function. In the effecotr phase, response to cytokines by non-immune effector cells controls the production of inflammatory mediators that can do extensive damage to host tissues. The cells of the adaptive immune systems, their products, as well as their interactions with various enzyme cascades involved in inflammation (e.g., the complement, clotting, fibrinolytic and kinin cascades) represent potential points for intervention in inflammatory disease. The inflammation assay presented here measures hallmarks of the activation phase of the immune response.

Dendritic cells treated with antisense compounds are used to identify regulators of dendritic cell-mediated T-cell costimulation. The level of interleukin-2 (IL-2) production by T-cells, a critical consequence of T-cell activation (DeSilva et al., J. Immunol., 1991, 147, 3261-3267; Salomon and Bluestone, Annu. Rev. Immunol., 2001, 19, 225-252), is used as an endpoint for T-cell activation. T lymphocytes are important immunoregulatory cells that mediate pathological inflammatory responses. Optimal activation of T lymphocytes requires both primary antigen recognition events as well as secondary or costimulatory signals from antigen presenting cells (APC). Dendritic cells are the most efficient APCs known and are principally responsible for antigen presentation to T-cells, expression of high levels of costimulatory molecules during infection and disease, and the induction and maintenance of immunological memory (Banchereau and Steinman, Nature, 1998, 392, 245-252). While a number of costimulatory ligand-receptor pairs have been shown to influence T-cell activation, a principal signal is delivered by engagement of CD28 on T-cells by CD80 (B7-1) and CD86 (B7-2) on APCs (Boussiotis et al., Curr. Opin. Immunol., 1994, 6, 797-807; Lenschow et al., Annu. Rev. Immunol., 1996, 14, 233-258). Inhibition of T-cell co-stimulation by APCs holds promise for novel and more specific strategies of immune suppression. In addition, blocking costimulatory signals may lead to the development of long-term immunological anergy (unresponsiveness or tolerance) that would offer utility for promoting transplantation or dampening autoimmunity. T-cell anergy is the direct consequence of failure of T-cells to produce the growth factor IL-2 (DeSilva et al., J. Immunol., 1991, 147, 3261-3267; Salomon and Bluestone, Annu. Rev. Immunol., 2001, 19, 225-252).

Dendritic Cell Cytokine Production as a Measure of the Activation Phase of the Immune Response In a further embodiment of the present invention, the effect of ISIS 133726 (SEQ ID NO:36) was examined on the dendritic cell-mediated costimulation of T-cells. Dendritic cells (DCs, Clonetics Corp., San Diego, Calif.) were plated at approximately 6500 cells/well on anti-CD3 (UCHT1, Pharmingen-BD, San Diego, Calif.) coated 96-well plates in 500 U/mL granulocyte macrophase-colony stimulation factor (GM-CSF) and interleukin-4 (IL-4). DCs were treated with antisense compounds 24 hours after plating.

A randomized control oligonucleotide, ISIS 29848 (NNNNNNNNNNNNNNNNNNNN; where N is A, T, C or G; herein incorporated as SEQ ID NO:617) served as a negative control, a compound that does not affect dendritic cell-mediated T-cell costimulation. ISIS 113131 (CGTGTGTCT-GTGCTAGTCCC, incorporated herein as SEQ ID NO:623), an inhibitor of CD86, served as a positive control for the inhibition of dendritic cell-mediated T-cell costimulation. ISIS 29848 and ISIS 113131 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Oligonucleotide was mixed with LIPOFECTIN™ reagent (Invitrogen Life Technologies, Carlsbad, Calif.) in OPTI-MEM™ medium (Invitrogen Life Technologies, Carlsbad, Calif.) to achieve a final concentration of 200 nM of oligonucleotide and 6 μg/mL LIPOFECTIN™ reagent. Before adding to cells, the oligonucleotide, LIPOFECTIN™ reagent and OPTI-MEM™ medium were mixed thoroughly and incubated for 0.5 hrs. The medium was removed from the cells and the plates were tapped on sterile gauze. Each well was washed in 150 μl of phosphate-buffered saline. The wash buffer in each well was replaced with 100 μL of the oligonucleotide/OPTI-MEM™ medium/LIPOFECTIN™ reagent cocktail. Untreated control cells received LIPOFECTIN™ reagent only. ISIS 133726 and the positive control were tested in triplicate, and the negative control oligonucleotide was tested in up to six replicates. The plates were incubated with oligonucleotide for 4 hours at 37° C., after which the medium was removed and the plate was tapped on sterile gauze. Fresh growth media plus cytokines was added and DC culture was continued for an additional 48 hours. DCs are then co-cultured with Jurkat T-cells in RPMI medium (Invitrogen Life Technologies, Carlsbad, Calif.) supplemented with 10% heat-inactivated fetal bovine serum (Sigma Chemical Company, St. Louis, Mo.). Culture supernatants are collected 24 hours later and assayed for IL-2 levels (IL-2 DUOSET™ kit, R&D Systems, Minneapolis, Minn.), which are expressed as a percent relative to untreated control samples. A value greater than 100% indicates an induction of the inflammatory response, whereas a value less than 100% demonstrates a reduction in the inflammatory response.

The culture supernatant of cells treated with ISIS 133726, ISIS 29848 and ISIS 113131 contained IL-2 at 84%, 83% and 55% of the IL-2 concentration found in culture supernatant from untreated control cells, respectively. These results indicate that ISIS 133726 did not inhibit T-cell co-stimulation.

Cytokine Signaling as a Measure of the Effector Phase of the Inflammatory Response The cytokine signaling assay is designed to identify genes that regulate inflammatory responses of non-immune effector cells (initially endothelial cells) to both IL-1β and TNF-α (Heyninck et al., *J Cell Biol*, 1999, 145, 1471-1482; Zetoune et al., *Cytokine*, 2001, 15, 282-298). Response to cytokine stimulation is monitored by tracking the expression levels of four genes: A20, intracellular adhesion molecule 1 (ICAM-1), interleukin-9 (IL-8) and macrophage-inflammatory protein 2 (MIP2α). As described below, these genes regulate numerous parameters of the inflammatory response. Antisense oligonucleotides are used to identify genes that alter the cellular response to these cytokines.

A20 is a zinc-finger protein that limits the transcription of pro-inflammatory genes by blocking TRAF2-stimulated NK-κB signaling. Studies in mice show that TNF-α dramatically increases A20 expression in mice, and that A20 expression is crucial for their survival (Lee et al., *Science*, 2000, 289, 2350-2354).

ICAM-1 is an adhesion molecule expressed at low levels on resting endothelial cells that is markedly up-regulated in response to inflammatory mediators like tumor necrosis factor-α (TNF-α), interleukin-1β (IL-1β) and interferon-γ (IFN-γ) (Springer, *Nature*, 1990, 346, 425-434). ICAM-1 expression serves to attract circulating leukocytes into the inflammatory site.

IL-8 is a member of the chemokine gene superfamily, members of which promote the pro-inflammatory phenotype of macrophages, vascular smooth muscle cells and endothelial cells (Koch et al., *Science*, 1992, 258, 1798-1801). IL-8 has been known as one of the major inducible chemokines with the ability to attract neutrophils to the site of inflammation. More recently, IL-8 has been implicated as a major mediator of acute neutrophil-mediated inflammation, and is therefore a potential anti-inflammatory target (Mukaida et al., *Cytokine Growth Factor Rev*, 1998, 9, 9-23).

MIP2α, another chemokine known to play a central role in leukocyte extravasation, has more recently been shown to be involved in acute inflammation (Lukacs et al., *Chem Immunol*, 1999, 72, 102-120). MIP2α is expressed in response to microbial infection, to injection of lipopolysaccharides (LPS), and to stimulation of cells with pro-inflammatory mediators such as IL-1β and TNF-α (Kopydlowski et al., *J Immunol*, 1999, 163, 1537-1544). Endothelial cells are one of several cell types that are sources of MIP2α (Rudner et al., *J Immunol*, 2000, 164, 6576-6582).

The effect of ISIS 133726 targeted to C-reactive protein was examined in human umbilical vascular endothelial cells (HUVECs) (ATCC, Manassus, Va.). HUVECs are cultured according to the supplier's recommendations. HUVECs are plated in a 96 well plate at a seeding density of approximately 3000 cells per well and are treated with antisense compounds 24 hours later.

A randomized control oligonucleotide, ISIS 29848 (NNNNNNNNNNNNNNNNNNNN; where N is A, T, C or G; herein incorporated as SEQ ID NO:617), was used as a negative control, a compound that does not affect cytokine signaling. ISIS 29848 is chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl (2'-MOE) nucleotides. The internucleoside (backbone) linkages are phosphorothioate (P=S) throughout the oligonucleotide. All cytidine residues are 5-methylcytidines.

Oligonucleotide was mixed with LIPOFECTIN™ reagent (Invitrogen Life Technologies, Carlsbad, Calif.) in OPTI-MEM™ medium (Invitrogen Life Technologies, Carlsbad, Calif.) to achieve a final concentration of 75 nM of oligonucleotide and 2.25 μg/mL LIPOFECTIN™ reagent. Before adding to cells, the oligonucleotide, LIPOFECTIN™ reagent and OPTI-MEM™ medium were mixed thoroughly and incubated for 0.5 hrs. The medium was removed from the cells and the plates were tapped on sterile gauze. Each well was washed in 150 μl of phosphate-buffered saline. The wash buffer in each well was replaced with 100 μL of the oligonucleotide/OPTI-MEM™ medium/LIPOFECTIN™ reagent cocktail. Untreated control cells received LIPOFECTIN™ reagent only. ISIS 133726 was tested in triplicate, and ISIS 29848 was tested in up to six replicate wells. The plates were incubated with oligonucleotide for 4 hours at 37° C., after which the medium was removed and the plate was tapped on sterile gauze. Fresh growth media plus cytokines was added and DC culture was continued for an additional 46 hours, after which HUVECS were stimulated with 0.1 ng/mL of IL-1β or 1 ng/mL TNF-α for 2 hours. Total RNA is harvested 48 hours post-transfection, and real time PCR is performed using primer/probe sets to detect A20, ICAM-1, IL-8 and MIP2α mRNA expression. Expression levels of each gene, shown in Table 30, are normalized to total RNA and values are expressed as a percent relative to untreated control samples. A value greater than 100% indicates an induction of the inflammatory response, whereas a value less than 100% demonstrates a reduction in the inflammatory response.

TABLE 30

Effects of antisense inhibition of C-reactive protein on the inflammatory response a

| Treatment | +IL-1β | | | | +TNF α | |
|---|---|---|---|---|---|---|
|  | A20 | ICAM-1 | IL-8 | MIP2α | IL-8 | MIP2α |
| ISIS 133726 | 95 | 64 | 77 | 58 | 130 | 77 |
| ISIS 29848 | 101 | 89 | 96 | 86 | 84 | 71 |

ISIS 133726 inhibited the expression of ICAM-1, IL-8 and MIP2α in response to IL-1 stimulation, and therefore is a candidate agent for the treatment of conditions in which inhibition or reduction of the inflammatory response is desirable, for example, in conditions such as rheumatoid arthritis, asthma and inflammatory bowel diseases. Conversely, ISIS 133726 stimulated the response of IL-8 in the presence of TNF-α, suggesting that in this stimulatory pathway, inhibition of C-reactive protein can stimulate an immune response, and is a candidate agent for the treatment of conditions in which stimulation of the immune response is desirable, for example, in conditions characterized by immunodeficiency.

Example 44

Antisense Oligonucleotides Targeted to Mouse C-Reactive Protein In Vivo

Lean Mouse Study

In a further embodiment, antisense oligonucleotides targeted to mouse C-reactive protein were tested for their effects on target expression, serum lipids, serum glucose and indicators of toxicity. Male C57Bl/6 mice (Charles River Laboratories, Wilmington, Mass.) were fed a standard rodent diet. Mice were given intraperitoneal injections of 50 mg/kg of each of ISIS 147868 (SEQ ID NO:580) and ISIS 147880 (SEQ ID NO:592). Each oligonucleotide-treated group consisted of 5 mice. A total of 5 saline-injected animals served as controls. Injections were administered twice weekly for a period of 2 weeks. At the end of the treatment period, mice were sacrificed. No significant changes were observed in body weights, which were recorded weekly, nor in liver and spleen weights recorded at necropsy.

C-reactive protein mRNA expression in liver was measured by real-time PCR, as described by other examples herein. ISIS 147868 and ISIS 147880, at a 50 mg/kg dose, resulted in 48% and 5% reductions in mouse C-reactive protein mRNA, respectively.

Serum was collected for routine clinical analysis of ALT, AST, cholesterol (CHOL), glucose (GLUC), HDL-cholesterol (HDL), LDL-cholesterol (LDL) and triglycerides (TRIG). These parameters were measured by routine procedures using an Olympus Clinical Analyzer (Olympus America Inc., Melville, N.Y.). The data are presented in Table 31.

TABLE 31

Serum chemistry analysis of mice treated with antisense oligonucleotides targeted to mouse C-reactive protein

| Treatment | Dose mg/kg | ALT IU/L | AST IU/L | CHOL mg/dL | HDL mg/dL | LDL mg/dL | TG mg/dL | GLUC mg/dL |
|---|---|---|---|---|---|---|---|---|
| SALINE |  | 27 | 62 | 80 | 61 | 11 | 102 | 243 |
| 147868 | 50 | 25 | 56 | 82 | 61 | 12 | 113 | 214 |
| 147880 | 50 | 43 | 72 | 96 | 73 | 13 | 125 | 228 |

These data reveal that treatment with ISIS 147868 or ISIS 147880 did not result in changes in the serum parameters measured. Together, these results illustrate that ISIS 147868 reduced C-reactive protein mRNA expression in vivo without causing toxicity. ISIS 147880 did not cause toxicity in mice.

The invention claimed is:

1. A compound comprising a chimeric oligonucleotide 15 to 30 nucleobases in length, wherein said chimeric oligonucleotide comprises at least a 15 nucleobase portion having at least 90% complementarity to at least a 15 nucleobase portion of SEQ ID NO: 4 wherein said compound comprises at least an 8 contiguous nucleobase portion of the nucleotide sequence of SEQ ID NO: 186, or a salt thereof.

2. The compound of claim 1, wherein said compound is single-stranded.

3. The compound of claim 1, wherein said compound is double-stranded.

4. The compound of claim 1, wherein said chimeric oligonucleotide has a nucleobase sequence that is 95% complementary to SEQ ID NO: 4.

5. The compound of claim 1, wherein said chimeric oligonucleotide has a nucleobase sequence that is 100% complementary to SEQ ID NO: 4.

6. The compound of claim 1, wherein said chimeric oligonucleotide comprises at least one modified internucleoside linkage.

7. The compound of claim 1, wherein said chimeric oligonucleotide comprises at least one 2'-O-methoxyethyl sugar moiety.

8. The compound of claim 1, wherein said chimeric oligonucleotide comprises at least one phosphorothioate internucleoside linkage.

9. The compound of claim 1, wherein said chimeric oligonucleotide comprises at least one 5-methylcytosine.

10. The compound of claim 1, wherein said chimeric oligonucleotide comprises a segment of linked 2'deoxyribonucleosides positioned between wing segments, each wing segment having two to five linked nucleosides comprising modified sugar moieties, wherein each internucleoside linkage of said chimeric oligonucleotide is a phosphorothioate internucleoside linkage and wherein all cytosine residues are 5-methylcytosines.

11. The compound of claim 10, wherein said chimeric oligonucleotide comprises at least one bicyclic nucleic acid sugar moiety.

12. A compound that is 12-30 nucleobases in length comprising:

at least 8 contiguous nucleobases of SEQ ID NO: 186;

a 5' terminus having two to five consecutive 2'-O-methoxyethyl nucleosides;

a 3' terminus having two to five consecutive 2'-O-methoxyethyl nucleosides; and a gap portion having ten to sixteen consecutive 2'-deoxyribonucleosides positioned between said 5' terminus and said 3' terminus.

13. The compound of claim 12, wherein all internucleoside linkages are phosphorothioate internucleoside linkages.

14. The compound of claim 12, wherein all cytosine residues are 5-methylcytosines.

15. The compound of claim 12, wherein each terminus is two nucleosides in length and said gap portion is sixteen nucleosides in length.

16. The compound of claim 12, wherein each terminus is three nucleosides in length and said gap portion is fourteen nucleosides in length.

17. The compound of claim 12, wherein each terminus is four nucleosides in length and said gap portion is twelve nucleosides in length.

18. The compound of claim 12, wherein said compound has a nucleobase sequence consisting of SEQ ID NO: 186.

19. The compound of claim 12, wherein said compound has a nucleobase sequence having at least 95% complementarity to SEQ ID NO: 4.

20. The compound of claim 12, wherein said compound has a nucleobase sequence that is 100% complementary to SEQ ID NO: 4.

21. The compound of claim 1, wherein the salt is a sodium salt.

22. A composition comprising the compound of claim 21 and a pharmaceutically acceptable carrier or excipient.

23. A method of reducing expression of C-reactive protein in an animal, comprising administering to said animal a therapeutically or prophylactically effective amount of the oligomeric compound of claim 1 so that expression of C-reactive protein in said animal is inhibited.

24. The method of claim 23 wherein said animal is a human.

25. The method of claim 23, additionally comprising administering an anti-inflammatory compound.

26. A method of treating coronary artery disease, unstable angina, stroke, atherosclerosis, myocardial infarction, thrombosis, obesity, metabolic syndrome, diabetes, hyperlipidemia, acute coronary syndrome, or coronary artery stenting in an animal in need thereof, said method comprising administering to said animal a therapeutically or prophylactically effective amount of the compound of claim 1 so that expression of C-reactive protein in said animal is inhibited, thereby treating coronary artery disease, unstable angina, stroke, atherosclerosis, myocardial infarction, thrombosis, obesity, metabolic syndrome, diabetes, hyperlipidemia, acute coronary syndrome, or coronary artery stenting in the animal.

27. The method of claim 26, wherein said compound has a nucleobase sequence that is 95% complementary to SEQ ID NO: 4.

28. The method of claim 26, wherein said compound has a nucleobase sequence that is 100% complementary to SEQ ID NO: 4.

29. The method of claim 26, wherein all internucleoside linkages are phosphorothioate internucleoside linkages.

30. The method of claim 26, wherein all cytosine residues are 5-methylcytosines.

31. The method of claim 26, wherein each terminus is five nucleosides in length and said gap portion is ten nucleosides in length.

32. The method of claim 26, wherein each terminus is three nucleosides in length and said gap portion is fourteen nucleosides in length.

33. The method of claim 26, wherein each terminus is four nucleosides in length and said gap portion is twelve nucleosides in length.

34. The method of claim 26, wherein said compound is single-stranded.

35. The method of claim 26, wherein said compound is double-stranded.

36. The method of claim 26, wherein said animal is a human.

37. The compound of claim 1, wherein said compound comprises a portion having ten contiguous 2'-deoxyribonucleoside positioned between a 5' terminus and a 3' terminus, wherein said 5' terminus has five contiguous 2'-O-methoxyethylnucleosides, wherein said 3' terminus has five contiguous 2'-O-methoxyethylnucleosides, wherein each internucleoside linkage is a phosphorothioate internucleoside linkage, and wherein each cytosine is a 5-methylcytosine.

38. The compound of claim 12, wherein each terminus is five nucleosides in length and said gap portion is ten nucleosides in length.

39. The method of claim 26, wherein each terminus is five nucleosides in length and said gap portion is ten nucleosides in length.

40. The compound of claim 1, wherein the chimeric oligonucleotide is 20 nucleobases in length.

41. The method of claim 26, wherein said compound has a nucleobase sequence consisting of SEQ ID NO: 186.

42. The method of claim 26, wherein said chimeric oligonucleotide has a nucleobase sequence consisting of SEQ ID NO: 186, wherein the chimeric oligonucleotide comprises
    a) a gap segment of ten linked deoxynucleosides,
    b) a 5' wing segment consisting of five linked nucleosides
    c) a 3' wing segment consisting of five linked nucleosides
    wherein the gap segment is positioned between the 5' and 3' wing segments, wherein each nucleoside of each wing segment comprises s 2'-O-methoxyethyl sugar, wherein each internucleoside linkage is a phosphorothioate internucleoside linkage, and wherein each cytosine is a 5-methylcytosine.

43. A compound comprising an oligonucleotide 20 nucleobases in length, wherein said oligonucleotide has a nucleobase sequence consisting of SEQ ID NO:186, wherein the oligonucleotide comprises
    a) a gap segment of ten linked deoxynucleosides,
    b) a 5' wing segment consisting of five linked nucleosides
    c) a 3' wing segment consisting of five linked nucleosides
    wherein the gap segment is positioned between the 5' and 3' wing segments, wherein each nucleoside of each wing segment comprises a 2'-O-methoxyethyl sugar, wherein each internucleoside linkage is a phosphorothioate internucleoside linkage, and wherein each cytosine is a 5-methylcytosine.

44. The compound of claim 1, wherein said chimeric oligonucleotide comprises at least one modified sugar moiety.

45. The compound of claim 1, wherein said chimeric oligonucleotide comprises at least one modified nucleobase.

* * * * *